United States Patent
Franciskovich et al.

(10) Patent No.: US 7,666,866 B2
(45) Date of Patent: Feb. 23, 2010

(54) ANTITHROMBOTIC DIAMIDES

(75) Inventors: Jeffry Bernard Franciskovich, Zionsville, IN (US); David Kent Herron, Indianapolis, IN (US); Valentine Joseph Klimkowski, Carmel, IN (US); Angela Lynn Marquart, Greenwood, IN (US); John Joseph Masters, Fishers, IN (US); David Mendel, Indianapolis, IN (US); Andrew Michael Ratz, Zionsville, IN (US); Gerald Floyd Smith, Greenwood, IN (US); Michael Robert Wiley, Zionsville, IN (US); Ying Kwong Yee, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 289 days.

(21) Appl. No.: 11/719,972

(22) PCT Filed: Nov. 15, 2005

(86) PCT No.: PCT/US2005/041432

§ 371 (c)(1),
(2), (4) Date: May 23, 2007

(87) PCT Pub. No.: WO2006/057868

PCT Pub. Date: Jun. 1, 2006

(65) Prior Publication Data
US 2009/0062271 A1 Mar. 5, 2009

Related U.S. Application Data

(60) Provisional application No. 60/631,479, filed on Nov. 29, 2004.

(51) Int. Cl.
| | |
|---|---|
| A61K 31/535 | (2006.01) |
| A61K 31/445 | (2006.01) |
| A61K 31/44 | (2006.01) |
| A61K 31/425 | (2006.01) |
| A61K 31/42 | (2006.01) |
| A61K 31/41 | (2006.01) |
| A61K 31/415 | (2006.01) |
| A61K 31/40 | (2006.01) |
| A61K 31/38 | (2006.01) |
| A61K 31/34 | (2006.01) |
| C07D 265/30 | (2006.01) |
| C07D 211/44 | (2006.01) |
| C07D 213/00 | (2006.01) |
| C07D 277/00 | (2006.01) |
| C07D 261/18 | (2006.01) |
| C07D 257/04 | (2006.01) |
| C07D 231/00 | (2006.01) |
| C07D 207/00 | (2006.01) |
| C07D 333/22 | (2006.01) |
| C07D 333/00 | (2006.01) |
| C07D 307/02 | (2006.01) |

(52) U.S. Cl. .............. 514/231.2; 514/318; 514/353; 514/365; 514/378; 514/381; 514/406; 514/423; 514/424; 514/443; 514/448; 514/461; 514/473; 544/176; 546/194; 546/308; 548/200; 548/248; 548/250; 548/374.1; 548/537; 549/57; 549/72; 549/295; 549/487

(58) Field of Classification Search .............. 514/231.2, 514/318, 353, 365, 378, 381, 406, 423, 424, 514/443, 448, 461, 473; 544/176; 546/194, 546/308; 548/200, 248, 250, 374.1, 537; 549/57, 72, 295, 487

See application file for complete search history.

(56) References Cited

U.S. PATENT DOCUMENTS

| | | |
|---|---|---|
| 6,140,351 A | 10/2000 | Arnaiz et al. |
| 6,313,122 B1 | 11/2001 | Beight et al. |
| 6,313,151 B1 | 11/2001 | Beight et al. |
| 6,372,759 B1 | 4/2002 | Beight et al. |
| 6,376,515 B2 | 4/2002 | Zhu et al. |
| 6,417,200 B1 | 7/2002 | Beight et al. |
| 6,610,704 B1 | 8/2003 | Beight et al. |
| 6,635,657 B1 | 10/2003 | Beight et al. |
| 6,689,780 B1 | 2/2004 | Beight et al. |
| 6,844,367 B1 | 1/2005 | Zhu et al. |

(Continued)

FOREIGN PATENT DOCUMENTS

AU 2001-29827 10/2001

(Continued)

OTHER PUBLICATIONS

Zhu, et al.: "Factor Xa Inhibitors: Recent Advances in Anticoagulant Agents" Annual Reports in Medicinal Chemistry, (2000), 35, 83-102.

(Continued)

Primary Examiner—Joseph R Kosack
(74) Attorney, Agent, or Firm—Thomas E. Jackson

(57) ABSTRACT

This application relates to a compound of formula (I) (or a pharmaceutically acceptable salt of the compound) as defined herein, pharmaceutical compositions thereof, and its use as an inhibitor of factor Xa and/or thrombin, as well as a process for its preparation and intermediates therefor.

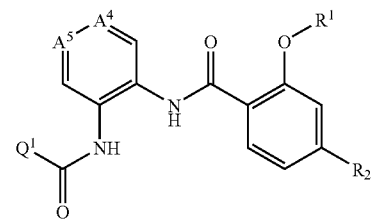

14 Claims, No Drawings

U.S. PATENT DOCUMENTS

| | | |
|---|---|---|
| 7,160,878 B2 | 1/2007 | Herron et al. |
| 7,163,938 B2 | 1/2007 | Herron et al. |
| 2004/0242581 A1 | 12/2004 | Herron et al. |
| 2007/0027185 A1 | 2/2007 | Franciskovich et al. |

FOREIGN PATENT DOCUMENTS

| | | |
|---|---|---|
| EP | 1 273 575 | 1/2003 |
| JP | 2000-302765 | 10/2000 |
| WO | WO 99/00121 | 1/1999 |
| WO | WO 99/42439 | 8/1999 |
| WO | WO 2004/108677 | 12/2004 |
| WO | WO 2006/057845 | 6/2006 |

OTHER PUBLICATIONS

Herron, David K. et al: "1,2-Dibenzamidobenzene Inhibitors of Human Factor Xa" J.Med.Chem. 43(5), 859-872 (2000).

Wiley, M. R. et al: "Structure-based design of potent, amidine-derived inhibitors of factor Xa: evaluation of selectivity, anticoagulant activity, and antithrombotic activity." J.Med.Chem 43(5), 883-899 (2000).

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Chromogenic Substrate for Factor Xa
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 1

Ile Glu Gly Arg
1

ANTITHROMBOTIC DIAMIDES

This application claims the benefit of U.S. Provisional Application No. 60/631,479, filed Nov. 29, 2004.

This invention relates to antithrombotic diamides which demonstrate activity as inhibitors of thrombin and/or factor Xa and, accordingly, which are useful antithrombotics in mammals. In particular it relates to antithrombotic diamides having high anticoagulant activity, good oral exposure and antithrombotic activity. Thus, this invention relates to new antithrombotic diamides which are inhibitors of thrombin and/or factor Xa, pharmaceutical compositions containing the antithrombotic diamides as active ingredients, and the use of the antithrombotic diamides as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic diamides are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6-24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, for example, B. Y. Zhu and R. M. Scarborough, *Annual Reports in Medicinal Chemistry*, (2000), 35, 83-102, Factor Xa Inhibitors: Recent Advances in Anticoagulant Agents.

Although the heparins and coumarins are effective anticoagulants, there still exists a need for anticoagulants which act selectively on factor Xa and/or thrombin, and which, independent of antithrombin III, exert inhibitory action shortly after administration, preferably by an oral route, and do not interfere with lysis of blood clots, as required to maintain hemostasis.

The present invention is directed to the discovery that the antithrombotic diamides of the present invention, as defined below, are potent inhibitors of thrombin and/or factor Xa which may have high bioavailability following oral administration.

According to the invention there is provided a compound of formula I

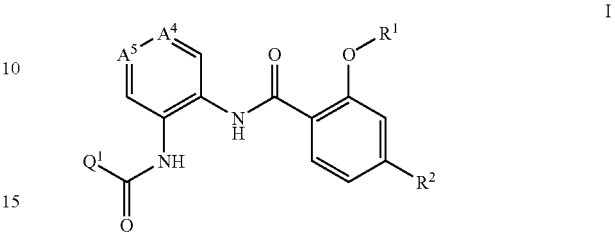

(or a pharmaceutically acceptable salt thereof) wherein:
each of $A^4$ and $A^5$ is CH, or
one of $A^4$ and $A^5$ is CH and the other is C—CN, or
one of $A^4$ and $A^5$ is CH and the other is N;

$Q^1$ is phenyl (in which the phenyl may bear one, two or three substituents at the 3-, 4- or 5-position(s) independently selected from halo, trifluoromethyl, cyano, carbamoyl, aminomethyl, methyl, methoxy, difluoromethoxy, hydroxymethyl, methylthio, formyl, acetyl, vinyl, nitro, amino, hydroxy and 3,4-methylenedioxy; and in addition the phenyl may bear a chloro, fluoro, methyl, methoxy, or nitro substituent at the 2- and/or 6-position), or $Q^1$ is 5-membered ring heteroaryl (which 5-membered ring heteroaryl is a 5-membered aromatic ring which includes one to three heteroatoms selected from sulfur, oxygen and nitrogen and which is attached to the carbonyl at a carbon atom and further which may bear one or more methyl substituents on carbon or nitrogen and may bear one or more halo substituents), or $Q^1$ is 6-membered ring heteroaryl (which 6-membered ring heteroaryl is a 6-membered aromatic ring which includes one or two nitrogens and further which may bear one or more amino, chloro, fluoro, nitro, methoxy, methylthio, trifluoromethyl or methyl substituents);

$R^1$ is —$(CH_2)_i$-Q-$(CH_2)_j$—$NRR^a$ wherein:

a) Q is a single bond and the sum of i and j is 2, 3 or 4;

b) Q is —$C(CH_3)_2$—, i is 1, and j is 1;

c) Q is —$CHR^b$, i is 0, j is 2, and $R^a$ and $R^b$ together are —$(CH_2)_2$—;

d) Q is —$CHR^b$, i is 2, j is 0, and $R^a$ and $R^b$ together are —$(CH_2)_4$—; or e) Q is —$NR^b$; i is 2; j is 2; and $R^a$ and $R^b$ together are —$(CH_2)_2$—;

wherein, unless defined above, $R^a$ is hydrogen;

R is hydrogen, (1-6C)alkyl, —$CH_2R^c$, phenethyl, —$COR^d$, —$COCOR^e$, —$CO(CH_2)_f$—$R^f$ (in which f is 1, 2 or 3), —$CONH$—$R^g$, —$CSNH$—$R^h$, —$CO$—$OR^i$, —$SO_2R^j$ or —$SO_2NHR^k$;

$R^c$ is (3-6C)cycloalkyl, phenyl (in which the phenyl may bear one, two or three substituents independently selected from halo, trifluoromethyl, cyano, carbamoyl, aminomethyl, methyl, (1-2C)alkoxy, difluoromethoxy, hydroxymethyl, (1-4C)alkylthio, formyl, acetyl, vinyl, nitro, amino, hydroxy and 3,4-methylenedioxy), 5-membered ring heteroaryl (which 5-membered ring heteroaryl is a 5-membered aromatic ring which includes one to three heteroatoms selected from sulfur, oxygen and nitrogen and which is attached to the methylene at a carbon atom and further which may bear one or more methyl substituents on carbon or nitrogen and may bear one or more halo substituents on carbon), 6-membered ring heteroaryl (which 6-membered ring heteroaryl is a 6-membered aromatic ring which includes one or two nitrogens and further which may bear one or more amino, chloro, fluoro, nitro, methoxy, methylthio, trifluoromethyl or methyl substituents) or aminocarbonyl;

$R^d$ is (1-6C)alkyl, (3-6C)cycloalkyl (which cycloalkyl may bear one or two (1-4C)alkyl groups or a phenyl group), 2-adamantyl, phenyl (in which the phenyl may bear one, two or three substituents independently selected from halo, trifluoromethyl, cyano, carbamoyl, aminomethyl, methyl, (1-2C) alkoxy, difluoromethoxy, hydroxymethyl, (1-4C)alkylthio, formyl, acetyl, vinyl, nitro, amino, hydroxy and 3,4-methylenedioxy), 5-membered ring heteroaryl (which 5-membered ring heteroaryl is a 5-membered aromatic ring which includes one to three heteroatoms selected from sulfur, oxygen and nitrogen and which may bear one or more (1-4C)alkyl substituents on carbon and a methyl substituent on nitrogen and may bear one or more halo substituents or a methylsulfonyl substituent on carbon), 6-membered ring heteroaryl (which 6-membered ring heteroaryl is a 6-membered aromatic ring which includes one or two nitrogens and further which may bear one or more amino, chloro, fluoro, nitro, methoxy, methylthio, trifluoromethyl or methyl substituents), benzo[b]thien-2-yl, 1-methyl-5-oxopyrrolidin-3-yl, 2,2-dimethyl-5-oxotetrahydrofuran-3-yl, or 4-morpholinyl;

or —$COR^d$ is the acyl residue of a naturally occurring α-amino acid or a protected derivative thereof wherein the protecting group is comprised of a t-butoxycarbonyl (BOC) group for an amino residue, a t-butyl ether (O-t-Bu) group for a hydroxy residue, a benzylthioether (S-benzyl) for a sulfhydryl residue, an im-benzyl for a histidine imidazole residue and a benzyl ester for a carboxy residue, and wherein a methionine sulfur group may instead be the oxo or dioxo derivative and a proline nitrogen may bear a methyl, or the acyl residue is (S)-5-oxopyrrolidin-2-ylcarbonyl[L-pyroglutamyl], (R)-3-BOC-thiazolidin-4-ylcarbonyl or (R)-thiazolidin-4-ylcarbonyl;

$R^e$ is phenyl (which may bear one or more halo or methyl substituents), furanyl or thienyl;

$R^f$ is (3-6C)cycloalkyl, phenyl (which may bear one or more halo or methyl substituents) furanyl, thienyl, 4-methyl-1,2,5-thiadiazol-3-yl, pyridyl, carboxy, [(1-2C)alkoxy]carbonyl, dimethylamino, 4-morpholinyl, 1-tetrazolyl, or 2-(2-methoxyethoxy)ethoxy;

$R^g$ is (1-6C)alkyl, (3-6C)cycloalkyl, 2-adamantyl, phenyl (which may bear one or more halo, cyano or methyl substituents), —$(CH_2)_2R^w$ (in which $R^w$ is [(1-2C)alkoxy]-carbonyl or thienyl), —$(CH_2)_3R^x$ (in which $R^x$ is dimethylamino) or (S)-1-methoxycarbonyl-2-methylpropyl;

$R^h$ is phenyl (which may bear one or more halo or methyl substituents);

$R^i$ is (1-6C)alkyl, allyl, benzyl, 2-methoxyethyl or (1R,2S,5R)-2-methyl-5-isopropylcyclohexyl[(−)-methyl];

$R^j$ is phenyl (which may bear one or more halo, cyano or methyl substituents), 5-membered ring heteroaryl (which 5-membered ring heteroaryl is a 5-membered aromatic ring which includes one to three heteroatoms selected from sulfur, oxygen and nitrogen and which may bear one or more (1-4C) alkyl substituents on carbon and a methyl substituent on nitrogen and may bear one or more halo substituents or a pyridyl or [(1-2C)alkoxy]carbonyl substituent on carbon);

$R^k$ is phenyl (which may bear one or more halo, or methyl substituents); and $R^2$ is (1-4C)alkyl or —O—$R^q$ wherein $R^q$ is (1-4C)alkyl, 4-pyridinylmethyl or —$(CH_2)_2$—$R^r$, in which $R^r$ is 1-pyrrolidinyl, 1-piperidinyl or 4-morpholinyl.

As used herein, the expression a compound of formula I or the expression a compound of the invention includes the compound and any conventional prodrug thereof, as well as a pharmaceutically acceptable salt of said compound or prodrug.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted. Amino acids are those L-amino acids commonly found in naturally occurring proteins and are listed in WIPO standard ST.25 (1998), Appendix 2, Table 3.

Particular values for the groups and ranges defined herein include the following: halo is fluoro, chloro, bromo or iodo; for an alkyl group or the alkyl portion of an alkoxy or alkylthio group: (1-2C)alkyl is methyl or ethyl; (1-4C)alkyl is methyl, ethyl, propyl, isopropyl, butyl, 2-methylpropyl or t-butyl; (1-6C)alkyl is methyl, ethyl, propyl, isopropyl, butyl, 2-methylpropyl, t-butyl, pentyl, 3-methylbutyl, 2,2-dimethylpropyl, hexyl or 3,3-dimethylbutyl; (3-6C)cycloalkyl is cyclopropyl, cyclobutyl, cyclopentyl or cyclohexyl.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin and/or factor Xa, it being well known in the art how to prepare or isolate particular forms and how to determine inhibitory properties against thrombin and/or factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

One particular compound of formula I is one wherein $Q^1$ is 4-methoxyphenyl, 4-chlorophenyl or 5-chloropyridin-2-yl; and, more particularly, wherein $Q^1$ is 4-methoxyphenyl.

Another particular compound, as described above is one wherein $R^2$ is t-butyl, methoxy, ethoxy, 4-pyridinylmethoxy or —O—$(CH_2)_2$—$R^r$, in which $R^r$ is 1-pyrrolidinyl, 1-piperidinyl or 4-morpholinyl; and, more particularly, wherein $R^2$ is t-butyl, methoxy or ethoxy.

A further particular compound, as described above, is one wherein R is hydrogen, isopropyl, 2,2-dimethylpropyl, cyclopropylmethyl, benzyl (the phenyl of which may bear a methylenedioxy, ethoxy, t-butylthio, nitro, bromo, chloro or trifluoromethyl substituent or one or two independently selected fluoro, methyl or methoxy substituents), 2-thienylmethyl, 3-thienylmethyl (which may bear a 2-methyl substituent), 2-pyrrolylmethyl (which may bear a 1-methyl substituent), 5-methylimidazol-4-ylmethyl, 2-pyridylmethyl, aminocarbonylmethyl, phenethyl, acetyl, pivaloyl, 3-methylbutanoyl, 3,3-dimethylbutanoyl, 4-methylpentanoyl, 2-methylcyclopropylcarbonyl, trans-2-phenylcyclopropylcarbonyl, 4-t-butylcyclohexylcarbonyl, 2-adamantylcarbonyl, benzoyl (which may bear a fluoro, methyl, 4-t-butyl, methoxy or methylthio substituent), 2- or 3-furancarbonyl (which may bear a t-butyl, chloro or bromo substituent or one or two methyl substituents), 2- or 3-thiophenecarbonyl (which may bear a chloro, bromo, methyl or methylsulfonyl substituent or two chloro substituents or a bromo and a methyl substituent), 1-methylpyrrole-2-carbonyl, 5-methylisoxazol-3-ylcarbonyl, 5-thiazolylcarbonyl, 1-methylpyrazol-4-ylcarbonyl, 2-methyl-2H-pyrazol-3-ylcarbonyl 2,5-dimethyl-2H-pyrazol-3-ylcarbonyl, 2-pyridylcarbonyl, 3-pyridylcarbonyl (which may bear a chloro or methyl substituent at the 2-position), benzo[b]thien-2-ylcarbonyl, 1-methyl-5-oxopyrrolidin-3-ylcarbonyl, 2,2-dimethyl-5-oxotetrahydrofuran-3-ylcarbonyl, 4-morpholinylcarbonyl, 2-(2-fluorophenyl)-2-oxoacetyl, 2-(2-thienyl)-2-oxoacetyl, cyclohexylacetyl, 3-cyclohexyl-1-oxopropyl, 4-cyclohexyl-1-oxobutyl, 2-fluorophenylacetyl, 4-fluorophenylacetyl, 2-thienylacetyl, 3-(2-thienyl)-1-oxopropyl, 4-(2-thienyl)-1-oxobutyl, 3-thienylacetyl, 4-methyl-1,2,5-thiadiazol-3-ylacetyl, 3-(2-pyridyl)propanoyl, 3-carboxypropanoyl, dimethylaminoacetyl, 3-(4-morpholinyl)-1-oxopropyl, (1-tetrazolyl)acetyl, 2-(2-methoxyethoxy)ethoxyacetyl, —CONH—$R^g$ [in which $R^g$ is methyl, ethyl, isopropyl, butyl, cyclohexyl, 2-adamantyl, phenyl, 2-fluorophenyl, 2-chlorophenyl, 4-cyanophenyl, 2-(ethoxycarbonyl)ethyl, 2-(2-thienyl)ethyl, 2-(3-thienyl)ethyl, 3-(dimethylamino)propyl or (S)-1-methoxycarbonyl-2-methylpropyl], 2-fluorophenylaminothiocarbonyl, t-butoxycarbonyl, allyloxycarbonyl, benzyloxycarbonyl, (2-methoxyethoxy)carbonyl, (1R,2S,5R)-2-methyl-5-isopropylcyclohexyloxycarbonyl [(−)-menthyloxycarbonyl], 4-cyanophenylsulfonyl, 2-thienylsulfonyl, 2-methoxycarbonylthien-3-ylylsulfonyl, 5-(2-pyridinyl)thien-2-ylsulfonyl, 3,5-dimethylisoxazol-4-ylsulfonyl, 5-chloro-1,3-dimethylpyrazol-4-ylsulfonyl, (2-fluorophenyl)aminosulfonyl; or R is (S)-2,6-bis(BOC-amino)-1-oxohexyl[$N^2,N^6$-di-BOC-L-Lysyl], (S)-1-methylpyrrolidin-2-ylcarbonyl[1-methyl-L-Prolyl], (S)-2-(BOC-amino)-1-oxopropyl[N—BOC-L-Alanyl], (S)-2-(BOC-amino)-3-hydroxy-1-oxopropyl [N—BOC-L-Seryl], (S)-2-(BOC-amino)-4-methylthio-1-oxobutyl[N—BOC-L-Methionyl], (S)-2-(BOC-amino)-4-methylsulfinyl-1-oxobutyl[N—BOC—S-Oxo-L-methionyl], (2S,3R)-2-(BOC-amino)-3-t-butoxy-1-oxobutyl[N—BOC—O-t-Butyl-L-threonyl], (S)-2-(BOC-Amino)-3-(benzyloxycarbonyl)-1-oxopropyl[N—BOC-β-Benzyl-L-α-aspartyl], (2S,3S)-2-(BOC-amino)-3-methyl-1-oxopentyl [N—BOC-L-Isoleucyl], (S)-2-(BOC-amino)-4-methyl-1-oxopentyl[N—BOC-L-Leucyl], (S)-2-(BOC-amino)-3-methyl-1-oxobutyl[N—BOC-L-Valyl], (R)-3-BOC-thiazolidin-4-ylcarbonyl, or (S)-5-oxopyrrolidin-2-ylcarbonyl[L-Pyroglutamyl]. More particularly, the compound is one wherein R is hydrogen or a value of —$COR^d$.

A more particular compound according to the above definitions is a one wherein Q is a single bond and the sum of i and j is 3, or Q is —$CHR^b$, i is 0, j is 2, and $R^a$ and $R^b$ together are —$(CH_2)_2$—.

One antithrombotic diamide according to the above definitions is a Compound of formula I wherein each of $A^4$ and $A^5$ is CH.

Another antithrombotic diamide according to the above definitions is a Compound of formula I wherein $A^4$ is CH and $A^5$ is N.

A specific compound, or pharmaceutically acceptable salt thereof, is any one of those provided in the Examples.

A pharmaceutically acceptable salt of a compound of formula I of the instant invention is an acid-addition salt made from a basic compound of formula I and an acid which provides a pharmaceutically acceptable anion or a salt which is made from an acidic compound of formula I and a base which provides a pharmaceutically acceptable cation.

As an additional aspect of the invention there is provided a pharmaceutical composition comprising in association with a pharmaceutically acceptable carrier, diluent or excipient, a compound of formula I, or a pharmaceutically acceptable salt thereof, as provided in any of the descriptions herein.

Further, there is provided a pharmaceutical composition for treating a thromboembolic disorder containing as an active ingredient a compound of formula I, or a pharmaceutically acceptable salt thereof, as provided in any of the descriptions herein.

In addition, there is provided the use of a compound of formula I, or a pharmaceutically acceptable salt thereof, as described herein as an active ingredient in the manufacture of a medicament for use in producing an anticoagulant or antithrombotic effect.

The present invention also provides a method of inhibiting coagulation in a mammal, particularly a human, comprising administering to a mammal in need of treatment, a coagulation inhibiting dose of a compound of formula I, or a pharmaceutically acceptable salt thereof, having any of the definitions herein.

The present invention further provides a method of inhibiting thrombin and/or factor Xa comprising administering to a mammal, particularly a human, in need of treatment, a thrombin and/or factor Xa inhibiting dose of compound of formula I having any of the definitions herein.

Further, the present invention provides a method of treating a thromboembolic disorder comprising administering to a mammal, particularly a human, in need of treatment, an effective amount of a compound of formula I, or a pharmaceutically acceptable salt thereof, having any of the definitions herein.

Also, there is provided a compound of formula I, or a pharmaceutically acceptable salt thereof, having any of the definitions herein for use as an antithrombotic agent.

In addition, there is provided the use of a compound of formula I, or a pharmaceutically acceptable salt thereof, having any of the definitions herein for the manufacture of a medicament for treatment of a thromboembolic disorder.

A compound of formula I may be prepared by processes which include processes known in the chemical art for the production of structurally analogous compounds or by a novel process described herein. A novel process described herein provides another aspect of the invention. A process for the preparation of a compound of formula I (or a pharmaceutically acceptable salt thereof) and novel intermediates for the manufacture of a compound of formula I provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I, or a pharmaceutically acceptable salt thereof, as provided in any of the above descriptions, comprising the step selected from (A) acylating an amine of formula II,

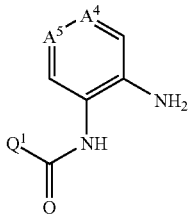

using an acid of formula III,

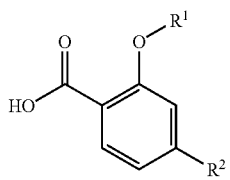

or an activated derivative thereof;

(B) acylating an amine of formula IV,

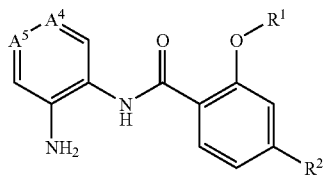

using an acid of formula $Q^1$-COOH or an activated derivative thereof;

(C) for a compound of formula I in which R is (1-6C)alkyl, —$CH_2R^c$ or phenethyl, alkylating a corresponding compound of formula I in which R is hydrogen;

(D) for a compound of formula I in which R is —$COR^d$, —$COCOR^e$, —$CO(CH_2)_f$—$R^f$, —$CONH$—$R^g$, —$CSNH$—$R^h$ or —$CO$—$OR^i$, acylating a corresponding compound of formula I in which R is hydrogen;

(E) for a compound of formula I in which R is —$SO_2R^j$ or —$SO_2NHR^k$, sulfonylating a corresponding compound of formula I in which R is hydrogen;

(F) for a compound of formula I in which $R^2$ is —$OR^q$, alkylating the phenolic oxygen of a compound of formula V,

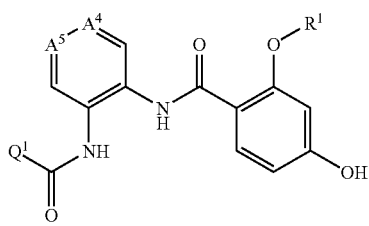

using a corresponding compound of formula Y—$R^q$ in which Y is a conventional leaving group for nucleophilic substitution;

(G) alkylating the phenolic oxygen of a compound of formula VI,

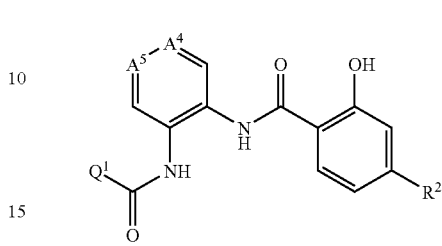

using a corresponding compound of formula Y—$R^1$, wherein Y is a conventional leaving group for nucleophilic substitution and wherein, for a compound of formula I in which i is 0, the stereochemistry of the carbon to which Y is attached is inverted from that of the product;

wherein, for any of the above procedures, a functional group which is present and not involved in the indicated procedure may be protected using a protecting group, whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or by any other conventional procedure;

and wherein, unless otherwise specified above, $A^4$, $A^5$, $Q^1$, $R^1$, and $R^2$ and the values therein have any of the values defined hereinabove.

As used herein, a nitrogen protecting group $R^p$ includes any conventional nitrogen protecting group which is appropriate for the relevant transformation(s) and compounds in terms of stability and removal. It may be preferred to introduce or change the nitrogen protecting group $R^p$ during the preparation of a compound. A typical value for $R^p$ is one which forms a urethane, such as for example a t-butoxycarbonyl or benzyloxycarbonyl group; however, $R^p$ will be other than a urethane when the intramolecular formation of a (cyclic) urethane is favorable, for example, $R^p$ may be a trifluoroacetyl or a phenylsulfonyl group. In addition, $R^p$ includes resin based protecting groups, such as the urethane formed with Wang-p-nitrophenyl carbonate (Wang-PNP) resin.

For a carboxylic acid herein, a typical activated derivative includes an ester (particularly a lower alkyl ester such as the methyl or ethyl ester), an acid halide (particularly the acid chloride), and an activated ester or anhydride (including the 4-nitrophenyl ester and an activated ester or mixed anhydride derived from a coupling reagent).

Reductive alkylation at nitrogen is described, for example, at Example 10, as well as in General Procedure B prior to Example 430 and in General Procedure E prior to Example 718.

As used herein, a leaving group "Y" is a moiety which is displaced in a nucleophilic substitution reaction, for example a halo group (such as bromo or iodo), a sulfonate ester group (such as methylsulfonyloxy, p-toluoylsulfonyloxy or trifluoromethylsulfonyloxy), or the reactive species derived from treating an alcohol with triphenylphosphine, diethyl azodicarboxylate and triethyl amine (in a Mitsunobu reaction). Alkylation at oxygen is described, for example, in the preparation of intermediate compounds at Examples 1-G, 2-B and 101-B, as well as in General Procedure F prior to Example 1203.

Acylating or sulfonylating the amino nitrogen of a compound of formula I in which R is hydrogen is conveniently carried out using an activated derivative of the corresponding acid, for example the acyl chloride or sulfonyl chloride, an anhydride or an activated ester or mixed anhydride derived from a coupling reagent, optionally in the presence of a base. When R is —CONH—$R^g$ or —CSNH—$R^h$, the acylating agent is conveniently the corresponding isocyanate or isothiocyanate. Acylations are described, for example, at Examples 2-F, 6 and 9, as well as in General Procedure A prior to Example 103, General Procedure D prior to Example 118, and General Procedure C prior to Example 315.

If not commercially available, a necessary starting material for the preparation of a compound of formula I may be prepared by a novel process described herein or one analogous thereto or by a procedure which is selected from standard techniques of organic chemistry, including aromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. A novel intermediate or starting material compound provides a further aspect of the invention.

Selective methods of substitution, protection and deprotection are well known in the art for preparation of a compound such as one of formulae II-VIII.

Thus, one particular intermediate is an acid of formula III, or a salt thereof, or an activated derivative thereof,

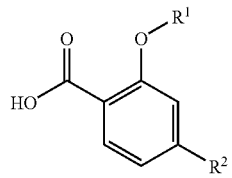

III wherein $R^1$ and $R^2$ have any of the values defined herein above (and in which R as hydrogen may be replaced by a nitrogen protecting group $R^p$). Conveniently, the salt of a carboxylic acid herein may be the lithium, sodium or potassium salt.

Another aspect is an amine of formula IV

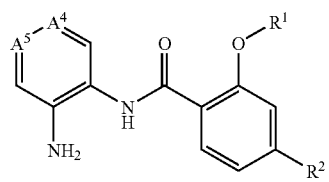

IV (in which R as hydrogen may be replaced by a nitrogen protecting group $R^p$), wherein $A^4$, $A^5$, $R^1$ and $R^2$, and the values therein, have any of the values defined herein.

A further intermediate is a compound of formula V,

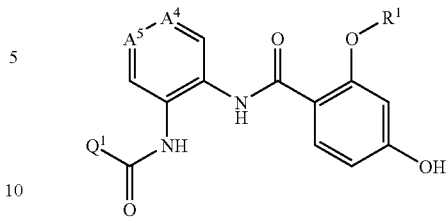

V (in which R as hydrogen may be replaced by a nitrogen protecting group $R^p$) wherein $A^4$, $A^5$, $Q^1$ and $R^1$, and the values therein, have any of the values defined herein.

An additional intermediate is a compound of formula VI,

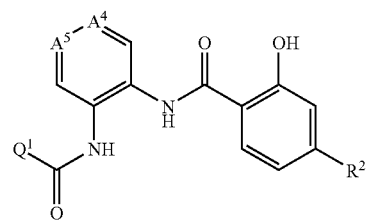

VI wherein $A^4$, $A^5$, $Q^1$ and $R^2$, and the values therein, have any of the values defined herein.

As an another aspect of the invention there is provided compound of formula I as disclosed herein, but in which R as hydrogen is replaced by a nitrogen protecting group $R^p$, wherein $A^4$, $A^5$, $Q^1$, $R^1$ and $R^2$, otherwise, have any of the values defined herein.

An amine of formula II is conveniently obtained by reducing the nitro group of a corresponding compound of formula VII,

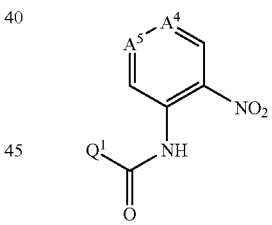

VII readily obtained by acylating the amino-nitro compound using an acid of formula $Q^1$-COOH, or an activated derivative thereof.

An amine of formula IV (in which R as hydrogen may be replaced by a nitrogen protecting group $R^p$) is conveniently obtained by reducing the nitro group of a corresponding compound of formula VIII,

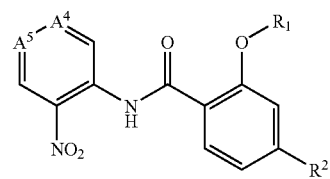

VIII (in which R as hydrogen may be replaced by a nitrogen protecting group $R^p$), readily obtained by acylating the aminonitro compound using an acid of formula III, or an activated derivative thereof.

As mentioned above, the invention includes a pharmaceutically acceptable salt of the thrombin and/or factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt.

Generally, a basic compound of the invention is isolated best in the form of an acid addition salt. A salt of a compound of formula I formed with an acid such as mentioned above is useful as a pharmaceutically acceptable salt for administration of the antithrombotic agent and for preparation of a pharmaceutical composition of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors.

The compounds of the invention are believed to selectively inhibit thrombin and/or factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin and/or factor Xa in a mammal comprising administering to a mammal in need of treatment an effective (thrombin and/or factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The thrombin and/or factor Xa inhibition, coagulation inhibition and thromboembolic disorder treatment contemplated by the present method includes both medical therapeutic and/or prophylactic treatment as appropriate.

In a further embodiment, the invention relates to treatment, in a human or animal, of a condition where inhibition of thrombin and/or factor Xa is required. The compounds of the invention are expected to be useful in mammals, including man, in treatment or prophylaxis of thrombosis and hypercoaguability in blood and tissues. Disorders in which the compounds have a potential utility are in treatment or prophylaxis of thrombosis and hypercoaguability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs, including joint replacement, and cardiac valves. Further, the compounds have expected utility in anticoagulant treatment in hemodialysis and disseminated intravascular coagulation. Further, the compounds may be useful in reducing the increased thrombin generation which occurs in the airways of patients with asthma; see, E. C. Gabazza, et al., *Lung*, (1999), 177(4), 253-262. A further expected utility is in rinsing or coating of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises a compound of formula I, or a pharmaceutically acceptable salt thereof, in association with a pharmaceutically acceptable carrier, diluent or excipient.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art.

The ability of a compound of the present invention to be an effective and orally active thrombin and/or factor Xa inhibitor may be evaluated in one or more of the following assays or in other standard assays known to those in the art.

The inhibition by a compound of the invention of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265-300. The inhibitor binding affinity is measured as apparent association constant Kass which is the hypothetical equilibrium constant for the reaction between enzyme and the test inhibitor compound (I).

$$\text{Enzyme} + I \rightleftharpoons \text{Enzyme} - I$$

$$Kass = \frac{[\text{Enzyme} - I]}{([\text{Enzyme}] \times [I])}$$

Conveniently, enzyme inhibition kinetics are performed in a high-volume protocol using automated dilutions of inhibitors (n=3 for each of four to eight inhibitor concentrations) into 96-well polystyrene plates and reaction rates are determined from the rate of hydrolysis of appropriate p-nitroanilide substrates at 405 nm using a Thermomax plate reader from Molecular Devices (San Francisco, Calif.). The same general protocol is followed for all enzymes studied: in each well is placed 50 μL buffer (0.06 M Tris, 0.3 M NaCl, pH 7.4), followed by 25 μL of inhibitor solution (in 100% methanol) and 25 μl enzyme solution (e.g. human factor Xa, 32 nM in 0.03 M.Tris, 0.15 M NaCl, 1 mg/mL HAS); finally, within two minutes, 150 μL aqueous solution of chromogenic substrate (e.g., 0.3 mM BzIle-Glu-Gly-Arg-pNA) is added to start the enzymatic reaction. Final factor Xa concentration is 3.2 nM. The rates of chromogenic substrate hydrolysis reactions provide a linear relationship with the enzymes studied such that free enzyme can be quantitated in reaction mixtures. Data is analyzed directly as rates by the Softmax program to produce calculations for tight-binding Kass determinations. For apparent Kass determinations, human factor Xa is used to hydrolyze BzIle-Glu-Gly-Arg-pNA (SEQ ID NO: 1); 5.9 nM human thrombin is used to hydrolyze 0.2 mM BzPhe-Val-Arg-pNA, 3.4 nM human plasmin is used with 0.5 mM HD-Val-Leu-Lys-pNA; 1.2 nM human nt-PA is used with 0.8 mM HD-Ile-Pro-Arg-pNA; and 0.4 nM urokinase is used with 0.4 mM pyro-Glu-Gly-Arg-pNA.

Kass is calculated for a range of concentrations of test compounds which produce hydrolysis inhibition of between 20% and 80% of control and the mean value reported in units of liter per mole. In general, a compound of formula I of the instant invention, as exemplified hereinbelow in the working examples, exhibits a Kass for factor Xa of $0.1$-$1,000 \times 10^6$ L/mole or greater. Most of the examples also exhibit a Kass for thrombin (factor IIa) of $0.3$-$100 \times 10^6$ L/mole or greater.

The thrombin and/or factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1-11 (1980; and Smith, et al., *Biochemistry*, 11, 2958-2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry* 11, 2958-2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1-11 (1980); and Smith, et al., *Biochemistry*, 11, 2958-2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163-174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL CaCl$_2$ (0.02 M). The thrombin time (TT) is measured by adding 0.05 mL saline and 0.05 mL thrombin (10 NIH units/mL) to 0.05 mL test plasma. Thus, the plasma concentrations are three times the assay concentrations. The compounds of formula I are added to human or animal plasma over a wide range of concentrations to determine prolongation effects on the APTT, PT, and TT assays. Linear extrapolations are performed to estimate the concentrations required to double the clotting time for each assay. Compounds of the instant invention extended the prolongation times in the APTT and PT assays.

Animals

Male Sprague Dawley rats (350-425 gm, Harlan Sprague Dawley Inc., Indianapolis, Ind.) are anesthetized with xylazine (20 mg/kg, s.c.) and ketamine (120 mg/kg, s.c.) or preferably are anesthetized using isoflurane anesthesia (2-3%, conveniently 2.5%, for surgery; 1.5-2.5%, conveniently 2.5%, for maintenance; flow rate kept at 0.5% throughout) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

FeCl$_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. FeCl$_3$ hexahydrate is dissolved in water and the concentration (20 percent) is expressed in terms of the actual weight of FeCl$_3$ only. To injure the artery and induce thrombosis, 2.85 µL is pipetted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, *Thromb. Res.*, 60:269, 1990).

Ex Vivo Coagulation Parameters

Ex vivo plasma thrombin time (TT), prothrombin time (PT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with isotonic saline (0.1 mL) and bovine thrombin (0.1 mL, 30 U/mL in TRIS buffer; Parke Davis) at 37° C. For PT, to plasma (0.1 mL) mixed with isotonic saline (0.1 mL) is added PT reagent (0.1 mL, Dade, Thromboplastin-C); and the fibrometer started immediately after the addition of the final reagent. For APTT, plasma (0.1 mL) and APTT solution (0.1 mL, Organon Teknika) are incubated for 5 minutes (37° C.); and CaCl$_2$ (0.1 mL, 0.025 M) is added to start coagulation. Assays are done in duplicate and averaged.

Index of Bioavailability

Bioavailability studies may be conducted as follows. Compounds are administered as aqueous solutions, or as solutions in 5% PEG 200, to male Fisher rats, intravenously (iv) at 5 mg/kg via tail vein injection and orally (po) as aqueous solutions, or as a suspension in 5% acacia, to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varian) cartridges for sample preparation and a methanol/30 nM ammonium acetate buffer (pH 4) gradient optimized for each compound. % Oral bioavailability is calculated by the following equation:

$$\% \text{ Oral bioavailability} = \frac{AUC\ po}{AUC\ iv} \times \frac{\text{Dose } iv}{\text{Dose } po} \times 100$$

where AUC is area under the curve calculated from the plasma level of compound over the time course of the experiment following oral (AUC po) and intravenous (AUC iv) dosing.

Compounds

For oral determinations, the compound may be administered orally, by gavage, as a suspension in 5% acacia to conscious fasted rats. The pretreatment time before flow is established through the shunt is selected based upon the peak apparent plasma concentration recorded in preliminary time course experiments that track apparent drug concentration in plasma following oral administration to conscious fasted rats, and typically varies between 1 to 5 hours. Animals used in antithrombotic efficacy experiments are anesthetized as described 15 minutes before the predetermined pretreatment time to allow for surgical preparation of the animals. Compound solutions are prepared fresh daily in normal saline or in 5% PEG200 in water for iv determinations and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thrombolysis model. Typically, bolus injection volume is 1 mL/kg for iv, and 5 mL/kg for po, and infusion volume is 3 mL/h. For a similar procedure run in the anesthetized rabbit, for example an infusion rate of 6.8 mL/h was used for one compound infused in 5% PEG200 in water.

Statistics

Results are expressed as means+/−SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months-2 years; 12-13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66-74° F.; 45-50 percent relative humidity; and lighted from 0600-1800 hours.

Pharmacokinetic Model.

Test compound is formulated immediately prior to dosing by making a suspension in a "wet granulation" (povidone, 0.85 mg/mL; lactose, 15.0 mg/mL; and polysorbate 80, 65 µL in 250 mL water). Dogs are given a single 20 mg/kg (in 25 mL of wet granulation) dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Male dogs (Beagles, as described above) are fasted overnight and dosed with test compound that is formulated immediately prior to dosing by making a suspension in a "wet granulation" as described above. Dogs are given a single dose of 5, 10 or 20 mg/kg (in 25 mL of wet granulation) of test compound by oral gavage. Based on the pharmacokinetics of the test compound, dogs are dosed either 1 or 2 hours prior to anesthesia. Dogs are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3-4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40-50 percent inhibition of the hyperemic blood flow response observed after 10-s mechanical occlusion of the LCX. All hemodynamic and ECG measurements are recorded and analyzed with a data acquisition system (Notochord HEM data analysis system, Croissy, France).

Thrombus Formation and Compound Administration Regimens

Electrolytic injury of the intima of the LCX is produced by applying 100-μA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment for a minimum of 30 minutes). The preparation is followed for 4 hours at which time the animal is euthanized and the thrombus is dissected from the LCX and weighed.

Hematology, Coagulation and Template Bleeding Time Determinations

Citrated blood (3 mL, 1 part 3.8% citrate:9 parts blood) is drawn before drug administration, at 60 min after administration, at 60 min after initiation of vessel injury and just prior to the end of the experiment. Whole blood cell counts, hemoglobin, and hematocrit values are determined on a 40-μL sample of the citrated whole blood with a hematology analyzer (Cell-Dyn 900, Sequoia-Turner, Mount View, Calif., U.S.A.). The remaining blood was centrifuged at 3,000 g for 5 min to prepare cell-free plasma. Plasma clotting times, prothrombin time (PT) and activated partial thromboplastin times (APTT) were performed using standard Dade reagents and the Coa-Screener coagulation device (American Labor, Largo, Fla.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Dunnet's post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, (1993), 21, 587-599.

Compounds of the instant invention are potent anticoagulant and antithrombotic agents which exhibit particularly good plasma exposure following oral administration, as evidenced by standard pharmacokinetic/pharmacodynamic assays.

The following Examples are provided to further describe the invention and are not to be construed as limitations thereof. Resin based reagents used in the examples are commercially available or well described in the literature. The term "aldehyde resin" refers to a formylpolystyrene resin. See, for example, X. Beebe et al., J. Amer. Chem. Soc., 114, 10061 (1992); J. M. Frechet and C. Schuerch, J. Amer. Chem. Soc., 93, 492 (1971). Generally, see S. W. Kaldor and M. G. Siegel, Current Opinion in Chem. Biol., 1, 101-106 (1997).

The abbreviations, symbols and terms used in the examples have the following meanings.

Ac=acetyl
Analysis=elemental analysis
aq=aqueous
Boc=t-butyloxycarbonyl
t-Bu=tert-butyl
Calcd=calculated
conc=concentrated
satd=saturated
DMF=dimethylformamide
DMSO=dimethylsulfoxide EtOAc=ethyl acetate
Et$_2$O=diethyl ether
HOAc=acetic acid
EtOH=ethanol
Hex=hexanes
MeOH=methanol
NMP=N-methylpyrrolidone
TFA=trifluoroacetic acid
THF=tetrahydrofuran
Et$_3$N=triethyl amine
mCPBA=meta-chloroperbenzoic acid
SCX=strong cation exchange
HPLC=High Performance Liquid Chromatography (including RPHPLC, reversed phase HPLC)
IR=Infrared Spectrum
$^1$NMR=(proton) nuclear magnetic resonance spectrum
ES-MS=electron spray mass spectrum
IS-MS=ion spray mass spectrum
FD-MS=field desorption mass spectrum When indicated without data, $^1$NMR, IR or MS means a satisfactory spectrum was obtained.

EXAMPLE 1

Preparation of N$^4$-(4-tert-Butyl-2-(piperidin-4-yloxy) benzoyl]-N$^3$-(4-methoxybenzoyl)-3,4-pyridinediamine

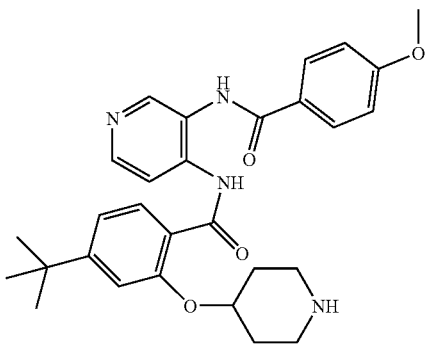

A. N$^4$-[2-(1-tert-Butoxycarbonylpiperidin-4-yloxy)-4-tert-butylbenzoyl]-N$^3$-(4-methoxybenzoyl)-3,4-pyridinediamine Using methods substantially equivalent to those described in Example 101-D, 2-(N-Boc-piperidine-4-yloxy)-4-(tert-butyl)benzoic acid (1.0 g, 2.65 mmol) is converted into the acid chloride and used to acylate N$^3$-(4-methoxybenzoyl)-3,4-pyridinediamine (600 mg, 2.47 mmol). After purification by chromatography (SiO$_2$: 30% to 50% EtOAc in chloroform) 589 mg (40%) of the title compound is obtained.
$^1$NMR
ES-MS, m/z 603.4 (m+1), 601.9 (M−1)−
Analysis for C$_{34}$H$_{42}$N$_4$O$_6$:
Calcd: C, 67.75; H, 7.02; N, 9.30.
Found: C, 67.05; H, 6.61; N, 9.09.

B. N$^4$-[4-tert-Butyl-2-(piperidin-4-yloxy)benzoyl]-N$^3$-(4-methoxybenzoyl)-3,4-pyridinediamine To an ice-water bath-chilled solution of N$^4$-[2-(1-tert-butoxycarbonylpiperidin-4-yloxy)-4-tert-butylbenzoyl]-N$^3$-(4-methoxybenzoyl)-3,4-pyridinediamine (460 mg, 764 micromoles) in dichloromethane (15 mL) was added trifluoroacetic acid (5 mL) and the mixture stirred on ice for 90 min. The mixture was then concentrated in vacuo, the oily residue redissolved in 1:1 dichloromethane:toluene (10 mL) and re-concentrated in vacuo to provide a pale tan-yellow oil. The oil was dissolved in methanol (10 mL) and applied to a 10 gram× 60 cubic centimeter strong cation exchange solid phase extraction column (SCX, Varian Sample Preparation Products, Harbor City, Calif.) that had been conditioned with methanol. After sample application, the cartridge was washed with methanol (4×50 mL) and the product was eluted with 3:1 chloroform:(2 M NH$_3$ in methanol) (3×40 mL). The eluates were concentrated in vacuo to afford N$^4$-[4-tert-butyl-2-(piperidin-4-yloxy)benzoyl]-N$^3$-(4-methoxybenzoyl)-3,4-pyridinediamine as a yellow oil (400 mg, 104%). This material was used without further purification.
IS-MS, m/z 503.2 (m+1), 501.3 (M−1)−.

The N$^3$-(4-methoxybenzoyl)-3,4-pyridinediamine starting material may be obtained as described in WO 99/00126 at Example 3-C.

The 2-(N-Boc-piperidine-4-yloxy)-4-(tert-butyl)benzoic acid starting material may be obtained as follows:

C. 1-Boc-4-hydroxypiperidine

To a mixture of 4-hydroxypiperidine (60.69 g, 0.6 mol), 4-(dimethylamino)pyridine (74 mg, 0.6 mmol), CH$_2$Cl$_2$ (150 mL), and THF (150 mL) was added di-t-butyl dicarbonate [(Boc)$_2$O] (130.95 g, 0.6 mol). After stirring for 6 h, the reaction mixture was heated to 35° C. for 16 h. More (Boc)$_2$O (13.09 g, 0.06 mol) in THF (20 mL) was added, and the mixture was heated for 10 h. After cooling, water and ether (1 L) were added and the mixture was stirred for 2 h. The organic layer was partitioned, dried (MgSO$_4$), and concentrated in vacuo. The residue was crystallized from ether to give the product as a white solid (105 g, 87%).
$^1$NMR (300 MHz, DMSO-d$_6$): δ 3.85 (m, 3H), 3.04 (m, 2H), 1.88 (m, 2H), 1.56 (m, 2H), 1.25 (s, 9H).
IS-MS, m/e: 202.0 (m+1).

D. 3-tert-Butylphenyl methoxymethyl ether

Chloromethyl methyl ether (MOMCl) (76 mL, 998 mmol) was added in one portion to a solution of 3-tert-butylphenol (50.04 g, 333 mmol), diisopropylethylamine (Hünig's base) (203 mL, 1.16 mol) and CH$_2$Cl$_2$ (225 mL) at 0° C. When the addition was complete, the solution was allowed to warm to 23° C., and after 21.5 h additional MOMCl (25 m, 329 mmol) and Hünig's base (60 mL, 344 mmol) were added at room temperature. After an additional 6 h, water (250 mL) was added, and the layers were separated. The organic layer was extracted with water (200 mL), 0.1 N HCl (2×200 mL) and saturated NaHCO$_3$ (200 mL). The organic layer was dried over MgSO$_4$, filtered and concentrated to yield 66.40 g of amber liquid which was purified by flash chromatography (5% EtOAc/hexanes) to provide 50.11 g (77%) of pale yellow liquid:
$^1$H NMR (300 MHz, CDCl$_3$) δ 7.24 (m, 1H, ArH), 7.07 (m, 2H, ArH), 6.90 (m, 1H, ArH), 5.19 (s, 2H, CH$_2$), 3.50 (s, 3H, CH$_3$), 1.33 (s, 9H, C(CH$_3$)$_3$);
$^{13}$C NMR (DMSO-d$_6$, 75 MHz) 156.7, 152.3, 128.9, 124.9, 118.6, 113.5, 112.7, 93.9, 55.5, 34.3, 30.9 ppm;
IR (CHCl$_3$) 1488, 1581, 1608, 1602, 2904, 2966 cm$^{-1}$;
MS (FD+) m/z 194 (100%).

E. 4-tert-Butyl-2-(methoxymethoxy)benzoic acid

A solution of tert-butyllithium (174 mL, 1.66 M in pentane) was added dropwise to a solution of 3-tert-butylphenyl methoxymethyl ether (49.35 g, 254 mmol) and ether (1 liter)

at 0° C. over 25 min. The resulting suspension was maintained at 0° C. for 2 h at which point $CO_2$ was sparged through for 20 min. The clear solution was allowed to warm, and water (500 mL) was added. The ether layer was extracted with water (300 mL) and was then discarded. Ether (500 mL) was added to the aqueous layer, and the pH was adjusted from 8-9 to 6 by treatment with 12 N HCl. The aqueous layer was further washed with ether (3×100 mL), and the combined organic layers were dried ($Na_2SO_4$), filtered and concentrated to 26.18 g (43%) of light yellow solid (mp 77.7-79.7° C.).

$^1$H NMR (300 MHz, $CDCl_3$) δ 8.08 (d, J=8.34 Hz, 1H, 6-ArH), 7.26 (d, J=1.62 Hz, 1H, 3-ArH), 7.20 (dd, J=1.60, 8.27 Hz, 1H, 5-ArH), 5.42 (s, 2H, $CH_2$), 3.57 (s, 3H, $CH_3$), 1.33 (s, 9H, $C(CH_3)_3$);

$^{13}$C NMR (DMSO-$d_6$, 75 MHz) 167.1, 156.2, 155.8, 130.6, 120.0, 118.6, 113.9, 95.1, 55.9, 34.8, 30.8 ppm; IR ($CHCl_3$) 1402, 1423, 1611, 1735, 2968, 3019 $cm^{-1}$;

MS (FD+) m/z 477 (7%), 283 (6%), 238 (100%), 193 (5%). Anal. for $C_{13}H_{18}HO_4$:

Calcd: C, 65.53; H, 7.61.

Found: C, 65.82; H, 7.81.

An alternate procedure is as follows: A solution of 3-tert-butylphenyl methoxymethyl ether (42.53 g, 219 mmol), tetramethylethylenediamine (TMEDA, 36.3 mL, 241 mmol) and ether (425 mL) was cooled to −42° C., and n-butyllithium (95.6 mL, 2.52 M in hexanes) was added over 10 min. During the addition the temperature rose to −33° C., and after the addition it was maintained between −30° C. and −17° C. for 1 h. The solution was slowly warmed to −10° C. resulting in a slurry which was stirred at this temperature for 2 h. Gaseous $CO_2$ was sparged through the slurry for 20 min. (After an initial exotherm to 16° C. the temperature fell to −4° C. for the remainder of the addition). The turbid solution was allowed to warm to 14° C. overnight under a $CO_2$ atmosphere, and water was (200 mL) was added which caused an exotherm, as well as effervescence. The resulting emulsion was placed in a separatory funnel with $Et_2O$ (100 mL) and 25% (w/w) NaCl (25 mL). The aqueous layer was extracted with $Et_2O$ (50 mL) and the combined organic layers were discarded. The aqueous layer was placed in a beaker with ether (600 mL) and the pH was adjusted from 10-11 to 6 with 12 N HCl. The aqueous layer was washed with ether (75 mL) and the combined organic layers were extracted with 0.25 N HCl (75 mL) to remove any residual TMEDA, and with 5% (w/w) $NaHCO_3$ (75 mL). The organic layer was dried ($MgSO_4$), filtered and evaporated to 28.84 g (55%) of 4-tert-butyl-2-(methoxymethoxy)benzoic acid.

F. Methyl 4-tert-butyl-2-hydroxybenzoate

A solution of 4-tert-butyl-2-(methoxymethoxy)benzoic acid (61.80 g, 259 mmol) and MeOH (865 mL) was cooled in an ice bath. Gaseous HCl was sparged through the cold fluid for 30 min to saturate it, and the solution was then heated to reflux. A Soxhlet extractor containing 3 Å molecular sieves was used to absorb the water produced in the reaction. After 16 h the heating mantle was removed, and the solution was allowed to cool to ambient temperature. The filtrate was concentrated to a thick semisolid which was taken up in 1:1 water/$CH_2Cl_2$ (800 mL). The aqueous layer was extracted once with $CH_2Cl_2$ (100 mL), and the combined organic layers were washed with water (250 mL) and 5% (w/w) $NaHCO_3$ (200 mL). The organic layer was dried ($MgSO_4$), filtered and concentrated to 49.54 g (92%) of yellow oil:

$^1$H NMR (300 MHz, $CDCl_3$) δ 7.74 (d, J=8.42 Hz, 1H, 6-ArH), 7.00 (d, J=1.62 Hz, 1H, 3-ArH), 6.92 (dd, J=1.64, 8.38 Hz, 1H, 5-ArH), 3.93 (s, 3H, $CO_2Me$), 1.30 (s, 9H, $C(CH_3)_3$); $^{13}$C NMR (DMSO-$d_6$, 75 MHz) 169.3, 160.1, 159.4, 129.5, 124.9, 116.8, 113.9, 109.9, 52.2, 34.8, 30.5 ppm;

MS (FD+) m/z 326 (100%), 208 (50%).

G. Methyl 4-(tert-Butyl)-2-(1-Boc-piperidin-4-yloxy)benzoate

To a stirring solution of methyl 4-tert-butyl-2-hydroxybenzoate (9.45 g, 45.4 mmol), 1-Boc-piperidin-4-ol (9.6 g, 47.7 mmol) and triphenylphosphine (12.5 g, 47.7 mmol) in THF (125 mL) was added, dropwise via an addition funnel, a solution of diisopropyl azodicarboxylate (9.4 mL, 47.7 mmol) in THF (25 mL). After 72 h, the solvent was removed in vacuo and the residue was dissolved in a minimal amount of chloroform and vacuum filtered through a pad of silica gel, eluting with a solution of 20% ethyl acetate in hexanes. The filtrate was then concentrated in vacuo and the residue was chromatographed over silica gel, eluting with a gradient of 5% ethyl acetate in hexanes through 20% ethyl acetate in hexanes. The product containing fractions were combined and concentrated in vacuo to give the ether (12.9 g, 73%) as a thick colorless oil.

$^1$NMR

ES-MS, m/e 392.3 (m+1)

H. 4-(tert-Butyl)-2-(1-Boc-piperidin-4-yloxy)benzoic acid

To a stirring solution of methyl 4-(tert-butyl)-2-(1-Boc-piperidin-4-yloxy)benzoate (12.9 g, 33 mmol) in p-dioxane (150 mL) was added a solution of LiOH hydrate (2.8 g, 66 mmol) in water (75 mL). The next morning, the solvent was removed in vacuo, and the residue was diluted with water (200 mL) and washed with diethyl ether. The aqueous phase was then adjusted to pH 3 with citric acid and extracted twice with diethyl ether. The combined ether extracts were then washed twice with brine, dried with $MgSO_4$, filtered and concentrated in vacuo to give 11.3 g (91%) of a white foam.

$^1$NMR

IS-MS, m/e 378.5 (m+1)

Analysis for $C_{21}H_{31}NO_5$:

Calcd: C, 66.82; H, 8.28; N, 3.71.

Found: C, 67.06; H, 8.39; N, 3.71.

EXAMPLE 2

Preparation of $N^3$-(4-Methoxybenzoyl)-$N^4$-[4-methoxy-2-[3-(2-thiophen-2-ylethyl-aminocarbonyl)aminopropoxy]benzoyl}-3,4-pyridinediamine

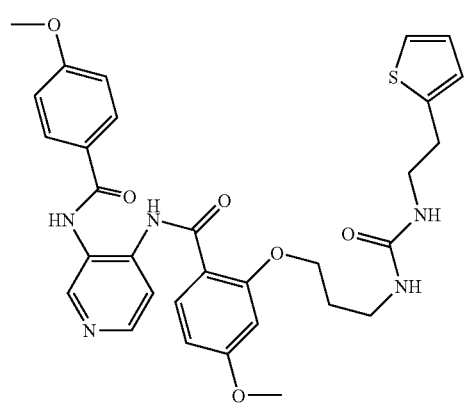

A. 1-tert-butoxycarbonylamino-3-bromopropane

To a solution of 3-bromopropylamine hydrobromide (100 g, 457 mmol) in water (250 mL) was added a solution of di-tert-butyl dicarbonate (49.84 g, 228 mmol) in dichloromethane (600 mL). The resulting biphasic mixture was stirred vigorously, then a solution of sodium hydroxide (36.56 g, 914 mmol) in water (250 mL) was added and the mixture was stirred at room temperature for 3 to 16 hours. The organic layer was washed sequentially with water, 0.2 N HCl until the pH reached 1, then again with water until the pH reached 6 to 7. The organic layer was dried over sodium sulfate and concentrated in vacuo to provide 45.18 grams (83%) of 1-tert-butoxycarbonylamino-3-bromopropane as a pale orange oil.

$^1$NMR

FAB-MS, m/z 238.0 (m+1), 240.0 (m+1).

Analysis for $C_8H_{16}BrNO_2$:

Calcd: C, 40.35; H, 6.77; N, 5.88.

Found: C, 40.12; H, 6.62; N, 6.06.

B. Methyl 2-(3-tert-butoxycarbonylaminopropoxy)-4-methoxybenzoate

To a solution of methyl 4-methoxysalicylate (11.48 g, 63 mmol) in dimethylformamide (30 mL) was added solid $K_2CO_3$ (13.06 g, 94.5 mmol), 1-tert-butoxycarbonylamino-3-bromopropane (22.5 g, 94.5 mmol), and freshly ground potassium iodide (1.5 g). The resulting slurry was placed under a nitrogen atmosphere and stirred for 2.5 days. The slurry was diluted with water (250 mL), washed with 1 N NaOH (2×250 mL), water (250 mL), and brine (250 mL), then dried over sodium sulfate and concentrated in vacuo. The crude mixture was purified on a preparative (Waters Prep LC™) 500 A chromatography apparatus using two silica columns and a hexanes through 1:1 hexanes:EtOAc gradient to provide methyl 2-(3-tert-butoxycarbonylaminopropoxy)-4-methoxybenzoate (19.93 g, 93.3%) as a colorless oil.

$^1$NMR

FAB-MS, m/z 340.2 (m+1).

Analysis for $C_{17}H_{25}NO_6$:

Calcd: C, 60.16; H, 7.43; N, 4.13.

Found: C, 59.92; H, 7.42; N, 4.18.

C. 2-(3-tert-Butoxycarbonylaminopropoxy)-4-methoxybenzoic acid

Methyl 2-(3-tert-butoxycarbonylaminopropoxy)-4-methoxybenzoate (18.61 g, 54.8 mmol) was suspended in 3:1 tetrahydrofuran:water (100 mL), then solid LiOH monohydrate (5.06 g, 121 mmol) was added and the mixture was stirred at 50° C. for 24 hours. The mixture was diluted with water (350 mL) and washed with diethyl ether (2×250 mL). The aqueous layer was acidified to pH 1-2 with 1 N sodium bisulfate and the resulting slurry was extracted with EtOAc (2×300 mL). The combined EtOAc layers were washed with brine, dried, then concentrated in vacuo to give a solid white mass. Recrystallization from EtOAc provided 2-(3-tert-butoxycarbonylaminopropoxy)-4-methoxybenzoic acid as white needles (15.52 g, 87%).

$^1$NMR

FAB-MS, m/z 312.2 (m+1).

Analysis for $C_{15}H_{21}NO_6$:

Calcd: C, 57.87; H, 6.80; N, 4.50.

Found: C, 58.09; H, 6.88; N, 4.57.

D. $N^4$-[2-(3-tert-Butoxycarbonylaminopropoxy)-4-methoxybenzoyl]-$N^3$-(4-methoxybenzoyl)-3,4-pyridinediamine 2-(3-tert-Butoxycarbonylaminopropoxy)-4-methoxybenzoic acid (1.6 g, 4.94 mmol) was dissolved in dry dichloromethane (20 mL) and DMF (0.5 mL) under nitrogen atmosphere. Oxalyl chloride (0.475 mL, 5.43 mmol) was added via syringe. Vigorous bubbling occurred. The mixture was stirred until gas evolution ceased, then concentrated in vacuo. The residue was dissolved in amylene-stabilized chloroform (20 mL), transferred to an addition funnel, then added dropwise over 2 hours to an ice cold solution of $N^3$-(4-methoxybenzoyl)-3,4-pyridinediamine (1.0 g, 4.11 mmol) in amylene-stabilized chloroform (30 mL) and pyridine (2 mL, 24.7 mmol). The mixture was allowed to warm to room temperature and stir for 2.5 days. The resulting slurry was diluted with dichloromethane (50 mL) and washed twice with saturated $NaHCO_3$, once with brine, then dried and concentrated in vacuo. Purification on a 6 mm chromatotron rotor with isocratic 96:3:1 $CHCl_3$:MeOH:triethylamine yielded about 80% pure material that was carried on directly.

E. $N^4$-[2-(3-Aminopropoxy)-4-methoxybenzoyl]-$N^3$-(4-methoxybenzoyl)-3,4-pyridinediamine $N^4$-[2-(3-tert-Butoxycarbonylaminopropoxy)-4-methoxybenzoyl]-$N^3$-(4-methoxybenzoyl)-3,4-pyridinediamine (1.0 g, 1.8 mmol) was dissolved in ice cold dichloromethane (20 mL). Trifluoroacetic acid (10 mL) was then added and the mixture stirred on ice for 1 hour. Modest gas evolution was observed. The mixture was concentrated in vacuo. The oily residue was redissolved in 1:1 toluene:dichloromethane (20 mL) and reconcentrated to give a brown oil. The brown oil was vigorously stirred overnight with a mixture of dichloromethane (50 mL) and potassium carbonate (3.4 g) in water (50 mL). The organic layer was washed with brine, dried and concentrated to give partially pure $N^4$-[2-(3-aminopropoxy)-4-methoxybenzoyl]-$N^3$-(4-methoxybenzoyl)-3,4-pyridinediamine as a brittle brown foam (0.74 g, 90%, about 50%-60% pure via TLC (9:1 dichloromethane:MeOH w/few drops of ammonium hydroxide). This material was used without further purification.

F. $N^3$-(4-Methoxybenzoyl)-$N^4$-{4-methoxy-2-[3-(2-thiophen-2-ylethylaminocarbonyl)aminopropoxy]benzoylamino}-3,4-pyridinediamine $N^4$-[2-(3-Aminopropoxy)-4-methoxybenzoyl]-$N^3$-(4-methoxybenzoyl)-3,4-pyridinediamine was dissolved in amylene stabilized chloroform (5 mL) and placed in a 20 mL scintillation vial. To this solution was added 2-thiophen-2-ylethylisocyanate (46 mg, 300 micromoles) in amylene stabilized chloroform (5 mL). The resulting mixture was agitated overnight at room temperature on an orbital platform shaker. Excess isocyanate was scavenged by shaking the reaction mixture with aminomethylated polystyrene (200 mg, 2.25 mmol/g) overnight. The slurry was filtered, the filtrate concentrated in vacuo and half of the material purified on a semipreparative reversed phase HPLC column (YMC 20×50 mm ODS-A, 0 through 100% solvent B over 10 minutes at 25 mL/min where solvent A=aqueous 0.1% (v/v) trifluoroacetic acid and where solvent B=0.08% (v/v) trifluoroacetic acid in acetonitrile). Appropriate fractions were pooled and lyophilized to provide $N^3$-(4-methoxybenzoyl)-$N^4$-{4-methoxy-2-[3-(2-thiophen-2-ylethylaminocarbonyl)aminopropoxy]benzoylamino}-3,4-pyridinediamine (20.7 mg, 39%) as a yellow glass.

IS-MS, m/z 604.2 (m+1), 602.4 (M−1)−

EXAMPLE 3

Preparation of N⁴-[2-[3-(2-Fluorophenylaminocarbonyl)aminopropoxy]-4-methoxybenzoylamino]-N³-(4-methoxybenzoyl)-3,4-pyridinediamine

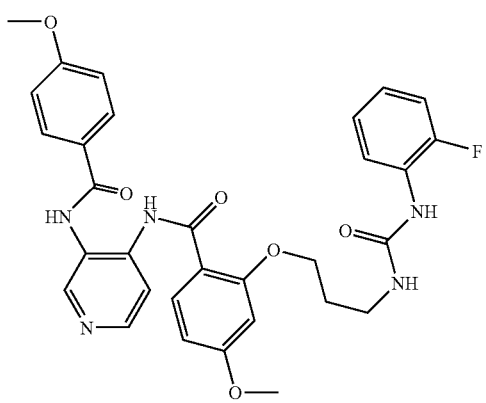

Using methods substantially equivalent to those described in Example 2-F, N⁴-[2-[3-(2-fluorophenylaminocarbonyl)aminopropoxy]-4-methoxybenzoylamino]-N³-(4-methoxybenzoyl)-3,4-pyridinediamine (18 mg, 26%) was prepared from N³-(4-methoxybenzoyl)-N⁴-[4-methoxy-2-(3-aminopropoxy)benzoyl]-3,4-pyridinediamine and 2-fluorophenyl isocyanate.

IS-MS, m/z 588.2 (m+1), 586.6 (M−1)−.

EXAMPLE 4

Preparation of N³-(4-methoxybenzoyl)-N⁴-[4-methoxy-2-[3-(thiophen-2-ylcarbonyl)aminopropoxy]benzoylamino]-3,4-pyridinediamine

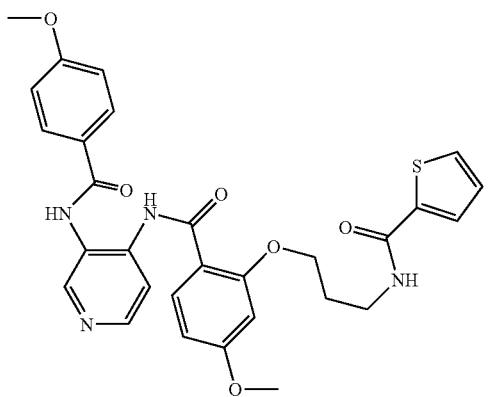

N³-(4-Methoxybenzoyl)-N⁴-[4-methoxy-2-(3-aminopropoxy)benzoyl]-3,4-pyridinediamine (106 mg crude, 230 μmol) in amylene stabilized chloroform (5 mL) was added to a suspension of piperidinomethylpolystyrene (230 mg, Fluka, 2.6-2.8 mmol/g) in amylene stabilized chloroform (5 mL). Subsequently, 2-thiophenecarbonyl chloride (44 mg, 300 μmol) was added to the mixture and it was shaken overnight at room temperature on an orbital platform shaker. Excess acid chloride was scavenged by shaking the mixture overnight with aminomethylated polystyrene (200 mg, 2.25 mmol/g). The slurry was filtered, concentrated and half of the residue purified via semipreparative HPLC as described in Example 2-F to provide N³-(4-methoxybenzoyl)-N⁴-[4-methoxy-2-[3-(thiophen-2-ylcarbonyl)aminopropoxy]benzoylamino]-3,4-pyridinediamine (14.6 mg, 23%) as a yellow glass.

IS-MS, m/z 561.2 (m+1), 559.4 (M−1)−.

EXAMPLE 5

Preparation of N³-(4-methoxybenzoyl)-N⁴-[4-methoxy-2-[3-[2-(methoxycarbonyl)thiophen-3-ylsulfonyl]aminopropoxy]benzoyl]-3,4-pyridinediamine

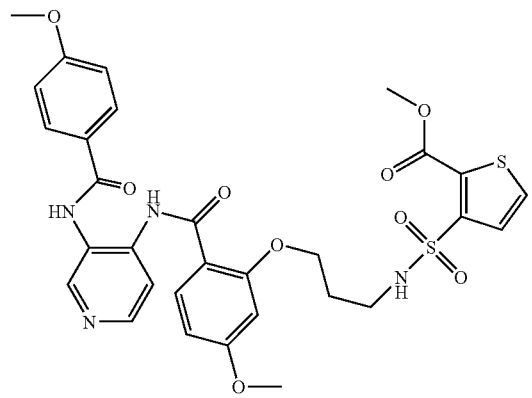

Using methods substantially equivalent to those in Example 4, N³-(4-methoxybenzoyl)-N⁴-[4-methoxy-2-[3-[2-(methoxycarbonyl)thiophen-3-ylsulfonyl]aminopropoxy]benzoyl]-3,4-diaminopyridine (18.2 mg, 24%) was prepared from N³-(4-benzoyl)-N⁴-[4-methoxy-2-(3-aminopropoxy)benzoyl]-3,4-pyridinediamine and 2-(methoxycarbonyl)thiophene-3-sulfonyl chloride.

IS-MS, m/z 655.2 (m+1), 653.2 (M−1)−.

EXAMPLE 6

Preparation of N³-(4-Methoxybenzoyl)-N⁴-[4-methoxy-2-[3-(1-methylpyrrol-2-ylcarbonyl)aminopropoxy]benzoyl]-3,4-pyridinediamine

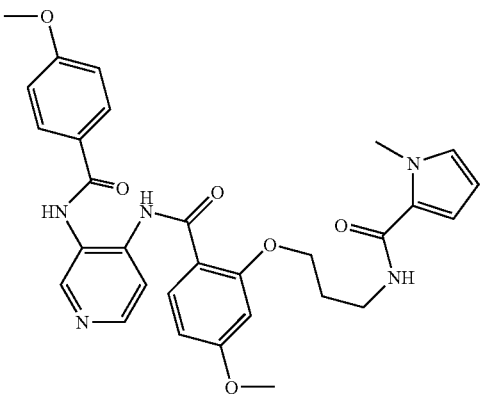

1-Methyl-2-pyrrolecarboxylic acid (57.6 mg, 460 μmol) was dissolved in amylene stabilized chloroform (8 mL). Resin-supported carbodiimide (1.1 g, 0.85 mm ol/g, 920 μmol) was added. To the resin-acid slurry was added N³-(4-methoxybenzoyl)-N⁴-[4-methoxy-2-(3-aminopropoxy)benzoyl]-3,4-pyridinediamine (106 mg crude, 230 μmol) in amylene stabilized chloroform (5 mL). The vial was capped and the reaction was agitated overnight on an orbital platform shaker. The slurry was filtered. The filtrate was concentrated and then purified by semipreparative HPLC as described in Example 2-F to provide N³-(4-methoxybenzoyl)-N⁴-[4-methoxy-2-[3-(1-methylpyrrol-2-ylcarbonyl)aminopropoxy]benzoyl]-3,4-pyridinediamine (17.3 mg, 27%) as ivory needles.

IS-MS, m/z 558.2 (m+1), 556.4 (M−1)−.

EXAMPLE 7

Preparation of N³-(4-Methoxybenzoyl)-N⁴-[4-methoxy-2-[3-(thiophen-3-ylcarbonyl)aminopropoxy]benzoyl]-3,4-pyridinediamine

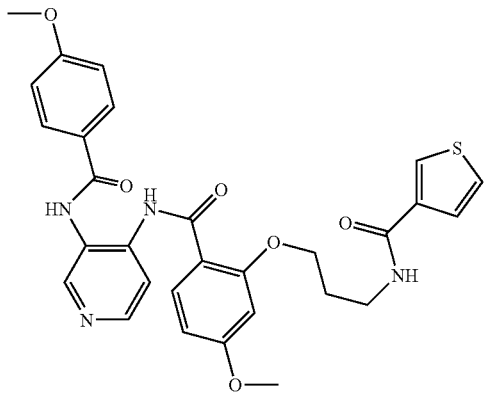

Using methods substantially equivalent to those described in Example 6, N³-(4-methoxybenzoyl)-N⁴-[4-methoxy-2-[3-(thiophen-3-ylcarbonyl)aminopropoxy]-benzoyl]-3,4-pyridinediamine (14 mg, 22%) was prepared from N³-(4-methoxybenzoyl)-N⁴-[4-methoxy-2-(3-aminopropoxy)benzoyl]-3,4-pyridinediamine and 3-thiophenecarboxylic acid.

IS-MS, m/z 561.2 (m+1), 559.4 (M−1)−.

EXAMPLE 8

Preparation of N⁴-[2-[3-(N-tert-Butoxycarbonyl-O-tert-butyl-L-threonyl)aminopropoxy]-4-methoxybenzoyl]-N-3-(4-methoxybenzoyl)-3,4-pyridinediamine

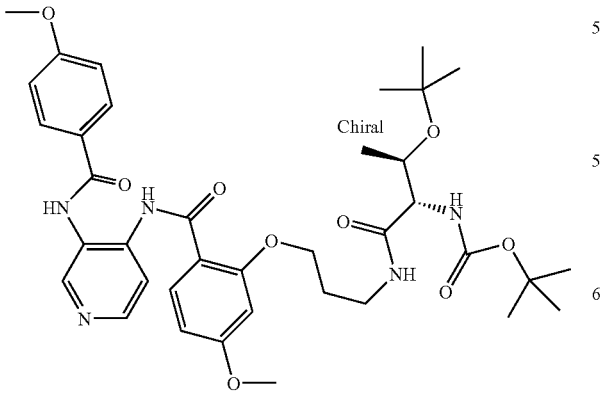

Using methods substantially equivalent to those described in Example 6, N⁴-[2-[3-(N-tert-butoxycarbonyl-O-tert-butyl-L-threonyl)aminopropoxy]-4-methoxybenzoyl]-N³-(4-methoxybenzoyl)-3,4-pyridinediamine (25.8 mg, 31%) was prepared from N³-(4-methoxybenzoyl)-N⁴-[4-methoxy-2-(3-aminopropoxy)benzoyl]-3,4-pyridinediamine and N-tert-butoxycarbonyl-O-tert-butyl-L-threonine.

IS-MS, m/z 708.2 (m+1), 706.6 (M−1)−.

EXAMPLE 9

Preparation of N⁴-[4-tert-Butyl-2-[1-(2-fluorophenylaminocarbonyl)piperidin-4-yloxy]benzoyl]-N³-(4-methoxybenzoyl)-3,4-pyridinediamine

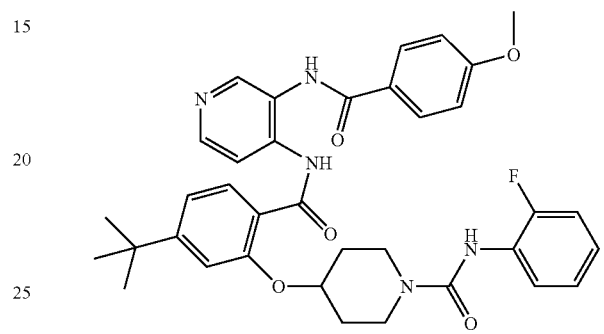

To a portion of N⁴-[4-tert-butyl-2-(piperidin-4-yloxy)benzoyl]-N³-(4-methoxybenzoyl)-3,4-diaminopyridine (38 mg, 76 μmol) in a 4 mL screw cap vial was added amylene stabilized chloroform (1 mL) and 2-fluorophenyl isocyanate (13.5 mg, 98 μmol, 1.3 eq). The vial was capped and shaken overnight at room temperature. The contents of the vial were then applied to a 1 gram 6 cubic centimeter SCX cartridge that was conditioned with methanol (2×5 mL). The cartridge was washed with methanol (4×5 mL) and the product was eluted with 0.5 N NH₃ in methanol (2×5 mL) and concentrated in vacuo. The residue was purified via silica gel chromatography (1 g, 6 cc Si cartridge, CH₂Cl₂ through 95:5 CH₂Cl₂:MeOH) to afford the title compound in quantitative yield as a yellow solid.

IS-MS, m/z 640.7 (m+1), 638.7 (M−1)−.

EXAMPLE 10

Preparation of N⁴-[4-tert-Butyl-2-(1-benzylpiperidin-4-yloxy)benzoyl]-N³-(4-methoxybenzoyl)-3,4-pyridinediamine

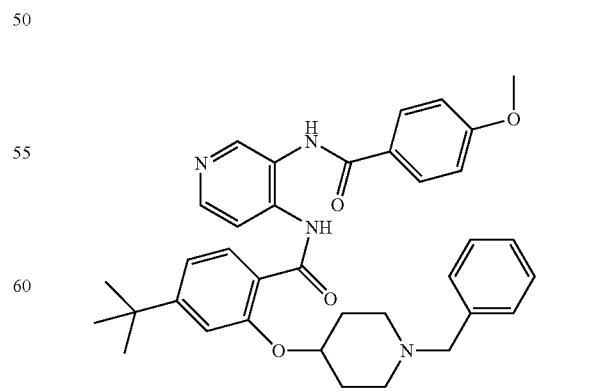

In a 4 mL screw cap vial, N⁴-[4-tert-butyl-2-(piperidin-4-yloxy)benzoyl]-N³-(4-methoxybenzoyl)-3,4-pyridinediamine (38 mg, 76 μmol) was dissolved in 1 mL of freshly prepared dry 95:5 MeOH:AcOH. Benzaldehyde (24.1 mg, 227 μmol, 3 eq) was added and the vial was capped. After 10 minutes, sodium cyanoborohydride solution (0.5 mL of a 19.0 mg/mL freshly prepared stock in dry 95:5 MeOH: AcOH, 9.51 mg NaCNBH$_3$, 151 μmol, 2 eq) was then added to the solution. The vial was re-capped and shaken overnight at room temperature. The mixture was then purified using the method described in Example 34-B to provide the desired compound as a yellow solid (47.5 mg, 106%).

IS-MS, m/z 593.7 (m+1), 591.9 (M−1)−

EXAMPLE 11

Preparation of N$^4$-[4-tert-Butyl-2-[1-(2-methoxybenzyl)piperidin-4-yloxy]benzoyl]-N$^3$-(4-methoxybenzoyl)-3,4-pyridinediamine

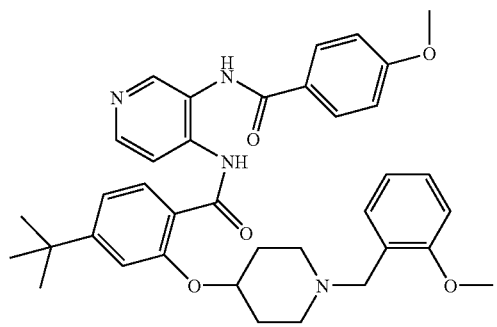

Using methods substantially equivalent to those described in Example 10, N$^4$-[4-tert-butyl-2-[1-(2-methoxybenzyl)piperidin-4-yloxy]benzoyl]-N$^3$-(4-methoxybenzoyl)-3,4-pyridinediamine (48.6 mg, 103%) was prepared from N$^4$-[4-tert-butyl-2-(piperidin-4-yloxy)benzoyl]-N$^3$-(4-methoxybenzoyl)-3,4-pyridinediamine and 2-methoxybenzaldehyde.

IS-MS, m/z 623.6 (m+1), 621.8 (M−1)−.

EXAMPLE 12

Preparation of N$^4$-[4-tert-Butyl-2-[1-(2-hydroxybenzyl)piperidin-4-yloxy]benzoyl]-N$^3$-(4-methoxybenzoyl)-3,4-pyridinediamine

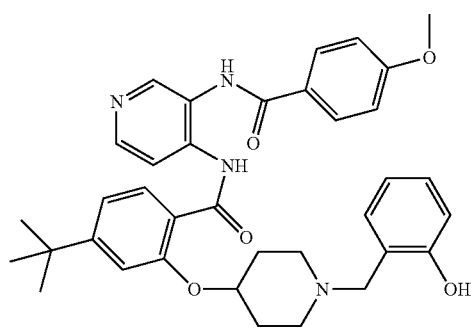

Using methods substantially equivalent to those described in Example 10, N$^4$-[4-tert-Butyl-2-[1-(2-hydroxybenzyl)piperidin-4-yloxy]benzoyl]-N$^3$-(4-methoxybenzoyl)-3,4-pyridinediamine (41.7 mg, 90%) was prepared from N$^4$-[4-tert-butyl-2-(piperidin-4-yloxy)benzoyl]-N$^3$-(4-methoxybenzoyl)-3,4-pyridinediamine and 2-hydroxybenzaldehyde.

IS-MS, m/z 609.3 (m+1), 607.5 (M−1)−.

EXAMPLE 13

Preparation of N$^4$-[4-tert-Butyl-2-[1-(2-methylbenzyl)piperidin-4-yloxy]benzoyl]-N$^3$-(4-methoxybenzoyl)-3,4-diaminopyridine

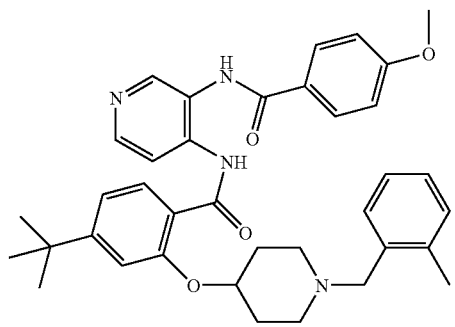

Using methods substantially equivalent to those described in Example 10, N$^4$-[4-tert-butyl-2-[1-(2-methylbenzyl)piperidin-4-yloxy]benzoyl]-N$^3$-(4-methoxybenzoyl)-3,4-diaminopyridine (40.1 mg, 87%) was prepared from N$^4$-[4-tert-butyl-2-(piperidin-4-yloxy)benzoyl]-N$^3$-(4-methoxybenzoyl)-3,4-diaminopyridine and 2-methylbenzaldehyde.

IS-MS, m/z 607.7 (m+1), 605.6 (M−1)−.

EXAMPLE 14

Preparation of N$^4$-[4-tert-Butyl-2-[1-(thiophen-2-ylmethyl)piperidin-4-yloxy]-benzoyl]-N$^3$-(4-methoxybenzoyl)-3,4-pyridinediamine

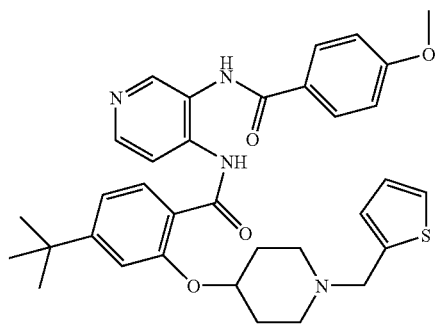

Using methods substantially equivalent to those described in Example 10, N$^4$-[4-tert-butyl-2-[1-(thiophen-2-ylmethyl)piperidin-4-yloxy]benzoyl]-N$^3$-(4-methoxybenzoyl)-3,4-pyridinediamine (45.9 mg, 101%) was prepared from N$^3$-(4-methoxybenzoyl)-N$^4$-[4-tert-butyl-2-(piperidin-4-yloxy)benzoyl]-3,4-pyridinediamine and thiophene 2-carboxaldehyde.

IS-MS, m/z 599.7 (m+1), 597.6 (M−1)−.

EXAMPLE 15

Preparation of N⁴-[4-tert-Butyl-2-[1-(thiophen-3-ylmethyl)piperidin-4-yloxy]-benzoyl]-N³-(4-methoxybenzoyl)-3,4-pyridinediamine

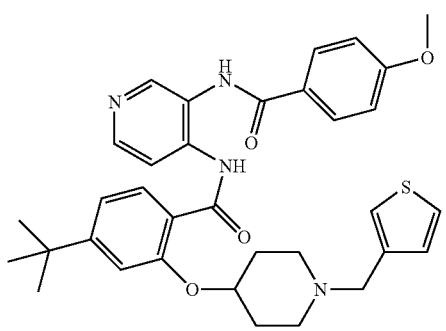

Using methods substantially equivalent to those described in Example 10, N⁴-[4-tert-butyl-2-[1-(thiophen-3-ylmethyl)piperidin-4-yloxy]benzoyl]-N³-(4-methoxybenzoyl)-3,4-pyridinediamine (46.2 mg, 102%) was prepared from N⁴-[4-tert-butyl-2-(piperidin-4-yloxy)benzoyl]-N³-(4-methoxybenzoyl)-3,4-diaminopyridine and thiophene 3-carboxaldehyde.

IS-MS, m/z 599.3 (m+1), 597.7 (M−1)−.

EXAMPLE 16

Preparation of N⁴-[4-tert-Butyl-2-[1-(cyclopropylmethyl)piperidin-4-yloxy]benzoyl]-N³-(4-methoxybenzoyl)-3,4-pyridinediamine

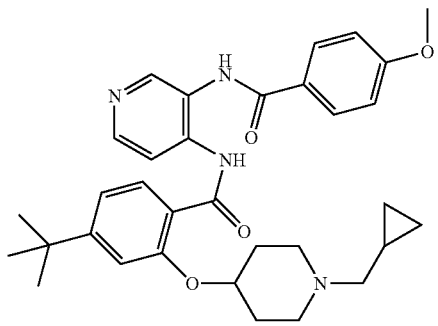

Using methods substantially equivalent to those described in Example 10, N⁴-[4-tert-butyl-2-[1-(cyclopropylmethyl)piperidin-4-yloxy]benzoyl]-N³-(4-methoxybenzoyl)-3,4-pyridinediamine (36.0 mg, 85%) was prepared from N⁴-[4-tert-butyl-2-(piperidin-4-yloxy)benzoyl]-N³-(4-methoxybenzoyl)-3,4-pyridinediamine and cyclopropanecarboxaldehyde.

IS-MS, m/z 557.2 (m+1), 555.3 (M−1)−.

EXAMPLE 17

Preparation of N⁴-[4-tert-Butyl-2-[1-(2,6-dimethoxybenzyl)piperidin-4-yloxy]-benzoyl]-N³-(4-methoxybenzoyl)-3,4-pyridinediamine

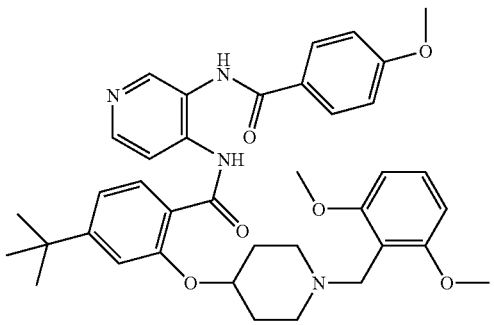

Using methods substantially equivalent to those described in Example 10, N⁴-[4-tert-butyl-2-[1-(2,6-dimethoxybenzyl)piperidin-4-yloxy]benzoyl]-N³-(4-methoxybenzoyl)-3,4-pyridinediamine (50.1 mg, 101%) was prepared from N⁴-[4-tert-butyl-2-(piperidin-4-yloxy)benzoyl]-N³-(4-methoxybenzoyl)-3,4-pyridinediamine and 2,6-dimethoxybenzaldehyde.

IS-MS, m/z 653.4 (m+1), 651.7 (M−1)−.

TABLE 1

Compounds of formula I which may be denoted by the following formula I-1

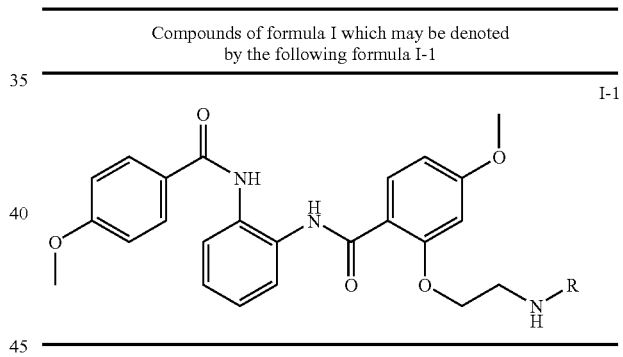

I-1 in which R has the indicated value were prepared according to the indicated procedure from a requisite corresponding compound of formula I or formula II and the reagents and conditions appropriate for the indicated procedure or by a procedure otherwise noted.

EXAMPLE 101

R=BOC: N¹-[2-[2-(tert-Butoxycarbonylamino)ethoxy]-4-methoxybenzoyl]-N²-(4-methoxybenzoyl)-1,2-benzenediamine A. 2-Bromo-N-(tert-butoxycarbonyl)ethylamine Using the procedure of V. G. Beylin and O. P. Goel, *OPPI Briefs*, 19, 78-80 (1987), 2-bromoethylamine hydrobromide (100 g, 488 mmol) was stirred with 250 ml water in a 3 liter roundbottom flask, then a solution of di-tert-butyl dicarbonate (54.28 g, 249 mmol) in 600 ml dichloromethane was added. To the resulting two-phase mixture was then added a solution of NaOH (39.04 g, 976 mmol, in 250 ml water) and the mixture was stirred vigorously for 3 h at room temperature. The organic layer was removed and washed once with water, with 0.2 N HCl until the pH of the aqueous layer reached 1, and again with water until the pH of the water reached 6-7. The organic layer was dried over $Na_2SO_4$ and concentrated in vacuo to provide the title compound (52.97 g, 95%) as a clear, nearly colorless oil.

IR (KBr): 1759, 1711 $cm^{-1}$
$^1$NMR (300 MHz, DMSO-$d_6$:
FAB-MS m/z 224.1, 226.1 (M+H)+
Analysis for $C_7H_{14}BrNO_2$:
Calcd: C, 37.52; H, 6.30; N, 6.25.
Found: C, 35.53; H, 6.07; N, 7.28.

B. Methyl 2-[2-(tert-butoxycarbonylamino)ethoxy]-4-methoxybenzoate

Methyl 4-methoxysalicylate (7.05 g, 38.7 mmol) and anhydrous potassium carbonate (16.03 g, 116 mmol) were stirred together in 30 ml dimethylformamide (DMF) for a few minutes at room temperature. To the stirring mixture was added 2-bromo-N-(tert-butoxycarbonyl)ethylamine (26.0 g, 116 mmol) in 30 ml DMF and 500 mg of freshly ground potassium iodide, then the mixture was placed under nitrogen and stirred at room temperature for several days. The reaction mixture was diluted with water (250 ml) and extracted with two 250 ml portions of dichloromethane. The organic extracts were pooled, washed (twice each with 1 N NaOH, water, and brine), then dried over $Na_2SO_4$ and concentrated in vacuo to afford a colorless oil. The oil was purified on a 1200 ml silica column packed and eluted with 95:5 $CH_2Cl_2$:EtOAc to yield methyl 2-[2-(tert-butoxycarbonylamino)ethoxy]-4-methoxybenzoate (10.29 g, 81%) as a viscous colorless oil.

IR (KBr): 1705, 1610 $cm^{-1}$
$^1$NMR (300 MHz, DMSO-$d_6$):
FAB-MS m/z 326.1 (M+H)+
Analysis for $C_{16}H_{23}NO_6$:
Calcd: C, 59.07; H, 7.13; N, 4.31.
Found: C, 58.36; H, 7.31; N, 5.81.

C. 2-[2-(tert-Butoxycarbonylamino)ethoxy]-4-methoxybenzoic acid

Methyl 2-[2-(tert-butoxycarbonylamino)ethoxy]-4-methoxybenzoate (1.0 g, 3.07 mmol) was suspended in 20 ml of 3:1 tetrahydrofuran (THF):water, then chilled on ice for 30 min with stirring. Next there was added solid lithium hydroxide monohydrate (284 mg, 6.76 mmol) to the suspension, and the mixture was stirred at room temperature for 20 h at which time TLC (50:50:1 hexanes:EtOAc:AcOH) showed complete consumption of starting ester. The slurry was diluted with water (50 ml), washed twice with ethyl ether, then the aqueous layer was acidified to pH 2 with 1 N $NaHSO_4$ to yield a heavy white slurry. The slurry was extracted twice with EtOAc, then the EtOAc layers were combined, washed with brine, dried over $Na_2SO_4$, and concentrated in vacuo to provide 2-[2-(tert-butoxycarbonylamino)ethoxy]-4-methoxybenzoic acid (870 mg, 91%) as a white crystalline solid.

IR (KBr): 1718, 1690 $cm^{-1}$
$^1$NMR (300 MHz, DMSO-$d_6$):
FAB-MS m/z 312.2 (M+H)+
Analysis for $C_{15}H_{21}NO_6$:
Calcd: C, 57.87; H, 6.80; N, 4.50.
Found: C, 58.13; H, 6.81; N, 4.56.

D. $N^1$-[2-[2-(tert-Butoxycarbonylamino)ethoxy]-4-methoxybenzoyl]-$N^2$-(4-methoxybenzoyl)-1,2-benzenediamine 2-[2-(tert-Butoxycarbonylamino)ethoxy]-4-methoxybenzoic acid (187 mg, 600 µmol) was suspended in 3.5 ml of $CH_2Cl_2$ under nitrogen, then 50 µl DMF was mixed in, followed by oxalyl chloride (63 µl, 720 µmol, 1.2 equivalents). Significant evolution of gas was observed upon oxalyl chloride addition. The clear solution was stirred at room temperature a few minutes, transferred to a 50 ml flask containing 5 ml toluene and stripped of volatiles on a rotary evaporator. The cloudy oil was resuspended in 5 ml of toluene and stripped again of volatiles to provide a cloudy oil. The oil was suspended in 10 ml of amylene-stabilized $CHCl_3$ and added to a chilled suspension of $N^1$-(4-methoxybenzoyl)-1,2-benzenediamine (122 mg, 500 µmol, 0.8 equivalents) also in 10 ml of amylene-stabilized $CHCl_3$. Next was added 200 µl of pyridine (2.47 mmol, 4 equivalents) to the mixture, and it was stirred on ice under a blanket of nitrogen. The slurry cleared to give a pale yellow solution within 10-15 min after pyridine addition. Stirring was continued on ice overnight, then at room temperature for a few hours. The clear mixture was diluted with 30 ml $CH_2Cl_2$ and washed once each with dilute $NaHSO_4$ and water. The organic layer was dried over $Na_2SO_4$ and concentrated to give a brown oil that was subsequently purified on a 2 mm thick chromatotron rotor using 1:1 hexanes:EtOAc as eluent. There was obtained $N^1$-[2-[2-(tert-butoxycarbonylamino)ethoxy]-4-methoxybenzoyl]-$N^2$-(4-methoxybenzoyl)-1,2-benzenediamine (201 mg, 62%) as a brittle off-white foam after drying the pure fractions from the chromatotron plate.

IR (KBr): 1712, 1607 $cm^{-1}$
$^1$NMR (300 MHz, DMSO-$d_6$):
FAB-MS m/z 536.4 (M+H)+, 436.3 (Des-Boc MH+).
Analysis for $C_{29}H_{33}N_3O_7$:
Calcd: C, 65.03; H, 6.21; N, 7.84.
Found: C, 64.73; H, 6.16; N, 7.66.

EXAMPLE 102

R=H:

A. Trifluoroacetate Salt.

$N^1$-[2-[2-(tert-Butoxycarbonylamino)ethoxy]-4-methoxybenzoyl]-$N^2$-(4-methoxybenzoyl)-1,2-benzenediamine (124 mg, 231 µmol) was dissolved in 3 ml of neat trifluoroacetic acid (TFA) in a capped vial for 90 min at room temperature. The volatiles were removed in vacuo and the residue was resuspended in a few ml of toluene and re-evaporated. This step was repeated twice more with toluene and once with dichloromethane. The resulting white solid was dried under high vacuum to give 113 mg (89%) of $N^1$-[2-(2-aminoethoxy)-4-methoxybenzoyl]-$N^2$-(4-methoxybenzoyl)-1,2-benzenediamine trifluoroacetate as a solid white film.

$^1$NMR (300 MHz, DMSO-$d_6$):
FAB-MS m/z 436.3 (M+H)+.

B. Free Base.

The free base form of $N^1$-[2-(2-aminoethoxy)-4-methoxybenzoyl]-$N^2$-(4-methoxybenzoyl)-1,2-benzenediamine was prepared by vigorously stirring $N^1$-[2-(2-aminoethoxy)-4-methoxybenzoyl]-$N^2$-(4-methoxybenzoyl)-1,2-benzenediamine trifluoroacetate (1.88 g, 3.42 mmol) with 100 ml water, 2 grams potassium carbonate and 100 ml of $CH_2Cl_2$ for several hours at room temperature. After stirring, the organic layer was set aside and combined with a 150 ml $CH_2Cl_2$ wash of the original aqueous layer. The combined $CH_2Cl_2$ extracts were washed with brine, dried over $Na_2SO_4$, concentrated in vacuo, then purified on a chromatotron system (4 mm plate) with 9:1 $CH_2Cl_2$:MeOH eluent to provide $N^1$-[2-(2-aminoethoxy)-4-methoxybenzoyl]-$N^2$-(4-methoxybenzoyl)-1,2-benzenediamine (1.26 g, 85%) as a brittle white foam after high vacuum drying.

General Procedure A for Acylation of Amines:

Fifty to ninety micromoles (27-50 mg) of $N^1$-[2-(2-aminoethoxy)-4-methoxybenzoyl]-$N^2$-(4-methoxybenzoyl)-1,2-benzenediamine trifluoroacetate was placed in a 4 ml screw-cap vial and suspended in 1.5 ml amylene stabilized chloroform with at least 2 equivalents of piperidinomethylpolystyrene (Fluka). Next was added 1.3 to 1.5 equivalents of an acylating agent such as an acid chloride, acid anhydride, carbamoyl chloride, chloroformate, isocyanate, isothiocyanate or sulfonyl chloride. The vial was capped, shaken overnight at room temperature on an orbital platform shaker at 300-350 rpm, then excess acylating agent was scavenged by adding aminomethylated polystyrene (100 mg or 225 micromoles amine function) and another 1 ml of amylene-stabilized $CHCl_3$. The resulting slurry was mixed overnight as above on an orbital platform shaker, then filtered through a disposable tube containing a porous frit. The retentate was rinsed with another 1-2 ml of the $CHCl_3$, and the combined filtrates were concentrated by evaporation to afford clean product. Alternatively, the piperidinomethylpolystyrene can be omitted if the $N^1$-[2-(2-aminoethoxy)-4-methoxybenzoyl]-$N^2$-(4-methoxybenzoyl)-1,2-benzenediamine free base is used instead of the trifluoroacetate salt, except for reagents which generate acid on reaction (e.g. acid chlorides, sulfonyl chlorides) where the piperidinomethylpolystyrene is necessary to scavenge the acid produced from the acylation reaction.

EXAMPLE 103

R=Methylaminocarbonyl: Procedure A; ES-MS m/z 493.2 (M+H)+

EXAMPLE 104

R=Isopropyl:

In a 4 ml screw-cap vial were combined a solution of $N^1$-[2-(2-aminoethoxy)-4-methoxybenzoyl]-$N^2$-(4-methoxybenzoyl)-1,2-benzenediamine trifluoroacetate (45-50 μmol, 25 mg, in 400 μl 95:5 anhydrous MeOH:AcOH) with acetone (10 μl, 7.9 mg, 136 μmol). Next was added 544 μl freshly prepared $NaCNBH_3$ solution (0.25 M in anhydrous MeOH). Significant evolution of gas was noted. The vial was capped, shaken overnight at room temperature on an orbital platform shaker. The crude reaction mixture was applied to a 500 mg strong cation exchange (SCX) cartridge (Varian Sample Preparation Products) that was pre-washed with MeOH. After sample application, the SCX cartridge was washed 3-5 times with 2-5 ml of 1:1 MeOH:$CH_2Cl_2$, 3 times with 5 ml MeOH, then eluted twice with 5 ml portions of 0.5 N $NH_3$ in MeOH. Evaporation of the $NH_3$-MeOH yielded clean product. ES-MS m/z 478.2 (M+H)+.

EXAMPLE 105

R=Acetyl: Procedure A, using 1.5 equivalent acetic anhydride instead of an isocyanate or isothiocyanate; ES-MS m/z 478.2 (M+H)+.

EXAMPLE 106

R=Ethylaminocarbonyl: Procedure A; ES-MS m/z 507.2 (M+H)+.

EXAMPLE 107

R=Butylaminocarbonyl: Procedure A; ES-MS m/z 535.2 (M+H)+.

EXAMPLE 108

R=Isopropylaminocarbonyl: Procedure A; ES-MS m/z 521.1 (M+H)+.

EXAMPLE 109

R=Cyclohexylaminocarbonyl: Procedure A; ES-MS m/z 561.4 (M+H)+.

EXAMPLE 110

R=Phenylaminocarbonyl: Procedure A; ES-MS m/z 555.2 (M+H)+.

EXAMPLE 111

R=(2-Fluorophenyl)aminocarbonyl: Procedure A.

EXAMPLE 112

R=[2-(Ethoxycarbonyl)ethyl]aminocarbonyl: Procedure A; ES-MS m/z 579.2 (M+H)+.

EXAMPLE 113

R=[3-(Dimethylamino)propyl]aminothiocarbonyl: Procedure A; ES-MS m/z 580 (M+H)+.

EXAMPLE 114

R=2-Thienylcarbonyl: Procedure A; ES-MS m/z 546.2 (M+H)+.

EXAMPLE 115

R=4-Morpholinylcarbonyl: Procedure A; ES-MS m/z 549.2 (M+H)+.

EXAMPLE 116

R=(2-Methoxyethoxy)carbonyl: Procedure A; ES-MS m/z 537.8 (M+H)+.

EXAMPLE 117

R=3-Carboxy-1-oxopropyl: Procedure A; ES-MS m/z 535.8 (M+H)+.

General Procedure D for Acylation of Amine Compounds Such as Those Described in Example 102:

To $N^1$-[2-(2-aminoethoxy)-4-methoxybenzoyl]-$N^2$-(4-methoxybenzoyl)-1,2-benzenediamine (60 μmol) in a 4 ml screw cap vial was added polymer-supported carbodiimide (280-380 mg @ 0.85 mmol/g, 4-6 equivalents) and a carboxylic acid of choice (120 μmol, 2 equivalents), followed by 3 ml of 4:1 amylene-stabilized $CHCl_3$:tert-butyl alcohol. Where acid hydrochloride salts were used, piperidinomethylpolystyrene resin (100 mg @ 2.6-2.8 mmol/g) was also added to the vial. The vial was capped, shaken overnight at room temperature, then the mixture was filtered. Retentates were washed with 3 ml of amylene-stabilized chloroform, and the combined filtrate and wash were concentrated in vacuo to afford the amide derivative.

EXAMPLE 118

R=(S)-2,6-bis(BOC-amino)-1-oxohexyl[$N^2,N^6$-Di-BOC-L-lysyl]: Procedure D; ES-MS m/z 945.6 (M+H)+ for the dicyclohexylamine salt form.

EXAMPLE 119

R=3-(4-Morpholinyl)-1-oxopropyl: Procedure D; ES-MS m/z 577.4 (M+H)+.

EXAMPLE 120

R=Dimethylaminoacetyl: Procedure D; ES-MS m/z 521.2 (M+H)+.

EXAMPLE 121

R=(S)-1-Methylpyrrolidin-2-ylcarbonyl[1-Methyl-L-prolyl]: Procedure D; ES-MS m/z 547.2 (M+H)+.

EXAMPLE 122

R=(S)-2-(BOC-Amino)-1-oxopropyl[N—BOC-L-Alanyl]: Procedure D; ES-MS m/z 607.2 (M+H)+.

EXAMPLE 123

R=2-(2-Methoxyethoxy)ethoxyacetyl: Procedure D; ES-MS m/z 596.2 (M+H)+.

EXAMPLE 124

R=(S)-2-(BOC-Amino)-3-hydroxy-1-oxopropyl[N—BOC-L-Seryl]: Procedure D; ES-MS m/z 623.4 (M+H)+.

EXAMPLE 125

R=(R)-3-BOC-thiazolidin-4-ylcarbonyl: Procedure D; ES-MS m/z 651.2 (M+H)+.

EXAMPLE 126

R=(S)-5-Oxopyrrolidin-2-ylcarbonyl[L-Pyroglutamyl]: Procedure D; ES-MS m/z 547.4 (M+H)+.

EXAMPLE 127

R=(S)-2-(BOC-Amino)-4-methylthio-1-oxobutyl[N—BOC-L-methionyl]: Procedure D; ES-MS m/z 667.2 (M+H)+.

EXAMPLE 128

R=(S)-2-(BOC-Amino)-4-methylsulfinyl-1-oxobutyl [N—BOC—S-Oxo-L-methionyl]: Procedure D; ES-MS m/z 683.0 (M+H)+.

EXAMPLE 129

R=(2S,3R)-2-(BOC-Amino)-3-t-butoxy-1-oxobutyl [N—BOC—O-t-Butyl-L-threonyl]: Procedure D; ES-MS m/z 693.0 (M+H)+.

EXAMPLE 130

R=(S)-2-(BOC-Amino)-3-(benzyloxycarbonyl)-1-oxopropyl [N—BOC-β-Benzyl-L-α-aspartyl]: Procedure D; FIA-MS m/z 758.2 (M+NH$_3^+$), 741.3 (M+H)+.

EXAMPLE 131

R=(2S,3S)-2-(BOC-Amino)-3-methyl-1-oxopentyl [N—BOC-L-Isoleucyl]: Procedure D; FIA-MS m/z 666.2 (M+NH$_3^+$), 649.3 (M+H)+.

EXAMPLE 132

R=(S)-2-(BOC-Amino)-4-methyl-1-oxopentyl[N—BOC-L-Leucyl]: Procedure D; FIA-MS m/z 666.2 (M+NH$_3^+$), 649.3 (M+H)+.

EXAMPLE 133

R=(S)-2-(BOC-Amino)-3-methyl-1-oxobutyl[N—BOC-L-Valyl]: Procedure D; FIA-MS m/z 710.2 (M+NH$_3^+$), 635.4 (M+H)+.

EXAMPLE 134

R=Allyloxycarbonyl: Procedure A; FIA-MS m/z 520.0 (M+H)+.

EXAMPLE 135

R=4-Cyclohexyl-1-oxobutyl: Procedure D; FIA-MS m/z 605.2 (M+NH$_3^+$), 588.2 (M+H)+.

EXAMPLE 136

R=3-Thienylcarbonyl: Procedure D; FIA-MS m/z 562.2 (M+NH$_3^+$), 546.1 (M+H)+.

EXAMPLE 137

R=4-t-Butylcyclohexylcarbonyl: Procedure D; FIA-MS m/z 619.4 (M+NH$_3^+$), 602.3 (M+H)+.

EXAMPLE 138

R=3-Methyl-1-oxobutyl; Procedure D: FIA-MS m/z 537.2 (M+NH$_3^+$), 520.3 (M+H)+.

EXAMPLE 139

R=3-Cyclohexyl-1-oxopropyl: Procedure D; FIA-MS m/z 591.4 (M+NH$_3^+$), 574.2 (M+H)+.

EXAMPLE 140

R=4-Methyl-1-oxopentyl: Procedure D; FIA-MS m/z 551.2 (M+NH$_3^+$), 534.1 (M+H)+.

EXAMPLE 141

R=2,2-Dimethyl-5-oxotetrahydrofuran-3-ylcarbonyl: Procedure D; FIA-MS m/z 576.0 (M+H)+.

EXAMPLE 142

R=Cyclohexylacetyl: Procedure D; FIA-MS m/z 577.2 (M+NH$_3^+$), 560.3 (M+H)+.

EXAMPLE 143

R=(1R,2S,5R)-2-Methyl-5-isopropylcyclohexyloxycarbonyl [(−)-Menthyloxycarbonyl]: Procedure A; FIA-MS m/z 635.2 (M+NH$_3^+$), 618.2 (M+H)+.

EXAMPLE 144

R=(S)-1-Ethoxycarbonyl-3-methylbutylaminocarbonyl: Procedure A; FIA-MS m/z 638.0 (M+NH$_3^+$), 621.1 (M+H)+.

EXAMPLE 145

R=2-Adamantylcarbonyl: Procedure A; FIA-MS m/z 615.2 (M+NH$_3^+$), 598.3 (M+H)+.

EXAMPLE 146

R=3,3-Dimethyl-1-oxobutyl: Procedure A; FIA-MS m/z 551.2 (M+NH$_3^+$), 534.1 (M+H)+.

EXAMPLE 147

R=(S)-1-Ethoxycarbonyl-2-methylpropylaminocarbonyl: Procedure A; FIA-MS m/z 624.1 (M+NH$_3^+$), 607.2 (M+H)+.

EXAMPLE 148

R=2-Methylcyclopropylcarbonyl: Procedure D; FIA-MS m/z 535.2 (M+NH$_3^+$), 518.1 (M+H)+.

EXAMPLE 149

R=trans-2-Phenylcyclopropylcarbonyl: Procedure D; FIA-MS m/z 597.2 (M+NH$_3^+$), 580.3 (M+H)+.

EXAMPLE 150

R=2-Adamantylaminocarbonyl; Procedure A; FIA-MS m/z 613.2 (M+H)+.

EXAMPLE 151

R=Benzyloxycarbonyl; Procedure A; FIA-MS m/z 570.2 (M+H)+.

TABLE 2

Compounds of formula I which may be denoted by the following formula I-2

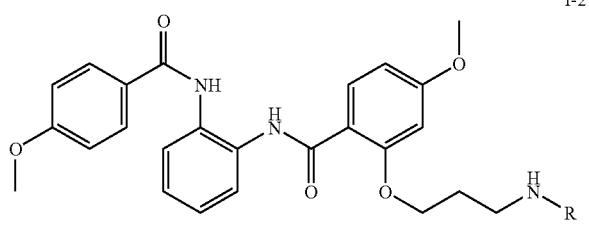

I-2 in which R has the indicated value were prepared according to the indicated procedure from a requisite corresponding compound of formula I or formula II and the reagents and conditions appropriate for the indicated procedure or by a procedure otherwise noted.

EXAMPLE 201

R=BOC: N$^1$-[2-[3-(tert-Butoxycarbonylamino)propoxy]-4-methoxybenzoyl]-N$^2$-(4-methoxybenzoyl)-1,2-benzenediamine.

A. 3-Bromo-N-(tert-butoxycarbonyl)propylamine

In a manner substantially equivalent to Example 101-A, 3-bromo-N-(tert-butoxycarbonyl)propylamine was prepared from 3-bromopropylamine hydrobromide and di-tert-butyl dicarbonate.

IR (KBr): 1709, 1507 cm$^{-1}$
$^1$NMR (300 MHz, DMSO-d$_6$):
FAB-MS, m/z 238.0, 240.0 (M+H)+
Analysis for C$_8$H$_{16}$BrNO$_2$:
Calcd: C, 40.35; H, 6.77; N, 5.88.
Found: C, 40.12; H, 6.62; N, 6.06.

B. Methyl 2-[3-(tert-butoxycarbonylamino)propoxy]-4-methoxybenzoate

In a manner substantially equivalent to Example 101-B, methyl 2-[3-(tert-butoxycarbonylamino)propoxy]-4-methoxybenzoate was prepared from 3-bromo-N-(tert-butoxycarbonyl)propylamine and methyl 4-methoxysalicylate.

IR (KBr): 1698, 1611, 1577, 1505 cm$^{-1}$
$^1$NMR (300 MHz, DMSO-d$_6$):
FAB-MS, m/z 340.2 (M+H)+, 240.2 (MH+ of des-Boc fragment)
Analysis for C$_{17}$H$_{25}$NO$_6$:
Calcd: C, 60.16; H, 7.43; N, 4.13.
Found: C, 59.92; H, 7.42; N, 4.18.

C. 2-[3-(tert-Butoxycarbonylamino)propoxy]-4-methoxybenzoic acid

In a manner substantially equivalent to Example 101-C, 2-[3-(tert-butoxycarbonylamino)propoxy]-4-methoxybenzoic acid was prepared from methyl 2-[3-(tert-butoxycarbonylamino)propoxy]-4-methoxybenzoate.

IR (KBr): 1686, 1663, 1610 cm$^1$
$^1$NMR (300 MHz, DMSO-d$_6$):
FAB-MS, m/z 326.2 (M+H)+, 226.2 (MH+ of des-Boc fragment)
Analysis for C$_{16}$H$_{23}$NO$_6$:
Calcd: C, 59.07; H, 7.13; N, 4.31.
Found: C, 58.99; H, 7.17; N, 4.40.

D. N$^1$-[2-[3-(tert-Butoxycarbonylamino)propoxy)-4-methoxybenzoyl]-N$^2$-(4-methoxybenzoyl)-1,2-benzenediamine In a manner substantially equivalent to example 101-D, N$^1$-[2-[3-(tert-butoxycarbonylamino)propoxy)-4-methoxybenzoyl]-N$^2$-(4-methoxybenzoyl)-1,2-benzenediamine was prepared from 2-[3-(tert-butoxycarbonylamino)propoxy]-4-methoxybenzoic acid and N$^1$-(4-methoxybenzoyl)-1,2-benzenediamine.

IR (KBr): 1734, 1692, 1657, 1610 cm$^{-1}$
$^1$NMR (300 MHz, DMSO-d$_6$):
FAB-MS, m/z 550.3 (M+H)+, 450.3 (Des-Boc MH+).
Analysis for C$_{30}$H$_{35}$N$_3$O$_7$:
Calcd: C, 65.56; H, 6.42; N, 7.64.
Found: C, 65.14; H, 6.84; N, 7.07.

EXAMPLE 202

R=H (trifluoroacetate salt): Procedure substantially equivalent to that of Example 102. NMR (300 MHz DMSO); ES-MS m/z 450.3 (M+H)+.

EXAMPLE 203

R=3-Carboxy-1-oxopropyl: Procedure A; ES-MS m/z 549.8 (M+H)+.

EXAMPLE 204

R=Methylaminocarbonyl: Procedure A; ES-MS m/z 507.2 (M+H)+.

EXAMPLE 205

R=Isopropyl: Procedure substantially equivalent to that of Example 104 above; ES-MS m/z 492.4 (M+H)+.

EXAMPLE 206

R=2-Amino-2-oxoethyl: Procedure A; ES-MS m/z 507.0 (M+H)+.

EXAMPLE 207

R=Acetyl: Procedure A; ES-MS m/z 492.0 (M+H)+.

EXAMPLE 208

R=3-(4-Morpholinyl)-1-oxopropyl: Procedure D; ES-MS m/z 591.0 (M+H)+.

EXAMPLE 209

R=(S)-2-(BOC-Amino)-1-oxopropyl[N—BOC-L-Alanyl]: Procedure D; ES-MS m/z 621.2 (M+H)+.

EXAMPLE 210

R=2-(2-Methoxyethoxy)ethoxyacetyl; Procedure D; ES-MS m/z 610.0 (M+H)+, 632.2 (MNa+).

EXAMPLE 211

R=(S)-2-(BOC-Amino)-3-hydroxy-1-oxopropyl[N—BOC-L-Seryl]: Procedure D.

EXAMPLE 212

R=(R)-3-BOC-thiazolidin-4-ylcarbonyl: Procedure D; ES-MS m/z 665.0 (M+H)+.

EXAMPLE 213

R=(S)-5-Oxopyrrolidin-2-ylcarbonyl[L-Pyroglutamyl]: Procedure D; ES-MS m/z 561.4 (M+H)+.

EXAMPLE 214

R=(S)-2-(BOC-Amino)-4-methylthio-1-oxobutyl[N—BOC-L-methionyl]: Procedure D; ES-MS m/z 681.2 (M+H)+.

EXAMPLE 215

R=(S)-2-(BOC-Amino)-4-methylsulfinyl-1-oxobutyl [N—BOC—S-Oxo-L-methionyl]: Procedure D; ES-MS m/z 697.2 (M+H)+.

EXAMPLE 216

R=(2S,3R)-2-(BOC-Amino)-3-t-butoxy-1-oxobutyl [N—BOC—O-t-Butyl-L-threonyl]: Procedure D; ES-MS m/z 707.6 (M+H)+.

EXAMPLE 217

R=Ethylaminocarbonyl: Procedure A; ES-MS m/z 521.0 (M+H)+.

EXAMPLE 218

R=Butylaminocarbonyl: Procedure A; ES-MS m/z 548.8 (M+H)+.

EXAMPLE 219

R=Isopropylaminocarbonyl: Procedure A; ES-MS m/z 535.4 (M+H)+.

EXAMPLE 220

R=Cyclohexylaminocarbonyl: Procedure A; ES-MS m/z 575.2 (M+H)+.

EXAMPLE 221

R=Phenylaminocarbonyl: Procedure A; ES-MS m/z 569.4 (M+H)+.

EXAMPLE 222

R=(2-Fluorophenyl)aminocarbonyl: Procedure A; ES-MS m/z 587.4 (M+H)+.

EXAMPLE 223

R=[2-(Ethoxycarbonyl)ethyl]aminocarbonyl: Procedure A; ES-MS 593.2 (M+H)+.

EXAMPLE 224

R=2-Thienylcarbonyl: Procedure A; ES-MS m/z 560.2 (M+H)+.

EXAMPLE 225

R=4-Morpholinylcarbonyl: Procedure A; ES-MS m/z 563.2 (M+H)+.

EXAMPLE 226

R=2-Methylfuran-3-ylcarbonyl: Procedure D; FIA-MS m/z 558.2 (M+H)+.

EXAMPLE 227

R=3-Thienylcarbonyl: Procedure D; FIA-MS m/z 560.2 (M+H)+.

EXAMPLE 228

R=(3-Thienyl)acetyl: Procedure D; FIA-MS m/z 574.2 (M+H)+.

EXAMPLE 229

R=5-Chlorofuran-2-ylcarbonyl: Procedure D; FIA-MS m/z 578.0/579 (M+H)+.

EXAMPLE 230

R=4-t-Butylcyclohexylcarbonyl: Procedure D; FIA-MS m/z 616.4 (M+H)+.

EXAMPLE 231

R=5-Methylfuran-3-ylcarbonyl: Procedure D; FIA-MS m/z 558.2 (M+H)+.

EXAMPLE 232

R=3-(2-Pyridinyl)-1-oxopropyl: Procedure D; FIA-MS m/z 583.0 (M+H)+.

EXAMPLE 233

R=4,5-Dimethyluran-2-ylcarbonyl: Procedure D; FIA-MS m/z 572.0 (M+H)+.

EXAMPLE 234

R=(2-Thienyl)acetyl: Procedure D; FIA-MS m/z 574.2 (M+H)+.

EXAMPLE 235

R=2-(2-Thienyl)-2-oxoacetyl: Procedure D; FIA-MS m/z 588.0 (M+H)+.

EXAMPLE 236

R=5-Bromofuran-2-ylcarbonyl: Procedure D; FIA-MS m/z 622.2 (M−1)−.

EXAMPLE 237

R=1-Methylpyrrol-2-ylcarbonyl: Procedure D; FIA-MS m/z 557.0 (M+H)+.

EXAMPLE 238

R=4-Chlorofuran-2-ylcarbonyl: Procedure D; FIA-MS m/z 578.0 (M+H)+.

EXAMPLE 239

R=2,5-Dimethyl-2H-pyrazol-3-ylcarbonyl: Procedure D; FIA-MS m/z 572.2 (M+H)+.

EXAMPLE 240

R=3-Methylfuran-2-ylcarbonyl: Procedure D; FIA-MS m/z 558.2 (M+H)+.

EXAMPLE 241

R=4-Cyanophenylsulfonyl: Procedure A; FIA-MS m/z 615.0 (M+H)+.

EXAMPLE 242

R=2-Thienylsulfonyl: Procedure A; FIA-MS m/z 569.2 (M+H)+.

EXAMPLE 243

R=2-Methoxycarbonylthien-3-ylsulfonyl: Procedure A; FIA-MS m/z 654.0 (M+H)+.

EXAMPLE 244

R=Benzoyl: Procedure D; FIA-MS m/z 555.0 (M+H)+, 553.2 (M−1)−.

EXAMPLE 245

R=3-Furanylcarbonyl: Procedure D; FIA-MS m/z 544.2 (M+H)+, 542.2 (M−1)−.

EXAMPLE 246

R=5-Methylfuran-2-ylcarbonyl: Procedure D; FIA-MS m/z 558.2 (M+H)+, 556.1 (M−1)−.

EXAMPLE 247

R=2-Furanylcarbonyl: Procedure D; FIA-MS m/z 544.2 (M+H)+, 542.4 (M−1)−.

EXAMPLE 248

R=5-Methylsulfonylthien-2-ylcarbonyl: Procedure D; FIA-MS m/z 638.0 (M+H)+, 636.0 (M−1)−.

EXAMPLE 249

R=1-Methylpyrazol-4-ylcarbonyl: Procedure D; FIA-MS m/z 558.2 (M+H)+, 556.2 (M−1)−.

EXAMPLE 250

R=2-Methyl-2H-pyrazol-3-ylcarbonyl: Procedure D; FIA-MS m/z 558.0 (M+H)+, 556.2 (M−1)−.

EXAMPLE 251

R=5-Thiazolylcarbonyl: Procedure D; FIA-MS m/z 561.2 (M+H)+, 559.2 (M−1)−.

EXAMPLE 252

R=5-Chlorothien-2-ylcarbonyl: Procedure D; FIA-MS m/z 594.2 (M+H)+, 592.4 (M−1)−.

EXAMPLE 253

R=2,5-Dichlorothien-3-ylcarbonyl: Procedure D; FIA-MS m/z 628.0 (M+H)+.

EXAMPLE 254

R=5-Bromo-4-methylthien-2-ylcarbonyl: Procedure D; FIA-MS m/z 654.0 (M+H)+, 652.2 (M−1)−.

EXAMPLE 255

R=2,4-Dimethyluran-3-ylcarbonyl: Procedure D; FIA-MS m/z 572.2 (M+H)+, 570.4 (M−1)−.

EXAMPLE 256

R=2-Chlorothien-3-ylcarbonyl: Procedure D; FIA-MS m/z 594.2 (M+H)+, 592.4 (M−1)−.

EXAMPLE 257

R=4-Methylthien-2-ylcarbonyl: Procedure D; FIA-MS m/z 574.2 (M+H)+, 572.2 (M−1)−.

EXAMPLE 258

R=3-Methylthien-2-ylcarbonyl: Procedure D; FIA-MS m/z 574.2 (M+H)+, 572.2 (M−1)−.

EXAMPLE 259

R=5-Methylthien-2-ylcarbonyl: Procedure D; FIA-MS m/z 574.2 (M+H)+, 572.2 (M−1)−.

EXAMPLE 260

R=5-Methylisoxazol-3-ylcarbonyl: Procedure D; FIA-MS m/z 559.2 (M+H)+, 557.0 (M−1)−.

EXAMPLE 261

R=5-t-Butylfuran-2-ylcarbonyl: Procedure D; FIA-MS m/z 600.2 (M+H)+, 598.4 (M−1)−.

TABLE 3

Compounds of formula I which may be denoted by the following formula I-3

I-3

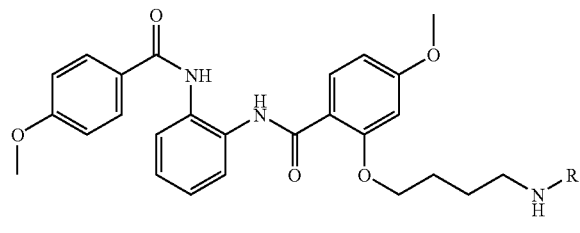

in which R has the indicated value were prepared according to the indicated procedure from a requisite corresponding compound of formula I or formula II and the reagents and conditions appropriate for the indicated procedure or by a procedure otherwise noted.

EXAMPLE 301

R=BOC: $N^1$-[2-[4-(tert-Butoxycarbonylamino)butoxy]-4-methoxybenzoyl]-$N^2$-(4-methoxybenzoyl)-1,2-benzenediamine.

A. Methyl 4-methoxy-2-(4-pthalimidobutoxy)benzoic acid

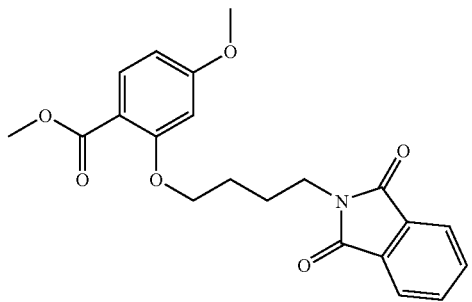

In a manner substantially equivalent to Example 101-B, methyl 4-methoxy-2-(4-pthalimidobutoxy)benzoic acid was prepared from methyl 4-methoxysalicylate (5.97 g, 30.4 mmol) and 4-bromobutylphthalimide (10.3 g, 36.5 mmol) to give, after recrystallization from hexane-ethyl acetate, a white solid (9.40 g, 80.3%).

$^1$H NMR (300 MHz, DMSO-$d_6$);

FAB MS m/z 384.1 (M+H)+;

Anal. for $C_{21}H_{21}NO_6$:

Calcd: C, 65.79; H, 5.52; N, 3.65.

Found: C, 66.04; H, 5.62; N, 3.66.

B. Methyl 2-[4-(tert-butoxycarbonylamino)butoxy]-4-methoxybenzoate

A suspension of methyl 4-methoxy-2-(4-pthalimidobutoxy)benzoic acid (9.35 g, 24.4 mmol) and hydrazine (73.2 ml, 1.0 M in MeOH) was stirred at room temperature under $N_2$ for 18 h. The thick slurry was diluted with MeOH (50 ml) and stirring continued for 8 h. The reaction mixture was diluted with dichloromethane (400 ml), chilled to 0° C., and filtered. The filtrate was concentrated in vacuo to give a white solid. The product was taken up again in dichloromethane and filtered. The filtrate was concentrated in vacuo to give 4.88 g of a viscous, yellow oil. The crude amine (4.88 g, 19.9 mmol) was dissolved in dioxane (35 ml). Sodium carbonate (2.10 g, 19.9 mmol) and water (40 ml) were added; and after a solution developed, di-tert-butyl dicarbonate (4.77 g, 21.9 mmol) and dioxane (15 ml) were added. The reaction mixture was stirred for 18 h at room temperature in a capped flask. The solvent volume was reduced to approximately one-half and the pH adjusted to 3 with 1 N $NaHSO_4$. EtOAc was added, and the reaction transferred to a separatory funnel. The layers were separated and the organic layer washed with brine, dried, and the solvent removed in vacuo to give a viscous yellow oil. Chromatography (silica, 4:1 to 2:1 hexane:EtOAc) yielded 5.66 g (67.2%) of a brittle, white solid.

C. 2-[4-(tert-Butoxycarbonylamino)butoxy]-4-methoxybenzoic acid

In a manner substantially equivalent to Example 101-C, methyl 2-[4-(tert-butoxycarbonylamino)butoxy]-4-methoxybenzoate (5.60 g, 16.2 mmol) yielded 2-[4-(tert-butoxycarbonylamino)butoxy]-4-methoxybenzoic acid (5.3 g, 96.4%) as a white solid.

D. $N^1$-[2-[4-(tert-Butoxycarbonylamino)butoxy]-4-methoxybenzoyl]-$N^2$-(4-methoxybenzoyl)-1,2-benzenediamine In a manner substantially equivalent to Example 101-D, $N^1$-[2-[4-(tert-butoxycarbonylamino)butoxy]-4-methoxybenzoyl]-$N^2$-(4-methoxybenzoyl)-1,2-benzenediamine was prepared from 2-[4-(tert-butoxycarbonylamino)butoxy]-4-methoxybenzoic acid (1.50 g, 4.42 mmol) and $N^1$-(4-methoxybenzoyl)-1,2-benzenediamine (1.07 g, 4.42 mmol) to give, after silica gel purification (100% hexane to 40:60 hexane:EtOAc), 1.72 g (69.1%) of a white foam.
$^1$H NMR (300 MHz, DMSO-$d_6$);
FD MS m/z 384.1 (M).

EXAMPLE 302

R=H: $N^1$-[2-(4-Aminobutoxy)-4-methoxybenzoyl]-$N^2$-(4-methoxybenzoyl)-1,2-benzenediamine.

In a manner substantially equivalent to Example 102, $N^1$-[2-(4-aminobutoxy)-4-methoxybenzoyl]-$N^2$-(4-methoxybenzoyl)-1,2-benzenediamine was prepared from $N^1$-[2-[4-(tert-butoxycarbonylamino)butoxy]-4-methoxybenzoyl]-$N^2$-(4-methoxybenzoyl)-1,2-benzenediamine (1.68 g, 2.98 mmol) to give 0.70 g (50.7%) of a white foam.
$^1$H NMR (300 MHz, DMSO-$d_6$);
FD MS m/z 464.1 (M+H)+.

EXAMPLE 303

R=4-Cyclohexyl-1-oxobutyl: Procedure D; FIA-MS m/z 616.2 (M+H)+.

EXAMPLE 304

R=3-Thienylcarbonyl: Procedure D; FIA-MS m/z 574.3 (M+H)+.

EXAMPLE 305

R=4-t-Butylcyclohexylcarbonyl: Procedure D; FIA-MS m/z 630.2 (M+H)+.

EXAMPLE 306

R=(2S,3R)-2-(BOC-Amino)-3-t-butoxy-1-oxobutyl [N—BOC—O-t-Butyl-L-threonyl]: Procedure D; FIA-MS m/z 721.2 (M+H)+.

EXAMPLE 307

R=4-Methyl-1-oxopentyl: Procedure D; FIA-MS m/z 562.2 (M+H)+.

EXAMPLE 308

R=trans-2-Phenylcyclopropylcarbonyl: Procedure D; FIA-MS m/z 608.0 (M+H)+.

EXAMPLE 309

R=(3-Thienyl)acetyl: Procedure D; FIA-MS m/z 588.0 (M+H)+.

EXAMPLE 310

R=Benzo[b]thien-2-yl: Procedure D; FIA-MS m/z 624.2 (M+H)+.

EXAMPLE 311

R=3-Pyridinylcarbonyl: Procedure D; FIA-MS m/z 569.2 (M+H)+, 567.4 (M−1)−.

EXAMPLE 312

R=2-Pyridinylcarbonyl: Procedure D; FIA-MS m/z 569.2 (M+H)+.

EXAMPLE 313

R=1-Methylpyrrol-2-ylcarbonyl: Procedure D; FIA-MS m/z 571.2 (M+H)+.

EXAMPLE 314

R=(2-Thienyl)acetyl: Procedure D; FIA-MS m/z 588.2 (M+H)+.

General Procedure C for Acylation of Amines Such as the Compound Described in Example 302

To the amine (59 µmol) in a 4 mL screw cap vial is added polymer-supported carbodiimide (P-EPC, 280 mg @ 0.85 mmol/g, 4 eq) and a carboxylic acid of choice (120 µmol, 2 eq), followed by 3 mL of 4:1 (amylene stabilized) chloroform:tert-butyl alcohol. Where acid hydrochloride salts are used, piperidinomethyl polystyrene resin (100 mg @ 2.6-2.8 mmol/g) is added to effect reaction. The vial is capped, shaken overnight at room temperature, then the mixture is filtered. Retentates are washed with amylene stabilized chloroform (3 mL), and the combined filtrate and wash are concentrated in vacuo to afford the amide derivative of the compound of Example 302.

EXAMPLE 315

R=2-Thienylcarbonyl: Procedure C; FIA-MS m/z 574.2 (M+H)+.

EXAMPLE 316

R=3,3-Dimethyl-1-oxobutyl: Procedure C; FIA-MS m/z 562.2 (M+H)+.

EXAMPLE 317

R=Allyloxycarbonyl: Procedure C; FIA-MS m/z 548.2 (M+H)+.

EXAMPLE 318

R=4-t-Butylbenzoyl: Procedure C; FIA-MS m/z 624.2 (M+H)+.

EXAMPLE 319

R=Pivaloyl: Procedure C; FIA-MS m/z 548.2 (M+H)+.

EXAMPLE 320

R=2-Adamantylcarbonyl: Procedure C; FIA-MS m/z 626.2 (M+H)+.

TABLE 4

Compounds of formula I which may be denoted by the following formula I-4

I-4 in which R has the indicated value were prepared according to the indicated procedure from a requisite corresponding compound of formula I or formula II and the reagents and conditions appropriate for the indicated procedure or by a procedure otherwise noted.

EXAMPLE 401

R=BOC: $N^1$-[2-(1-tert-Butoxycarbonylpiperidin-4-yloxy)-4-methoxybenzoyl]-$N^2$-(4-methoxybenzoyl)-1,2-benzenediamine.

A. 2-(1-tert-Butoxycarbonylpiperidin-4-yloxy)-4-methoxybenzoic acid

Using methyl 4-methoxysalicylate and 1-Boc-piperidin-4-ol, the acid is obtained using procedures similar to those described at Example 1-G and 1-H.

B. $N^1$-[2-(1-tert-Butoxycarbonylpiperidin-4-yloxy)-4-methoxybenzoyl]-$N^2$-(4-methoxybenzoyl)-1,2-benzenediamine In a manner substantially equivalent to Example 101-D, $N^1$-[2-(1-tert-butoxycarbonylpiperidin-4-yloxy)-4-methoxybenzoyl]-$N^2$-(4-methoxybenzoyl)-1,2-benzenediamine was prepared from 2-(1-tert-butoxycarbonylpiperidin-4-yloxy)-4-methoxybenzoic acid and $N^1$-(4-methoxybenzoyl)-1,2-benzenediamine.

IR (KBr): 1694, 1653, 1607, 1507 cm$^{-1}$
$^1$NMR (300 MHz, DMSO-$d_6$):
FAB-MS 576.4 (M+H)+, 476.4 (des-Boc MH+)
Analysis for $C_{32}H_{37}N_3O_7$:
Calcd: C, 66.77; H, 6.48; N, 7.30.
Found: C, 66.84; H, 6.58; N, 7.35.

EXAMPLE 402

R=H (free base form): $N^1$-(4-Methoxybenzoyl)-$N^2$-[4-methoxy-2-(4-piperidinyloxy)benzoyl]-1,2-benzenediamine.

In a manner substantially equivalent to Example 102, $N^1$-(4-methoxybenzoyl)-$N^2$-[4-methoxy-2-(4-piperidinyloxy)benzoyl]-1,2-benzenediamine was prepared from $N^1$-[2-(1-tert-butoxycarbonylpiperidin-4-yloxy)-4-methoxybenzoyl]-$N^2$-(4-methoxybenzoyl)-1,2-benzenediamine.

$^1$NMR (300 MHz, DMSO-$d_6$):
FAB-MS 476.4 (M+H)+
Analysis for $C_{27}H_{29}N_3O_5$:
Calcd: C, 68.19; H, 6.15; N, 8.84.
Found: C, 67.68; H, 6.21; N, 8.06.

EXAMPLE 403

R=(2S,3R)-2-(BOC-Amino)-3-t-butoxy-1-oxobutyl [N—BOC—O-t-Butyl-L-threonyl]: Procedure D; FIA-MS m/z 633.2 (des-Boc MH+), 733 (M+H)+, 750.4 (MH$_3$O+).

EXAMPLE 404

R=3-Thienylcarbonyl: Procedure D; FIA-MS m/z 586 (M+H)+.

EXAMPLE 405

R=(3-Thienyl)acetyl: Procedure D; FIA-MS m/z 600.2 (M+H)+.

EXAMPLE 406

R=(S)-2-(BOC-Amino)-4-methylthio-1-oxobutyl[N—BOC-L-methionyl]: Procedure D; FIA-MS m/z 707 (M+H)+, 724.4 (MH$_3$O+).

EXAMPLE 407

R=4-t-Butylcyclohexylcarbonyl: Procedure D; FIA-MS m/z 642.2 (M+H)+, 660 (MH$_3$O+).

EXAMPLE 408

R=(R)-3-(BOC)-thiazolidin-4-ylcarbonyl: Procedure D; FIA-MS m/z 691 (M+H)+, 708.4 (MH$_3$O+).

EXAMPLE 409

R=3-(2-Pyridinyl)-1-oxopropyl; Procedure D; FIA-MS m/z 609 (M+H)+.

EXAMPLE 410

R=(S)-5-Oxopyrrolidin-2-ylcarbonyl[L-Pyroglutamyl]: Procedure D; FIA-MS m/z 587 (M+H)+, 604.2 (MH$_3$O+).

EXAMPLE 411

R=(2-Thienyl)acetyl: Procedure D; FIA-MS m/z 600.0 (M+H)+.

EXAMPLE 412

R=2-(2-Thienyl)-2-oxoacetyl: Procedure D; FIA-MS m/z 614.0 (M+H)+.

EXAMPLE 413

R=(1-Tetrazolyl)acetyl: Procedure D; FIA-MS m/z 586.2 (M+H)+.

EXAMPLE 414

R=1-Methylpyrrol-2-ylcarbonyl; Procedure D; FIA-MS m/z 583.0 (M+H)+.

EXAMPLE 415

R=(2-Fluorophenyl)aminocarbonyl: Procedure A; FIA-MS m/z 613.2 (M+H)+.

EXAMPLE 416

R=Butylaminocarbonyl: Procedure A; FIA-MS m/z 575.2 (M+H)+.

EXAMPLE 417

R=Cyclohexylaminocarbonyl: Procedure A; FIA-MS m/z 601.2 (M+H)+.

EXAMPLE 418

R=2-(3-Thienyl)ethylaminocarbonyl: Procedure A; FIA-MS m/z 629.0 (M+H)+.

EXAMPLE 419

R=5-(2-Pyridinyl)thien-2-ylsulfonyl: Procedure A; FIA-MS m/z 699.4 (M+H)+.

EXAMPLE 420

R=4-Cyanophenylsulfonyl: Procedure A; FIA-MS m/z 641.0 (M+H)+.

EXAMPLE 421

R=2-Thienylsulfonyl: Procedure A; FIA-MS m/z 622.2 (M+H)+.

EXAMPLE 422

R=4-Cyanophenylaminocarbonyl: Procedure A; FIA-MS m/z 637 (MH$_2$O−).

EXAMPLE 423

R=2-Thienylcarbonyl: Procedure A; FIA-MS m/z 586.0 (M+H)+.

EXAMPLE 424

R=2-Methoxycarbonylthien-3-ylsulfonyl: Procedure A; FIA-MS m/z 680.2 (M+H)+, 678.2 (M−1)−.

EXAMPLE 425

R=5-Chloro-1,3-dimethylpyrazol-4-ylsulfonyl: Procedure A; FIA-MS m/z 668.2 (M+H)+.

EXAMPLE 426

R=3,5-Dimethylisoxazol-4-ylsulfonyl: Procedure A; FIA-MS m/z 635.0 (M+H)+.

EXAMPLE 427

R=2-Methylpyridin-3-ylcarbonyl: Procedure D; FIA-MS m/z 595.4 (M+H)+.

EXAMPLE 428

R=2-Fluorobenzoyl: Procedure D; FIA-MS m/z 598.2 (M+H)+.

EXAMPLE 429

R=2-Chloropyridin-3-ylcarbonyl; Procedure D; FIA-MS m/z 615.2 (M+H)+.

EXAMPLE 430

R=2-Fluorobenzyl: $N^1$-[2-[1-(2-fluorobenzyl)piperidin-4-yloxy]-4-methoxybenzoyl]-$N^2$-(4-methoxybenzoyl)-1,2-benzenediamine.

General Procedure B for the Reductive Alkylation of Secondary Amines:

$N^1$-(4-Methoxybenzoyl)-$N^2$-[4-methoxy-2-(4-piperidinyloxy)benzoyl]-1,2-benzenediamine free base (30 mg, 60 μmol) was combined in a 4 ml screw-cap vial with a neat aldehyde (180 μmol) of choice, then the mixture was dissolved or suspended in 1 ml of freshly prepared anhydrous MeOH:AcOH (95:5). To the aldehyde-amine mixture was added 500 μl of a freshly prepared sodium cyanoborohydride stock solution (15.1 mg/ml in 95:5 anhydrous MeOH:AcOH, 2 equivalents of sodium cyanoborohydride relative to amine), then the vial was capped and shaken overnight at room temperature on an orbital platform shaker set at 350 rpm. The crude reaction mixtures were purified on SCX cartridges in a manner substantially equivalent to that described above for Example 104. In some cases, purification on silica gel cartridges was necessary following the SCX purification step. In the present example, $N^1$-(4-methoxybenzoyl)-$N^2$-[4-methoxy-2-(4-piperidinyloxy)benzoyl]-1,2-benzenediamine was reductively alkylated with 2-fluorobenzaldehyde to provide $N^1$-[2-(2-fluorobenzylpiperidin-4-yloxy)-4-methoxybenzoyl]-$N^2$-(4-methoxybenzoyl)-1,2-benzenediamine.

FIA-MS m/z 584.0 (M+H)+.

EXAMPLE 431

R=2-Methylbenzyl: Procedure B; FIA-MS m/z 580.2 (M+H)+.

EXAMPLE 432

R=2-Thienylmethyl: Procedure B; FIA-MS m/z 572.2 (M+H)+.

EXAMPLE 433

R=3-Thienylmethyl: Procedure B; FIA-MS m/z 572.2 (M+H)+.

EXAMPLE 434

R=2-Pyridinylmethyl: Procedure B; FIA-MS m/z 567.2 (M+H)+.

EXAMPLE 435

R=Cyclopropylmethyl: Procedure B; FIA-MS m/z 530.2 (M+H)+.

EXAMPLE 436

R=2,2-Dimethylpropyl: Procedure B; FIA-MS m/z 546.2 (M+H)+.

EXAMPLE 437

R=Phenethyl: Procedure B; FIA-MS m/z 580.2 (M+H)+.

EXAMPLE 438

R=2-Methoxybenzyl; Procedure B.

EXAMPLE 439

R=2-Trifluoromethylbenzyl: Procedure B; FIA-MS m/z 634.2 (M+H)+.

EXAMPLE 440

R=2-Pyrrolylmethyl: Procedure B; FIA-MS m/z 555.2 (M+H)+.

EXAMPLE 441

R=(2-Fluorophenylamino)thiocarbonyl: Procedure A; FIA-MS m/z 629.2 (M+H)+.

TABLE 5

Compounds of formula I which may be denoted by the following formula I-5

I-5 in which R has the indicated value were prepared according to the indicated procedure from a requisite corresponding compound of formula I or formula II and the reagents and conditions appropriate for the indicated procedure or by a procedure otherwise noted.

EXAMPLE 501

R=BOC: $N^1$-[2-[2-(4-tert-Butoxycarbonylpiperazin-1-yl) ethoxy]-4-methoxybenzoyl]-$N^2$-(4-methoxybenzoyl)-1,2-benzenediamine.

A. Methyl 2-[2-(4-tert-butoxycarbonylpiperazin-1-yl)ethoxy]-4-methoxybenzoate Methyl 4-methoxysalicylate (7.91 g, 43.4 mmol), 2-(4-tert-butoxycarbonylpiperazin-1-yl)ethanol (10.0 g, 43.4 mmol), and triphenylphosphine (PPh$_3$) (11.3 g, 43.4 mmol) in THF (190 ml) were cooled to 0° C. under N$_2$. DIAD (8.54 ml, 43.4 mmol) was added dropwise, and the reaction allowed to warm to room temperature. After stirring for 18 h, the THF was removed in vacuo, the residue taken up in dichloromethane, and washed with water, dried, and the solvent removed in vacuo to give a yellow oil. After the oil was dissolved in diethyl ether and the solution allowed to stand for 18 h, the triphenylphosphine oxide was filtered, the solvent removed in vacuo, and the crude product purified on silica gel using preparative HPLC and a gradient of hexane and EtOAc to give 11.0 g (64.3%) of a pale yellow oil.

B. 2-[2-(4-tert-Butoxycarbonylpiperazin-1-yl)ethoxy]-4-methoxybenzoic acid

In a manner substantially equivalent to Example 101-C, 2-[2-(4-tert-butoxycarbonylpiperazin-1-yl)ethoxy]-4-methoxybenzoic acid was prepared from methyl 2-[2-(4-tert-butoxycarbonylpiperazin-1-yl)ethoxy]-4-methoxybenzoate (11.0 g, 27.9 mmol) to give 5.9 g (55.6%) of a white foam.

C. $N^1$-[2-[2-(4-tert-Butoxycarbonylpiperazin-1-yl)ethoxy]-4-methoxybenzoyl]-$N^2$-(4-methoxybenzoyl)-1,2-benzenediamine In a manner substantially equivalent to Example 101-D, $N^1$-[2-[2-(4-tert-butoxycarbonylpiperazin-1-yl)ethoxy]-4-methoxybenzoyl]-$N^2$-(4-methoxybenzoyl)-1,2-benzenediamine was prepared from 2-[2-(4-tert-butoxycarbonylpiperazin-1-yl)ethoxy]-4-methoxybenzoic acid (1.0 g, 2.63 mmol) and $N^1$-(4-methoxybenzoyl)-1,2-benzenediamine (0.638 g, 2.63 mmol) to give 0.551 g (34.7%) of a white foam.

$^1$H NMR (300 MHz, DMSO-d$_6$);
FD MS m/z 604.1 (M)
Anal. for $C_{33}H_{40}N_4O_7$:
Calcd: C, 65.55; H, 6.67; N, 9.27.
Found: C, 65.83; H, 6.52; N, 9.10.

EXAMPLE 502

R=H: $N^1$-(4-Methoxybenzoyl)-$N^2$-[4-methoxy-2-[2-(1-piperazinyl)ethoxy]benzoyl]-1,2-benzenediamine.

In a manner substantially equivalent to Example 102, $N^1$-(4-methoxybenzoyl)-$N^2$-[4-methoxy-2-[2-(1-piperazinyl)ethoxy]benzoyl]-1,2-benzenediamine was prepared from $N^1$-[2-[2-(4-tert-butoxycarbonylpiperazin-1-yl)ethoxy]-4-methoxybenzoyl]-$N^2$-(4-methoxybenzoyl)-1,2-benzenediamine (0.50 g, 0.827 mmol) to give 0.391 g (93.7%) of the title compound as a white foam.

$^1$H NMR (300 MHz, DMSO-d$_6$);
FD MS m/z 505.0 (M+H)+.

EXAMPLE 503

R=2-Fluorobenzoyl: Procedure A; FIA-MS m/z 627.4 (M+H)+.

EXAMPLE 504

R=1-Methylpyrrol-2-ylcarbonyl: Procedure D; FIA-MS m/z 612.2 (M+H)+.

EXAMPLE 505

R=2-Fluorobenzyl: Procedure B; FIA-MS m/z 613.2 (M+H)+.

EXAMPLE 506

R=1-Methylpyrrol-2-ylmethyl: Procedure B; FIA-MS m/z 598.4 (M+H)+.

EXAMPLE 507

R=2-Thienylcarbonyl: Procedure A; FIA-MS m/z 615.2 (M+H)+.

EXAMPLE 508

R=2-Thienylmethyl: Procedure B; FIA-MS m/z 601.4 (M+H)+.

EXAMPLE 509

R=2-(2-Thienyl)-2-oxoacetyl: Procedure D; FIA-MS m/z 643.4 (M+H)+.

EXAMPLE 510

R=(2-Thienyl)acetyl: Procedure D; FIA-MS m/z 629.2 (M+H)+.

EXAMPLE 511

R=3-Thienylmethyl: Procedure B; FIA-MS m/z 601.4 (M+H)+.

EXAMPLE 512

R=3-Thienylcarbonyl: Procedure D; FIA-MS m/z 615.2 (M+H)+.

EXAMPLE 513

R=(2-Fluorophenyl)aminocarbonyl: Procedure A; FIA-MS m/z 642.4 (M+H)+.

EXAMPLE 514

R=2-(2-Thienyl)ethylaminocarbonyl: Procedure A; FIA-MS m/z 658.4 (M+H)+.

TABLE 6

Compounds of formula I which may be denoted by the following formula I-6

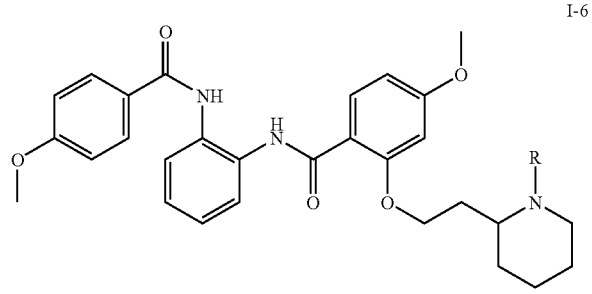

I-6 in which R has the indicated value were prepared according to the indicated procedure from a requisite corresponding compound of formula I or formula II and the reagents and conditions appropriate for the indicated procedure or by a procedure otherwise noted.

EXAMPLE 601

R=BOC: $N^1$-[2-[2-(1-tert-butoxycarbonylpiperidin-2-yl)ethoxy]-4-methoxybenzoyl]-$N^2$-(4-methoxybenzoyl)-1,2-benzenediamine.

A. Methyl 2-[2-(1-tert-butoxycarbonylpiperidin-2-yl)ethoxy]-4-methoxybenzoate In a manner substantially equivalent to Example 501-A, methyl 2-[2-(1-tert-butoxycarbonylpiperidin-2-yl)ethoxy]-4-methoxybenzoate was prepared from methyl 4-methoxysalicylate (13.0 g, 71.1 mmol) to give 21.3 g (76.1%) of a yellow oil.

B. 2-[2-(1-tert-Butoxycarbonylpiperidin-2-yl)ethoxy]-4-methoxybenzoic acid

In a manner substantially equivalent to Example 101-C, 2-[2-(1-tert-butoxycarbonylpiperidin-2-yl)ethoxy]-4-methoxybenzoic acid was prepared from methyl 2-[2-(1-tert-butoxycarbonylpiperidin-2-yl)ethoxy]-4-methoxybenzoate (21.3 g, 54.1 mmol) to give 18.5 g (90.2%) of a clear, colorless glass.

C. $N^1$-[2-[2-(1-tert-Butoxycarbonylpiperidin-2-yl)ethoxy]-4-methoxybenzoyl]-$N^2$-(4-methoxybenzoyl)-1,2-benzenediamine In a manner substantially equivalent to 101-D, $N^1$-[2-[2-(1-tert-butoxycarbonylpiperidin-2-yl)ethoxy]-4-methoxybenzoyl]-$N^2$-(4-methoxybenzoyl)-1,2-benzenediamine was prepared from 2-[2-(1-tert-butoxycarbonylpiperidin-2-yl)ethoxy]-4-methoxybenzoic acid (3.13 g, 8.25 mmol) and $N^1$-(4-methoxybenzoyl)-1,2-benzenediamine (2.00 g, 8.25 mmol). The crude material was purified using a SCX column (Varian, 60 cc/10 g, prewashed with MeOH). The crude material was loaded in 9:1 $CHCl_3$:MeOH, and the product washed through the column with the same. Concentration of the wash in vacuo gave 4.36 g (87.6%) of a white foam.

$^1$H NMR (300 MHz, DMSO-$d_6$);
FD MS m/z 604.3 (M+H)+.

EXAMPLE 602

R=H: $N^1$-(4-Methoxybenzoyl)-$N^2$-[4-methoxy-2-[2-(2-piperidinyl)ethoxy]benzoyl]-1,2-benzenediamine.

In a manner substantially equivalent to Example 102, $N^1$-(4-methoxybenzoyl)-$N^2$-[4-methoxy-2-[2-(2-piperidinyl)ethyloxy]benzoyl]-1,2-benzenediamine was prepared from $N^1$-[2-[2-(1-tert-butoxycarbonylpiperidin-2-yl)ethoxy]-4-methoxybenzoyl]-$N^2$-(4-methoxybenzoyl)-1,2-benzenediamine (1.00 g, 1.66 mmol) to produce 0.615 g (73.8%) of a white foam.

$^1$H NMR (300 MHz, DMSO-$d_6$);
FD MS m/z 504.2 (M+H)+.

EXAMPLE 603

R=4-Methyl-1,2,5-thiadiazol-3-ylacetyl: Procedure D; FIA MS m/z 644.2 (M+H)+, 642.2 (M−1)−.

EXAMPLE 604

R=3-Thienylcarbonyl: Procedure D; FIA MS m/z 614.0 (M+H)+, 612.2 (M−1)−.

EXAMPLE 605

R=2-(2-Thienyl)-2-oxoacetyl: Procedure D; FIA MS m/z 642.2 (M+H)+, 640.2 (M−1)−.

EXAMPLE 606

R=(3-Thienyl)acetyl: Procedure D; FIA MS m/z 628.0 (M+H)+, 626.2 (M−1)−.

EXAMPLE 607

R=3-Methylthien-2-ylcarbonyl: Procedure D; FIA MS m/z 628.2 (M+H)+, 626.2 (M−1)−.

EXAMPLE 608

R=4-(2-Thienyl)-1-oxobutyl: Procedure D; FIA MS m/z 656.2 (M+H)+, 654.2 (M−1)−.

EXAMPLE 609

R=1-Methylpyrrol-2-ylcarbonyl: Procedure D; FIA MS m/z 611.2 (M+H)+, 609.2 (M−1)−.

EXAMPLE 610

R=2-Methylpyridin-3-ylcarbonyl: Procedure D; FIA MS m/z 623.2 (M+H)+, 621.4 (M−1)−.

EXAMPLE 611

R=3-(2-Pyridinyl)-1-oxopropyl: Procedure ?; FIA MS m/z 623.2 (M+H)+, 621.4 (M−1)−.

EXAMPLE 612

R=2-Fluorobenzoyl: Procedure D; FIA MS m/z 626.2 (M+H)+, 624.4 (M−1)−.

EXAMPLE 613

R=2-Fluorophenylacetyl: Procedure D; FIA MS m/z 640.2 (M+H)+, 638.2 (M−1)−.

EXAMPLE 614

R=4-Fluorophenylacetyl; Procedure D; FIA MS m/z 640.2 (M+H)+, 638.2 (M−1)−.

EXAMPLE 615

R=(2-Fluorophenyl)aminocarbonyl: Procedure A; FIA MS m/z 641.0 (M+H)+, 639.4 (M−1)−.

EXAMPLE 616

R=3-(2-Thienyl)-1-oxopropyl: Procedure A; FIA MS m/z 657.2 (M+H)+, 655.2 (M−1)−.

EXAMPLE 617

R=(2-Fluorophenylamino)thiocarbonyl; Procedure A; ES MS m/z 657.3 (M+H)+, 655.2 (M−1)−.

EXAMPLE 618

R=(2-Thienyl)acetyl; Procedure D; ES MS m/z 628.3 (M+H)+, 626.2 (M−1)−.

EXAMPLE 619

R=Benzyl: Procedure B; ES MS m/z 594.3 (M+H)+, 592.2 (M−1)−.

EXAMPLE 620

R=2-Methoxybenzyl: Procedure B; ES MS m/z 624.3 (M+H)+, 622.3 (M−1)−.

EXAMPLE 621

R=2,3-Dimethoxybenzyl: Procedure B; ES MS m/z 654.3 (M+H)+, 652.3 (M−1)−.

EXAMPLE 622

R=2-Ethoxybenzyl: Procedure B; ES MS m/z 638.3 (M+H)+, 636.3 (M−1)−.

EXAMPLE 623

R=3-Thienylmethyl; Procedure B; ES MS m/z 600.2 (M+H)+, 598.2 (M−1)−.

TABLE 7

Compounds of formula I which may be denoted by the following formula I-7

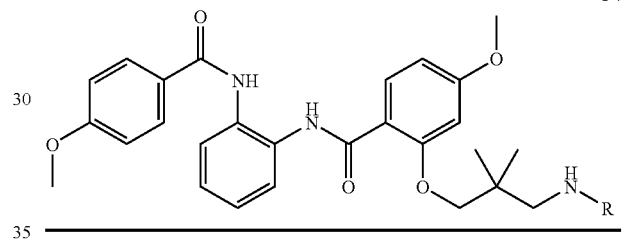

I-7 in which R has the indicated value were prepared according to the indicated procedure from a requisite corresponding compound of formula I or formula II and the reagents and conditions appropriate for the indicated procedure or by a procedure otherwise noted.

EXAMPLE 701

R=BOC: $N^1$-[2-(3-tert-Butoxycarbonylamino-2,2-dimethylpropoxy)-4-methoxybenzoyl]-$N^2$-(4-methoxybenzoyl)-1,2-benzenediamine.

A. Methyl 2-(3-tert-Butoxycarbonylamino-2,2-dimethylpropoxy)-4-methoxybenzoate i. 3-tert-Butoxycarbonylamino-2,2-dimethylpropanol To a solution of neopentanolamine (75 g, 728 mmol) and sodium carbonate (77.2 g, 728 mmol) in p-dioxane (1 L) and water (1 L) at 0° C. was added di-tert-butyl dicarbonate (175 g, 801 mmol). After stirring overnight, the solution was concentrated in vacuo and the residue was partitioned between ethyl acetate and water. The organic phase was washed again with brine and then dried with $MgSO_4$, filtered, and concentrated in vacuo to give 139 g (94%) of a thick, colorless syrup.
$^1$NMR ii. In a manner substantially equivalent to Example 501-A, 4-methoxysalicylate (16.4 g, 90.0 mmol) and 3-tert-butoxycarbonylamino-2,2-dimethylpropanol (18.3 g, 90.0 mmol) gave 23.2 g (70.1%) of a yellow oil.

B. 2-(3-tert-Butoxycarbonylamino-2,2-dimethylpropoxy)-4-methoxybenzoic acid

In a manner substantially equivalent to Example 101-C, methyl 2-(3-tert-butoxycarbonylamino-2,2-dimethylpropoxy)-4-methoxybenzoate (23.2 g, 63.1 mmol) gave 21.0 g (94.1%) of a colorless, tacky oil.

C. $N^1$-[2-(3-tert-Butoxycarbonylamino-2,2-dimethylpropoxy)-4-methoxybenzoyl]-$N^2$-(4-methoxybenzoyl)-1,2-benzenediamine In a manner substantially equivalent to Example 101-D, 2-(3-tert-butoxycarbonylamino-2,2-dimethylpropoxy)-4-methoxybenzoic acid (2.92 g, 8.25 mmol) and $N^1$-(4-methoxybenzoyl)-1,2-benzenediamine (2.00 g, 8.25 mmol) were coupled. The crude material was dissolved in dichloromethane, and aminomethylated polystyrene was added to remove the unreacted acid chloride. The resin was filtered, the solution added directly to a SCX column (Varian, 60 cc/10 g, prewashed with MeOH), and the product washed through the column with 9:1 $CHCl_3$:MeOH. Concentration of the wash in vacuo gave 3.50 g (73.4%) of a white foam.

$^1$H NMR (300 MHz, DMSO-$d_6$);
FAB MS m/z 578.3 (M+H)+.

EXAMPLE 702

R=H: $N^1$-[2-(3-Amino-2,2-dimethylpropoxy)-4-methoxybenzoyl]-$N^2$-(4-methoxybenzoyl)-1,2-benzenediamine.

In a manner substantially equivalent to Example 102, $N^1$-[2-(3-tert-butoxycarbonylamino-2,2-dimethylpropoxy)-4-methoxybenzoyl]-$N^2$-(4-methoxybenzoyl)-1,2-benzenediamine (2.00 g, 3.46 mmol) gave a yellow oil after SCX chromatography. The crude product was purified via silica gel chromatography ($CHCl_3$:MeOH) to give 1.4 g (84.8%) of a white foam.

$^1$H NMR (300 MHz, DMSO-$d_6$);
FAB MS m/z 478.3 (M+H)+.

EXAMPLE 703

R=3-Thienylcarbonyl: Procedure D; FIA MS m/z 588.2 (M+H)+, 586.2 (M−1)−.

EXAMPLE 704

R=(3-Thienyl)acetyl: Procedure D; FIA MS m/z 602.2 (M+H)+, 600.4 (M−1)−.

EXAMPLE 705

R=3-Methylthien-2-ylcarbonyl: Procedure D; FIA MS m/z 602.2 (M+H)+, 600.2 (M−1)−.

EXAMPLE 706

R=4-(2-Thienyl)-1-oxobutyl: Procedure D; FIA MS m/z 630.2 (M+H)+, 628.4 (M−1)−.

EXAMPLE 707

R=1-Methylpyrrol-2-ylcarbonyl: Procedure D; FIA MS m/z 585.2 (M+H)+, 583.2 (M−1)−.

EXAMPLE 708

R=2-(4-Fluorophenyl)-2-oxoacetyl: Procedure D; FIA MS m/z 630.2 (M+H)+, 628.4 (M−1)−.

EXAMPLE 709

R=1-Methyl-5-oxopyrrolidin-3-ylcarbonyl: Procedure D; FIA MS m/z 603.2 (M+H)+, 601.4 (M−1)−.

EXAMPLE 710

R=(2-Fluorophenyl)aminocarbonyl: Procedure A; FIA MS m/z 615.2 (M+H)+, 613.2 (M−1)−.

EXAMPLE 711

R=2-(2-Thienyl)ethylaminocarbonyl: Procedure A; FIA MS m/z 631.4 (M+H)+, 629.2 (M−1)−.

EXAMPLE 712

R=(2-Fluorophenylamino)thiocarbonyl: Procedure A; FIA MS m/z 631.2 (M+H)+, 629.4 (M−1)−.

EXAMPLE 713

R=(2-Chlorophenyl)aminocarbonyl: Procedure A; FIA MS m/z 631.2 (M+H)+, 629.2 (M−1)−.

EXAMPLE 714

R=(2-Fluorophenyl)aminosulfonyl: Procedure C; FIA MS m/z 636.0 (M+H)+, 634.2 (M−1)−.

EXAMPLE 715

R=2-Thienylsulfonyl; Procedure C; FIA MS m/z 624.2 (M+H)+, 622.4 (M−1)−.

EXAMPLE 716

R=2-Methoxycarbonylthien-3-ylsulfonyl: Procedure C; FIA MS m/z 682.2 (M+H)+, 680.2 (M−1)−.

EXAMPLE 717

R=(S)-1-Methoxycarbonyl-2-methylpropylaminocarbonyl: Procedure A;
FIA MS m/z 649.2 (M+H)+, 647.6 (M−1)−.

General Procedure E for Reductive Alkylation of Primary Amines Such as the Compound Described in Example 702:

To an aldehyde (94.2 µmol, 1.5 eq) of choice in a 1 ml screw cap vial was added $N^1$-[2-(3-amino-2,2-dimethylpropoxy)-4-methoxybenzoyl]-$N^2$-(4-methoxybenzoyl)-1,2-benzenediamine (30 mg, 62.8 µmol) as a solution in MeOH (0.25 ml). The vial was capped and allowed to stand at room temperature. After 1 h excess solid $NaBH_4$ was added, and the vial left capped at room temperature overnight. The reaction was diluted with MeOH (0.5 ml) and $CHCl_3$ (0.5 ml) and a drop of AcOH added. The solution was applied to a prewashed (MeOH) 6 cc, 1 g SCX solid phase extraction cartridge and the cartridge washed with 2×5 ml of $CHCl_3$:MeOH (9:1). The product was eluted with 2×5 ml of 3:1 CHCl$_3$:2N NH$_3$ in MeOH, and the solvent removed in vacuo to give the purified product.

EXAMPLE 718

R=3-Methylbenzyl: Procedure E; FIA MS m/z 582.3 (M+H)+, 580.3 (M−1)−.

EXAMPLE 719

R=2-Methylthien-3-ylmethyl: Procedure E; FIA MS m/z 588.2 (M+H)+, 586.3 (M−1)−.

EXAMPLE 720

R=2-Methoxybenzyl: Procedure E; FIA MS m/z 598.3 (M+H)+, 596.3 (M−1)−.

EXAMPLE 721

R=4-Methylbenzyl: Procedure E; FIA MS m/z 582.3 (M+H)+, 580.3 (M−1)−.

EXAMPLE 722

R=4-Fluorobenzyl: Procedure E; FIA MS m/z 586.2 (M+H)+, 584.3 (M−1)−.

EXAMPLE 723

R=2-Fluorobenzyl: Procedure E; FIA MS m/z 586.2 (M+H)+, 584.3 (M−1)−.

EXAMPLE 724

R=2,3-Methylenedioxybenzyl: Procedure E; FIA MS m/z 612.2 (M+H)+, 610.3 (M−1)−.

EXAMPLE 725

R=2-Methylbenzyl: Procedure E; FIA MS m/z 582.3 (M+H)+, 580.3 (M−1)−.

EXAMPLE 726

R=2-Bromobenzyl: Procedure E; FIA MS m/z 646.2 (M+H)+, 648.2 (M+3).

EXAMPLE 727

R=2,4-Dimethylbenzyl: Procedure E; FIA MS m/z 596.3 (M+H)+, 594.3 (M−1)−.

EXAMPLE 728

R=5-Methylimidazol-4-ylmethyl: Procedure E; FIA MS m/z 572.3 (M+H)+, 570.3 (M−1)−.

EXAMPLE 729

R=3-Thienylmethyl: Procedure E; FIA MS m/z 574.2 (M+H)+, 572.3 (M−1)−.

EXAMPLE 730

R=2-Thienylmethyl: Procedure E; FIA MS m/z 574.2 (M+H)+, 572.3 (M−1)−.

EXAMPLE 731

R=2-Chlorobenzyl: Procedure E; FIA MS m/z 602.2 (M+H)+, 600.3 (M−1)−.

EXAMPLE 732

R=1-Methylpyrrol-2-ylmethyl: Procedure E; FIA MS m/z 571.3 (M+H)+, 569.3 (M−1)−.

TABLE 8

Compounds of formula I which may be denoted by the following formula I-8

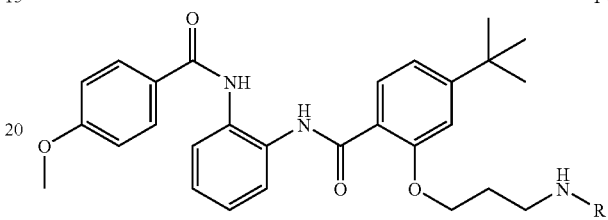

I-8 in which R has the indicated value were prepared according to the indicated procedure from a requisite corresponding compound of formula I or formula II and the reagents and conditions appropriate for the indicated procedure or by a procedure otherwise noted.

EXAMPLE 801

R=BOC: N$^1$-[2-(3-tert-Butoxycarbonylaminopropoxy)-4-tert-butylbenzoyl]-N$^2$-(4-methoxybenzoyl)-1,2-benzenediamine.

A. Methyl 2-(3-tert-Butoxycarbonylaminopropoxy)-4-tert-butylbenzoate

In a manner substantially equivalent to Example 101-B, methyl 4-tert-butylsalicylate (see Example 901-C below for preparation of methyl 4-tert-butylsalicylate; 1.10 g, 5.28 mmol) was alkylated with 3-bromo-N-(tert-butoxycarbonyl) propylamine (1.88 g, 7.92 mmol) to give 1.00 g (51.8%) of methyl 2-(3-tert-butoxycarbonylaminopropoxy)-4-tert-butylbenzoate as a yellow oil.

B. 2-(3-tert-Butoxycarbonylaminopropoxy)-4-tert-butylbenzoic acid

In a manner substantially equivalent to Example 101-C, methyl 2-(3-tert-butoxycarbonylaminopropoxy)-4-tert-butylbenzoate (1.00 g, 2.74 mmol) gave 0.75 g (78.0%) of a pale yellow oil.

C. N$^1$-[2-(3-tert-Butoxycarbonylaminopropoxy)-4-tert-butylbenzoyl]-N$^2$-(4-methoxybenzoyl)-1,2-benzenediamine In a manner substantially equivalent to Example 101-D, N$^1$-[2-(3-tert-butoxycarbonylaminopropoxy)-4-tert-butylbenzoyl]-N$^2$-(4-methoxybenzoyl)-1,2-benzenediamine was prepared from 2-(3-tert-butoxycarbonylaminopropoxy)-4-tert-butylbenzoic acid (0.75 g, 2.13 mmol) and N$^1$-(4-methoxybenzoyl)-1,2-benzenediamine (0.516 g, 2.13 mmol). Unreacted amine was remove by passing the crude product through a SCX column (60 cc/10 g, prewashed with MeOH), and IRA-900 resin (MeO⁻ form) was added to remove unreacted acid. After 1.5 h, the resin was filtered off, and the solution concentrated in vacuo to give 0.319 g (26.0%) of a yellow foam.

¹H NMR (300 MHz, DMSO-$d_6$);
FD MS m/z 575.0 (M).

EXAMPLE 802

R=H: $N^1$-[2-(3-Aminopropoxy)-4-tert-butylbenzoyl]-$N^2$-(4-methoxybenzoyl)-1,2-benzenediamine.

In a manner substantially equivalent to Example 102, $N^1$-[2-(3-tert-butoxycarbonylaminopropoxy)-4-tert-butylbenzoyl]-$N^2$-(4-methoxybenzoyl)-1,2-benzenediamine (0.315 g, 0.547 mmol) gave 0.258 g, (99%) of a white foam.

¹H NMR (300 MHz, DMSO-$d_6$);
FD MS m/z 575.0 (M+H)+.

EXAMPLE 803

R=3-Thienylcarbonyl; Procedure D; FIA MS m/z 603.0 (M+NH$_3^+$).

EXAMPLE 804

R=4-tert-Butylcyclohexylcarbonyl: Procedure D; FIA MS m/z 659.4 (M+NH$_3^+$).

EXAMPLE 805

R=(2S,3R)-2-(BOC-Amino)-3-t-butoxy-1-oxobutyl [N—BOC—O-t-Butyl-L-threonyl]: Procedure D; FIA MS m/z 750.4 (M+NH$_3^+$).

EXAMPLE 806

R=(3-Thienyl)acetyl: Procedure D; ES MS m/z 600.0 (M+H)+, 598.0 (M−1)−.

EXAMPLE 807

R=1-Methylpyrrol-2-ylcarbonyl: Procedure D; ES MS m/z 583.0 (M+H)+, 581.0 (M−1)−.

TABLE 9

Compounds of formula I which may be denoted by the following formula I-9

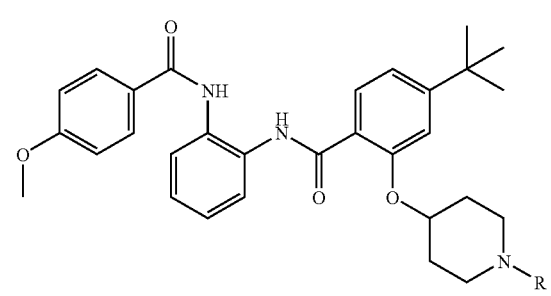

I-9 in which R has the indicated value were prepared according to the indicated procedure from a requisite corresponding compound of formula I or formula II and the reagents and conditions appropriate for the indicated procedure or by a procedure otherwise noted.

EXAMPLE 901

R=BOC; $N^1$-[2-(1-tert-Butoxycarbonylpiperidin-4-yloxy)-4-tert-butylbenzoyl]-$N^2$-(4-methoxybenzoyl)-1,2-benzenediamine.

A. 3-tert-Butylphenyl methoxymethyl ether, see the preparation described at Example 1-D B. 4-tert-Butyl-2-(methoxymethoxy)benzoic acid, see the preparation described at Example 1-E C. Methyl 4-tert-butyl-2-hydroxybenzoate, see the preparation described at Example 1-F D. Methyl 2-(1-tert-butoxycarbonylpiperidin-4-yloxy)-4-tert-butylbenzoate Methyl 4-tert-butyl-2-hydroxybenzoate (2.04 g, 9.8 mmol) was placed in a dry 250 ml RBF along with 1-Boc-4-hydroxypiperidine (1.97 g, 9.8 mmol) and triphenylphosphine (2.57 g, 9.8 mmol). The solids were dissolved in 50 ml of dry THF; then the mixture was chilled on ice with stirring under a nitrogen atmosphere. Diisopropyl azodicarboxylate (DIAD) (1.98 g, 1.92 ml, 9.8 mmol) was added dropwise to the chilled solution over 20 min. The mixture was stirred a few minutes on ice, then allowed to warm to room temperature and left stirring overnight. The reaction mixture was concentrated in vacuo, partitioned between 200 ml each water and dichloromethane and the organic layer washed with brine, then dried over sodium sulfate and reconcentrated in vacuo. The yellow residue was dissolved in 70 ml of ether, then chilled (−10° C.) to precipitate most of the triphenylphosphine oxide. The mixture was filtered, reconcentrated and then purified on a Waters Prep 500 chromatograph (two cartridges, hexanes through 7:3 hexanes:EtOAc) to give the title product (2.41 g, 63%) as a colorless oil.

IR (KBr): 1720, 1682 cm⁻¹
¹NMR (300 MHz, DMSO-$d_6$):
FD-MS, m/z 391.3 (M+).
Analysis for $C_{22}H_{33}NO_5$:
Calcd: C, 67.49; H, 8.50; N, 3.58.
Found: C, 67.43; H, 8.64; N, 3.58.

E. 2-(1-tert-Butoxycarbonylpiperidin-4-yloxy)-4-tert-butylbenzoic acid

In a 50 ml RBF was suspended methyl 2-(1-tert-butoxycarbonylpiperidin-4-yloxy)-4-tert-butylbenzoate (2.4 g, 6.1 mmol) in 25 ml of 3:1 THF:water to give a light emulsion, then was added solid LiOH monohydrate (567 mg, 13.5 mmol), the flask was fitted with a reflux condenser, and the mixture was heated at 50° C. with stirring for 16 h. The mixture was diluted with 75 ml water and washed twice with diethyl ether. The aqueous layer was acidified to about pH 2 with 1 N NaHSO$_4$, and the resulting slurry extracted twice with 100 ml portions of EtOAc. The combined EtOAc layers were washed with brine, dried, then concentrated in vacuo to afford 2.1 g (91%) of the title acid as a brittle white foam.

¹NMR (300 MHz, DMSO-$d_6$):
FIA-MS, m/z 378.6 (M+); 376.4 (M−1)−.
Analysis for $C_{21}H_{31}NO_5$:
Calcd: C, 66.82; H, 8.28; N, 3.71.
Found: C, 66.65; H, 8.11; N, 3.72.

F. N$^1$-[2-(1-tert-Butoxycarbonylpiperidin-4-yloxy)-4-tert-butylbenzoyl]-N$^2$-(4-methoxybenzoyl)-1,2-benzenediamine In a manner substantially equivalent to Example 101-D, N$^1$-[2-(1-tert-butoxycarbonylpiperidin-4-yloxy)-4-tert-butylbenzoyl]-N$^2$-(4-methoxybenzoyl)-1,2-benzenediamine was prepared from 2-(1-tert-butoxycarbonylpiperidin-4-yloxy)-4-tert-butylbenzoic acid and N$^1$-(4-methoxybenzoyl)-1,2-benzenediamine.

$^1$NMR (300 MHz, DMSO-d$_6$):
IR (KBr): 2964, 1695, 1658, 1608 cm$^{-1}$
FIA-MS m/z 602.4 (M+); 600.4 (M−1)−
Analysis for C$_{35}$H$_{43}$N$_3$O$_6$:
Calcd: C, 69.86; H, 7.20; N, 6.98.
Found: C, 69.68; H, 6.93; N, 6.83.

EXAMPLE 902

R=H: N$^1$-[4-tert-butyl-2-(4-piperidinyloxy)benzoyl]-N$^2$-(4-methoxybenzoyl)-1,2-benzenediamine.

In a manner substantially equivalent to Example 102, N$^1$-[4-tert-butyl-2-(4-piperidinyloxy)benzoyl]-N$^2$-(4-methoxybenzoyl)-1,2-benzenediamine was prepared from N$^1$-[2-(1-tert-butoxycarbonylpiperidin-4-yloxy)-4-tert-butylbenzoyl]-N$^2$-(4-methoxybenzoyl)-1,2-benzenediamine.

$^1$NMR (300 MHz, DMSO-d$_6$):
FIA-MS m/z 502.3 (M+); 500.3 (M−1)−
Analysis for C$_{30}$H$_{35}$N$_3$O$_4$:
Calcd: C, 71.83; H, 7.03; N, 8.38.
Found: C, 69.96; H, 6.96; N, 8.08.

EXAMPLE 903

R=(2-Fluorophenyl)aminocarbonyl: Procedure A; ES-MS m/z 639.3 (M+H)+, 637.3 (M−1)−.

EXAMPLE 904

R=1-Methylpyrrol-2-ylcarbonyl: Procedure D; ES-MS m/z 609.3 (M+H)+, 607.4 (M−1)−.

EXAMPLE 905

R=Benzyl: Procedure B; ES-MS m/z 592.3 (M+H)+, 590.4 (M−1)−.

EXAMPLE 906

R=2-Bromobenzyl: Procedure B; ES-MS m/z 670/672.3 (M+H)+, 668.3/670.2 (M−1)−.

EXAMPLE 907

R=2-Fluorobenzyl: Procedure B; ES-MS m/z 610.3 (M+H)+, 608.4 (M−1)−.

EXAMPLE 908

R=2-Chlorobenzyl: Procedure B; ES-MS m/z 626.3 (M+H)+, 624.3 (M−1)−.

EXAMPLE 909

R=2-Methoxybenzyl: Procedure B; ES-MS m/z 622.4 (M+H)+, 620.4 (M−1)−.

EXAMPLE 910

R=2,3-Dimethoxybenzyl: Procedure B; ES-MS m/z 652.4 (M+H)+, 650.4 (M−1)−.

EXAMPLE 911

R=2-Ethoxybenzyl: Procedure B; ES-MS m/z 636.4 (M+H)+, 634.4 (M−1)−.

EXAMPLE 912

R=2-Trifluoromethylbenzyl: Procedure B; ES-MS m/z 660.3 (M+H)+, 658.3 (M−1)−.

EXAMPLE 913

R=2-Methylbenzyl: Procedure B; ES-MS m/z 606.4 (M+H)+, 604.4 (M−1)−.

EXAMPLE 914

R=2,4-Dimethylbenzyl: Procedure B; ES-MS m/z 620.4 (M+H)+, 618.4 (M−1)−.

EXAMPLE 915

R=3-Fluorobenzyl: Procedure B; ES-MS m/z 610.3 (M+H)+, 608.4 (M−1)−.

EXAMPLE 916

R=3-Trifluoromethylbenzyl: Procedure B; ES-MS m/z 660.3 (M+H)+, 658.4 (M−1)−.

EXAMPLE 917

R=3-Methylbenzyl: Procedure B; ES-MS m/z 606.3 (M+H)+, 604.4 (M−1)−.

EXAMPLE 918

R=4-Fluorobenzyl: Procedure B; ES-MS m/z 610.3 (M+H)+, 608.4 (M−1)−.

EXAMPLE 919

R=(2-Fluorophenylamino)thiocarbonyl: Procedure A; ES-MS m/z 655.3 (M+H)+, 653.3 (M−1)−.

EXAMPLE 920

R=2-Thienylmethyl: Procedure B; ES-MS m/z 598.3 (M+H)+, 596.3 (M−1)−.

EXAMPLE 921

R=3-Methylthien-2-ylmethyl: Procedure B; ES-MS m/z 612.3 (M+H)+, 610.4 (M−1)−.

EXAMPLE 922

R=2-(2-Thienyl)-2-oxoacetyl: Procedure D; ES-MS m/z 640.3 (M+H)+, 638.3 (M−1)−.

EXAMPLE 923

R=(2-Thienyl)acetyl: Procedure D; ES-MS m/z 626.3 (M+H)+, 624.3 (M−1)−.

EXAMPLE 924

R=3-Thienylmethyl: Procedure B; ES-MS m/z 598.3 (M+H)+, 596.3 (M−1)−.

EXAMPLE 925

R=4-Trifluoromethylbenzyl: Procedure B; ES-MS m/z 660.3 (M+H)+, 658.3 (M−1)−.

EXAMPLE 926

R=4-Methylbenzyl; Procedure B; ES-MS m/z 606.3 (M+H)+, 604.4 (M−1)−.

EXAMPLE 927

R=2-Nitrobenzyl: Procedure B; ES-MS m/z 637.3 (M+H)+, 635.3 (M−1)−.

EXAMPLE 928

R=2,4-Difluorobenzyl: Procedure B; ES-MS m/z 628.3 (M+H)+, 626.4 (M−1)−.

EXAMPLE 929

R=2,6-Dimethoxybenzyl: Procedure B; ES-MS m/z 652.4 (M+H)+, 650.4 (M−1)−.

EXAMPLE 930

R=Cyclopropylmethyl: Procedure B; ES-MS m/z 556.3 (M+H)+, 554.4 (M−1)−.

EXAMPLE 931

R=2,3-Methylenedioxybenzyl: Procedure B; ES-MS m/z 636.3 (M+H)+, 634.4 (M−1)−.

EXAMPLE 932

R=2-tert-Butylthiobenzyl: Procedure B; ES-MS m/z 680.4 (M+H)+, 678.4 (M−1)−.

EXAMPLE 933

R=2-(2-Thienyl)ethylaminocarbonyl: Procedure A; ES-MS m/z 655.3 (M+H)+, 653.4 (M−1)−.

EXAMPLE 934

R=3-Fluoro-2-methylbenzyl: Procedure B; ES-MS m/z 624.3 (M+H)+, 622.4 (M−1)−.

EXAMPLE 935

R=2,5-Dimethylbenzyl: Procedure B; ES-MS m/z 620.4 (M+H)+, 618.4 (M−1)−.

EXAMPLE 936

R=2,6-Difluorobenzyl: Procedure B; ES-MS m/z 628.3 (M+H)+, 626.4 (M−1)−.

TABLE 10

Compounds of formula I which may be denoted by the following formula I-10

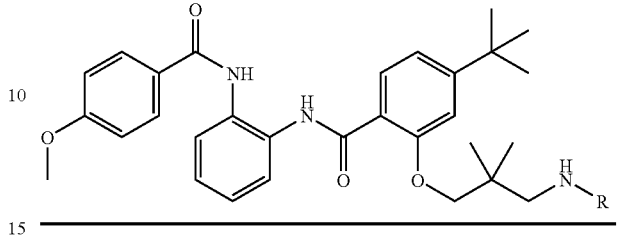

I-10 in which R has the indicated value were prepared according to the indicated procedure from a requisite corresponding compound of formula I or formula II and the reagents and conditions appropriate for the indicated procedure or by a procedure otherwise noted.

EXAMPLE 1001

R=BOC: $N^1$-[2-(3-tert-Butoxycarbonylamino-2,2-dimethylpropoxy)-4-tert-butylbenzoyl]-$N^2$-(4-methoxybenzoyl)-1,2-benzenediamine.

In a manner substantially equivalent to Example 101-D, 2-(3-tert-butoxycarbonylamino-2,2-dimethylpropoxy)-4-tertbutylbenzoic acid (1.50 g, 3.95 mmol) and $N^1$-(4-methoxybenzoyl)-1,2-benzenediamine (1.92 g, 7.92 mmol) were coupled to give, after SCX removal of the unreacted aniline, a pale yellow foam.

$^1$H NMR (300 MHz, DMSO-$d_6$);

FIA MS m/z 604.4 (M+H)+, 602.5 (M−1)−.

EXAMPLE 1002

R=H: $N^1$-[2-(3-amino-2,2-dimethylpropoxy)-4-tert-butylbenzoyl]-$N^2$-(4-methoxybenzoyl)-1,2-benzenediamine.

In a manner substantially equivalent to Example 102, $N^1$-[2-(3-tert-butoxycarbonylamino-2,2-dimethylpropoxy)-4-tert-butylbenzoyl]-$N^2$-(4-methoxybenzoyl)-1,2-benzenediamine (1.50 g, 2.48 mmol) gave 1.08 g (86.4%) of a pale yellow foam.

$^1$H NMR (300 MHz, DMSO-$d_6$); FIA MS m/z 504.3 (M+H)+, 502.4 (M−1)−.

EXAMPLE 1003

R=1-Methylpyrrol-2-ylcarbonyl: Procedure D; FIA MS m/z 611.4 (M+H)+, 609.4 (M−1)−.

EXAMPLE 1004

R=2-Methylthien-3-ylcarbonyl: Procedure D; FIA MS m/z 628.4 (M+H)+, 626.4 (M−1)−.

EXAMPLE 1005

R=3-Thienylcarbonyl: Procedure D; FIA MS m/z 614.2 (M+H)+.

EXAMPLE 1006

R=2-Fluorobenzoyl: Procedure D; FIA MS m/z 626.3 (M+H)+, 624.6 (M−1)−.

EXAMPLE 1007

R=2-(2-Thienyl)-2-oxoacetyl: Procedure D; FIA MS m/z 642.3 (M+H)+, 640.4 (M−1)−.

EXAMPLE 1008

R=(3-Thienyl)acetyl: Procedure D; FIA MS m/z 628.5 (M+H)+, 626.5 (M−1)−.

EXAMPLE 1009

R=2-Pyridinylcarbonyl: Procedure D; FIA MS m/z 609.3 (M+H)+, 607.5 (M−1)−.

EXAMPLE 1010

R=2-Methyl-2H-pyrazol-3-ylcarbonyl: Procedure D; FIA MS m/z 612.4 (M+H)+, 610.4 (M−1)−.

EXAMPLE 1011

R=2-Methylbenzoyl: Procedure D; FIA MS m/z 622.5 (M+H)+, 620.8 (M−1)−.

EXAMPLE 1012

R=2-Methylthiobenzyl: Procedure D; FIA MS m/z 654.4 (M+H)+, 652.5 (M−1)−.

EXAMPLE 1013

R=2-Methoxybenzoyl: Procedure D; FIA MS m/z 638.4 (M+H)+.

EXAMPLE 1014

R=3-(2-Pyridinyl)-1-oxopropyl: Procedure D; FIA MS m/z 637.4 (M+H)+, 635.5 (M−1)−.

EXAMPLE 1015

R=4-Methyl-1,2,3-thiadiazol-5-ylcarbonyl: Procedure D; FIA MS m/z 630.4 (M+H)+, 628.6 (M−1)−.

EXAMPLE 1016

R=2-Methylthien-3-ylmethyl: Procedure E; FIA MS m/z 614.4 (M+H)+, 612.5 (M−1)−.

EXAMPLE 1017

R=2-Methylbenzyl: Procedure E; FIA MS m/z 608.4 (M+H)+, 606.6 (M−1)−.

TABLE 11

Compounds of formula I which may be denoted by the following formula I-11

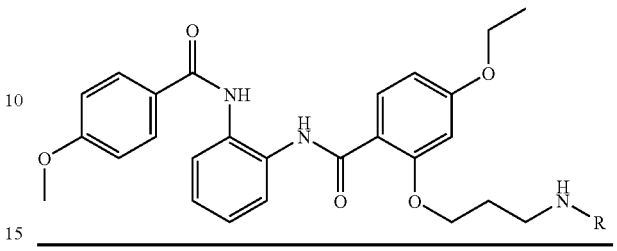

I-11 in which R has the indicated value were prepared according to the indicated procedure from a requisite corresponding compound of formula I or formula II and the reagents and conditions appropriate for the indicated procedure or by a procedure otherwise noted.

EXAMPLE 1101

R=BOC: $N^1$-[2-(3-tert-Butoxycarbonylaminopropoxy)-4-ethoxybenzoyl]-$N^2$-(4-methoxybenzoyl)-1,2-benzenediamine.

A. Methyl 4-ethoxysalicylate

Methyl 4-hydroxysalicylate (10.0 g, 59.5 mmol) was dissolved in DMF. Ethyl iodide (9.74 g, 62.4 mmol) was added, followed by potassium carbonate (8.63 g, 62.4 mmol), and the reaction mixture was stirred under $N_2$ at room temperature for 18 h. The reaction mixture was concentrated in vacuo to remove the majority of the DMF, and the residue taken up in EtOAc, and washed with water (2×), dried, and concentrated in vacuo to give an off-white solid. Recrystallization from hexane gave 6.41 g, (54.9%) of methyl 4-ethoxysalicylate as an off-white solid.

$^1$H NMR (300 MHz, DMSO-$d_6$);

FD MS m/z 196.0 (M).

B. Methyl 2-(3-tert-butoxycarbonylaminopropoxy)-4-ethoxybenzoate

In a manner substantially equivalent to Example 101-B, Methyl 4-ethoxysalicylate (6.30 g, 32.1 mmol) was alkylated with 3-bromo-N-tert-butoxycarbonylpropylamine (11.5 g, 48.2 mmol) to give, after silica gel purification using a Waters prep 500 (hexane:EtOAc gradient), 8.7 g (77.0%) of a highly crystalline white solid.

C. 2-(3-tert-Butoxycarbonylaminopropoxy)-4-ethoxybenzoic acid

In a manner substantially equivalent to Example 101-C, saponification of methyl 2-(3-tert-butoxycarbonylaminopropoxy)-4-ethoxybenzoate (8.70 g, 24.6 mmol) gave 7.11 g (85.6%) of 2-(3-tert-butoxycarbonylaminopropoxy)-4-ethoxybenzoic acid as a waxy solid.

D. N¹-[2-(3-tert-Butoxycarbonylaminopropoxy)-4-ethoxybenzoyl]-N²-(4-methoxybenzoyl)-1,2-benzenediamine In a manner substantially equivalent to Example 101-D, 2-(3-tert-butoxycarbonylaminopropoxy)-4-ethoxybenzoic acid (1.00 g, 2.95 mmol) and N¹-(4-methoxybenzoyl)-1,2-benzenediamine (0.715 g, 2.95 mmol) gave, after recrystallization from hexanes:EtOAc, 1.18 g (71%) of N¹-[2-(3-tert-butoxycarbonylaminopropoxy)-4-ethoxybenzoyl]-N²-(4-methoxybenzoyl)-1,2-benzenediamine as a white solid.
¹H NMR (300 MHz, DMSO-d₆);
FAB MS m/z 564.2 (M+H)+.

EXAMPLE 1102

R=H: N¹-[2-(3-aminopropoxy)-4-ethoxybenzoyl]-N²-(4-methoxybenzoyl)-1,2-benzenediamine.
In a manner substantially equivalent to Example 102, N¹-[2-(3-tert-butoxycarbonylaminopropoxy)-4-ethoxybenzoyl]-N²-(4-methoxybenzoyl)-1,2-benzenediamine (1.15 g, 2.04 mmol) gave 0.869 g (91.9%) of the amine as a white foam.
¹H NMR (300 MHz, DMSO-d₆);
FAB MS m/z 464.3 (M+H)+.

EXAMPLE 1103

R=(S)-2-(BOC-Amino)-3-(benzyloxycarbonyl)-1-oxopropyl [N—BOC-β-Benzyl-L-α-aspartyl]: Procedure D; FIA MS m/z 769.4 (M+H)+.

EXAMPLE 1104

R=(S)-2-(BOC-Amino)-4-methyl-1-oxopentyl[N—BOC-L-Leucyl]: Procedure D; FIA MS m/z 677.4 (M+H)+.

EXAMPLE 1105

R=(S)-2-(BOC-Amino)-3-methyl-1-oxobutyl[N—BOC-L-Valyl]: Procedure D; FIA MS m/z 663.4 (M+H)+.

EXAMPLE 1106

R=4-Cyclohexyl-1-oxobutyl: Procedure D; FIA MS m/z 616.4 (M+H)+.

EXAMPLE 1107

R=3-Methyl-1-oxobutyl: Procedure D; FIA MS m/z 548.2 (M+H)+, 546.2 (M−1)−.

EXAMPLE 1108

R=4-Methyl-1-oxopentyl: Procedure D; FIA MS m/z 562.2 (M+H)+, 560.4 (M−1)−.

EXAMPLE 1109

R=Cyclohexylacetyl: Procedure D; FIA MS m/z 588.2 (M+H)+, 586.4 (M−1)−.

EXAMPLE 1110

R=2-Adamantylaminocarbonyl: Procedure A; FIA MS m/z 641.4 (M+H)+.

EXAMPLE 1111

R=2-Thienylcarbonyl: Procedure A; FIA MS m/z 574.2 (M+H)+, 572.2 (M−1)−.

EXAMPLE 1112

R=Benzyloxycarbonyl: Procedure A; FIA MS m/z 598.2 (M+H)+, 596.4 (M−1)−.

EXAMPLE 1113

R=Allyloxycarbonyl: Procedure A; FIA MS m/z 548.2 (M+H)+.

EXAMPLE 1114

R=(1R,2S,5R)-2-Methyl-5-isopropylcyclohexyloxycarbonyl [(−)-Menthyloxycarbonyl]: Procedure A; FIA MS m/z 646.2 (M+H)+.

EXAMPLE 1115

R=2-Adamantylcarbonyl: Procedure A; FIA MS m/z 626.2 (M+H)+.

EXAMPLE 1116

R=3,3-Dimethyl-1-oxobutyl: Procedure A; FIA MS m/z 562.2 (M+H)+.

EXAMPLE 1117

R=2-Methylcyclopropylcarbonyl: Procedure D; FIA MS m/z 546.4 (M+H)+, 544.2 (M−1)−.

EXAMPLE 1118

R=2,2-Dimethyl-5-oxotetrahydrofuran-3-ylcarbonyl: Procedure D; FIA MS m/z 604.2 (M+H)+, 602.2 (M−1)−.

EXAMPLE 1119

R=trans-2-Phenylcyclopropylcarbonyl: Procedure D; FIA MS m/z 608.2 (M+H)+.

EXAMPLE 1120

R=(S)-1-Ethoxycarbonyl-3-methylbutylaminocarbonyl: Procedure A; FIA MS m/z 649.4 (M+H)+.

EXAMPLE 1121

R=(S)-1-Ethoxycarbonyl-2-methylpropylaminocarbonyl: Procedure A; FIA MS m/z 635.2 (M+H)+, 633.2 (M−1)−.

EXAMPLE 1122

R=(2S,3S)-2-(BOC-Amino)-3-methyl-1-oxopentyl [N—BOC-L-Isoleucyl]: Procedure D; FIA MS m/z 677.4 (M+H)+, 675.6 (M−1)−.

EXAMPLE 1123

R=4-t-Butylcyclohexylcarbonyl: Procedure D; FIA MS m/z 630.2 (M+H)+.

EXAMPLE 1124

R=(2S,3R)-2-(BOC-Amino)-3-t-butoxy-1-oxobutyl [N—BOC—O-t-Butyl-L-threonyl]: Procedure D; FIA MS m/z 721.4 (M+H)+, 719.4 (M−1)−.

EXAMPLE 1125

R=3-Thienylcarbonyl: Procedure D; FIA MS m/z 574.4 (M+H)+.

EXAMPLE 1126

R=3-Cyclohexyl-1-oxopropyl; Procedure D; FIA MS m/z 602.2 (M+H)+, 600.4 (M−1)−.

TABLE 12

Compounds of formula I which may be denoted by the following formula I-12

I-12 in which $R^q$ has the indicated value were prepared according to the indicated procedure from a requisite corresponding compound of formula I or formula III and the reagents and conditions appropriate for the indicated procedure or by a procedure otherwise noted.

EXAMPLE 1201

$R^q$=Benzyl: $N^1$-[4-Benzyloxy-2-(3-tert-butoxycarbonylaminopropoxy)benzoyl]-$N^2$-(4-methoxybenzoyl)-1,2-benzenediamine.

A. Methyl 4-benzyloxy-2-hydroxybenzoate

Methyl 4-hydroxysalicylate (20.0 g, 119 mmol) was dissolved in DMF (400 ml), then potassium carbonate (17.2 g, 125 mmol) and benzyl bromide (21.4 g, 125 mmol) were added, using additional DMF (400 ml) to aid the transfer. Potassium iodide (3.0 g) was added, and the reaction mixture was stirred at room temperature under nitrogen for 48 h. The DMF was removed in vacuo, the residue taken up in EtOAc, washed with water (3×), brine, and dried. The organic layer was concentrated in vacuo, and the crude product recrystallized from EtOAc:hexane to give 17.9 g (61.1%) of a white solid. A second recrystallization of material recovered from the filtrate yielded an additional 6.2 g (21.2%) of product.

B. Methyl 4-benzyloxy-2-(3-tert-butoxycarbonylaminopropoxy)benzoate

In a manner substantially equivalent to Example 201-B, methyl 4-benzyloxy-2-hydroxybenzoate (17.9 g, 72.7 mmol) gave, after silica gel purification on a Waters prep 500 (hexane:EtOAc), 26.5 g (87.7%) of a viscous, clear, colorless oil.

C. 4-Benzyloxy-2-(3-tert-butoxycarbonylaminopropoxy)benzoic acid

In a manner substantially equivalent to Example 101-C, methyl 4-benzyloxy-2-(3-tert-butoxycarbonylaminopropoxy)benzoate (26.0 g, 62.6 mmol) gave 22.5 g (89.6%) of the corresponding acid as a white solid.

D. $N^1$-[4-Benzyloxy-2-(3-tert-butoxycarbonylaminopropoxy)benzoyl]-$N^2$-(4-methoxybenzoyl)-1,2-benzenediamine In a manner substantially equivalent to Example 101-D, 4-benzyloxy-2-(3-tert-butoxycarbonylaminopropoxy)benzoic acid (4.98 g, 12.4 mmol) and $N^1$-(4-methoxybenzoyl)-1,2-benzenediamine (3.00 g, 12.4 mmol) were coupled to give 5.10 g (65.7%) of the title compound as a white foam after purification by silica gel (hexanes:EtOAc) chromatography on a Waters prep 500 instrument.

$^1$H NMR (300 MHz, DMSO-$d_6$);

FAB MS m/z 626.4 (M+H)+;

Anal. for $C_{36}H_{39}N_3O_7$:

Calcd: C, 69.10; H, 6.28; N, 6.72.

Found: C, 69.19; H, 6.30; N, 6.42.

Preparation 1202

[Corresponding Compound with $R^q$=H]: $N^1$-[2-(3-tert-Butoxycarbonylaminopropoxy)-4-hydroxybenzoyl]-$N^2$-(4-methoxybenzoyl)-1,2-benzenediamine.

Into an Erlynmeyer flask was weighed 10% Pd/C (0.150 g) and the Pd/C wetted with ethanol. $N^1$-[4-Benzyloxy-2-(3-tert-butoxycarbonylaminopropoxy)benzoyl]-$N^2$-(4-methoxybenzoyl)-1,2-benzenediamine (1.00 g, 1.60 mmol) was added in ethanol (60 ml), the flasked sealed with a septum, and the contents flushed with hydrogen gas (2×). The flask was fitted with a hydrogen-filled balloon, then shaken at room temperature. After 2.5 h, the palladium catalyst was filtered and washed with additional ethanol. The ethanol was removed in vacuo to give a colorless oil. The crude material was purified by silica gel chromatography (CHCl$_3$, EtOAc) to give 0.462 g (54%) of the indicated product as a white foam.

$^1$H NMR (300 MHz, DMSO-$d_6$);

FAB MS m/z 536.1 (M+H)+.

General Procedure F for the Mitsunobu Reaction of Phenols Such as the Compound Described in Example 1202:

An alcohol ($R^qOH$) of choice (56 µmol), $N^1$-[2-(3-tert-butoxycarbonylaminopropoxy)-4-hydroxybenzoyl]-$N^2$-(4-methoxybenzoyl)-1,2-benzenediamine (30.0 mg, 56 µmol), and triphenylphosphine (14.7 mg, 56 µmol) were combined in a 12×75 ml test tube which was then capped with a rubber septum. The tube was flushed with nitrogen, THF (0.5 ml) was added, and the tube cooled to −10° C. in a cold block. DIAD (11.3 mg, 56 µmol) was added, and the reaction mixture stirred for 18 h as the reaction block warmed to room temperature. The reaction mixture was loaded directly onto a SCX SPE column (Varian, 6 cc/1 g, preconditioned with methanol), the column was washed with CHCl$_3$:MeOH (9:1), and the product eluted with 9:1 CHCl$_3$:MeOH containing 0.2 N NH$_3$. The solvent was removed in vacuo and the residue purified by silica gel chromatography to give the desired ether.

EXAMPLE 1203

$R^q$=4-Pyridinylmethyl: Procedure F; FIA MS m/z 627.2 (M+H)+, 625.4 (M–1)–.

EXAMPLE 1204

$R^q$=2-(1-Pyrrolidinyl)ethyl: Procedure F; FIA MS m/z 633.2 (M+H)+.

EXAMPLE 1205

$R^q$=2-(4-Morpholinyl)ethyl: Procedure F; FIA MS m/z 649.4 (M+H)+, 647.4 (M–1)–.

EXAMPLE 1206

$R^q$=2-(1-Piperidinyl)ethyl; Procedure F; FIA MS m/z 647.4 (M+H)+, 645.6 (M–1)–.

bamoyl, aminomethyl, methyl, methoxy, difluoromethoxy, hydroxymethyl, methylthio, formyl, acetyl, vinyl, nitro, amino, hydroxy and 3,4-methylenedioxy; and in addition the phenyl may bear a chloro, fluoro, methyl, methoxy, or nitro substituent at the 2- and/or 6-position), or $Q^1$ is 5-membered ring heteroaryl (which 5-membered ring heteroaryl is a 5-membered aromatic ring which includes one to three heteroatoms selected from sulfur, oxygen and nitrogen and which is attached to the carbonyl at a carbon atom and further which may bear one or more methyl substituents on carbon or nitrogen and may bear one or more halo substituents), or $Q^1$ is 6-membered ring heteroaryl (which 6-membered ring heteroaryl is a 6-membered aromatic ring which includes one or two nitrogens and further which may bear one or more amino, chloro, fluoro, nitro, methoxy, methylthio, trifluoromethyl or methyl substituents);

$R^1$ is $-(CH_2)_i-Q-(CH_2)_j-NRR^a$ wherein:

a) Q is a single bond and the sum of i and j is 2, 3 or 4;
b) Q is $-C(CH_3)_2-$, i is 1, and j is 1;

---

---

What is claimed is:

1. A compound of formula I

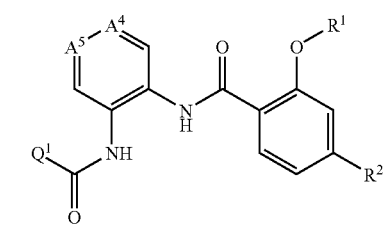

(or a pharmaceutically acceptable salt thereof) wherein:
each of $A^4$ and $A^5$ is CH, or
one of $A^4$ and $A^5$ is CH and the other is C—CN, or
one of $A^4$ and $A^5$ is CH and the other is N;
$Q^1$ is phenyl (in which the phenyl may bear one, two or three substituents at the 3-, 4- or 5-position(s) independently selected from halo, trifluoromethyl, cyano, carc) Q is $-CHR^b$, i is 0, j is 2, and $R^a$ and $R^b$ together are $-(CH_2)_2-$;
d) Q is $-CHR^b$, i is 2, j is 0, and $R^a$ and $R^b$ together are $-(CH_2)_4-$; or
e) Q is $-NR^b$; i is 2; j is 2; and $R^a$ and $R^b$ together are $-(CH_2)_2-$:

wherein, unless defined above, $R^a$ is hydrogen;
R is hydrogen, (1-6C)alkyl, $-CH_2R^c$, phenethyl, $-COR^d$, $-COCOR^e$, $-CO(CH_2)_f-R^f$ (in which f is 1, 2 or 3), $-CONH-R^g$, $-CSNH-R^h$, $-CO-OR^i$, $-SO_2R^j$ or $-SO_2NHR^k$;
$R^c$ is (3-6C)cycloalkyl, phenyl (in which the phenyl may bear one, two or three substituents independently selected from halo, trifluoromethyl, cyano, carbamoyl, aminomethyl, methyl, (1-2C)alkoxy, difluoromethoxy, hydroxymethyl, (1-4C)alkylthio, formyl, acetyl, vinyl, nitro, amino, hydroxy and 3,4-methylenedioxy), 5-membered ring heteroaryl (which 5-membered ring heteroaryl is a 5-membered aromatic ring which includes one to three heteroatoms selected from sulfur, oxygen and nitrogen and which is attached to the methylene at a carbon atom and further which may bear one or more methyl substituents on carbon or nitrogen and may bear one or more halo substituents on carbon), 6-membered ring heteroaryl (which 6-membered ring heteroaryl is a 6-membered aromatic ring which includes one or two nitrogens and further which may bear one or more amino, chloro, fluoro, nitro, methoxy, methylthio, trifluoromethyl or methyl substituents) or aminocarbonyl;

$R^d$ is (1-6C)alkyl, (3-6C)cycloalkyl (which cycloalkyl may bear one or two (1-4C)alkyl groups or a phenyl group), 2-adamantyl, phenyl (in which the phenyl may bear one, two or three substituents independently selected from halo, trifluoromethyl, cyano, carbamoyl, aminomethyl, methyl, (1-2C)alkoxy, difluoromethoxy, hydroxymethyl, (1-4C)alkylthio, formyl, acetyl, vinyl, nitro, amino, hydroxy and 3,4-methylenedioxy), 5-membered ring heteroaryl (which 5-membered ring heteroaryl is a 5-membered aromatic ring which includes one to three heteroatoms selected from sulfur, oxygen and nitrogen and which may bear one or more (1-4C)alkyl substituents on carbon and a methyl substituent on nitrogen and may bear one or more halo substituents or a methylsulfonyl substituent on carbon), 6-membered ring heteroaryl (which 6-membered ring heteroaryl is a 6-membered aromatic ring which includes one or two nitrogens and further which may bear one or more amino, chloro, fluoro, nitro, methoxy, methylthio, trifluoromethyl or methyl substituents), benzo[b]thien-2-yl, 1-methyl-5-oxopyrrolidin-3-yl, 2,2-dimethyl-5-oxotetrahydrofuran-3-yl, or 4-morpholinyl;

or —$COR^d$ is the acyl residue of a naturally occurring α-amino acid or a protected derivative thereof wherein the protecting group is comprised of a t-butoxycarbonyl (BOC) group for an amino residue, a t-butyl ether (O-t-Bu) group for a hydroxy residue, a benzylthioether (S-benzyl) for a sulfhydryl residue, an im-benzyl for a histidine imidazole residue and a benzyl ester for a carboxy residue, and wherein a methionine sulfur group may instead be the oxo or dioxo derivative and a proline nitrogen may bear a methyl, or the acyl residue is (S)-5-oxopyrrolidin-2-ylcarbonyl [L-pyroglutamyl], (R)-3-BOC-thiazolidin-4-ylcarbonyl or (R)-thiazolidin-4-ylcarbonyl;

$R^e$ is phenyl (which may bear one or more halo or methyl substituents), furanyl or thienyl;

$R^f$ is (3-6C)cycloalkyl, phenyl (which may bear one or more halo or methyl substituents) furanyl, thienyl, 4-methyl-1,2,5-thiadiazol-3-yl, pyrjdyl, carboxy, [(1-2C)alkoxy]carbonyl, dimethylamino, 4-morpholinyl, 1-tetrazolyl, or 2-(2-methoxyethoxy)ethoxy;

$R^g$ is (1-6C)alkyl, (3-6C)cycloalkyl, 2-adamantyl, phenyl (which may bear one or more halo, cyano or methyl substituents), —$(CH_2)_2R^w$ (in which $R^w$ is [(1-2C)alkoxy]-carbonyl or thienyl), —$(CH_2)_3R^x$ (in which $R^x$ is dimethylamino) or (S)-1-methoxycarbonyl-2-methylpropyl;

$R^h$ is phenyl (which may bear one or more halo or methyl substituents);

$R^i$ is (1-6C)alkyl, allyl, benzyl, 2-methoxyethyl or (1R,2S, 5R)-2-methyl-5-isopropylcyclohexyl [(−)-menthyl];

$R^j$ is phenyl (which may bear one or more halo, cyano or methyl substituents), 5-membered ring heteroaryl (which 5-membered ring heteroaryl is a 5-membered aromatic ring which includes one to three heteroatoms selected from sulfur, oxygen and nitrogen and which may bear one or more (1-4C)alkyl substituents on carbon and a methyl substituent on nitrogen and may bear one or more halo substituents or a pyridyl or [(1-2C)alkoxy]carbonyl substituent on carbon);

$R^k$ is phenyl (which may bear one or more halo, or methyl substituents); and $R^2$ is (1-4C)alkyl or —O—$R^q$ wherein $R^q$ is (1-4C)alkyl, 4-pyridinylmethyl or —$(CH_2)_2R^r$, in which $R^r$ is 1-pyrrolidinyl, 1-piperidinyl or 4-morpholinyl.

2. The compound as claimed in claim 1 wherein: halo is fluoro, chloro, bromo or iodo; for an alkyl group or the alkyl portion of an alkoxy or alkylthio group: (1-2C)alkyl is methyl or ethyl; (1-4C)alkyl is methyl, ethyl, propyl, isopropyl, butyl, 2-methylpropyl or t-butyl: (1-6C)alkyl is methyl, ethyl, propyl, isopropyl, butyl, 2-methylpropyl, t-butyl; pentyl, 3-methylbutyl, 2,2-dimethylpropyl, hexyl or 3,3-dimethylbutyl; (3-6C)cycloalkyl is cyclopropyl, cyclobutyl, cyclopentyl or cyclohexyl.

3. The compound as claimed in claim 2 wherein $Q^1$ is 4-methoxyphenyl, 4-chlorophenyl or 5-chloropyridin-2-yl.

4. The compound as claimed in claim 3 wherein $Q^1$ is 4-methoxyphenyl.

5. The compound as claimed in claim 2 wherein $R^2$ is t-butyl, methoxy, ethoxy, 4-pyridinylmethoxy or —O—$(CH_2)_2$—$R^r$, in which $R^r$ is 1-pyrrolidinyl, 1-piperidinyl or 4-morpholinyl.

6. The compound as claimed in claim 5 wherein $R^2$ is t-butyl, methoxy or ethoxy.

7. The compound as claimed claim 2 wherein R is hydrogen, isopropyl, 2,2-dimethylpropyl, cyclopropylmethyl, benzyl (the phenyl of which may bear a methylenedioxy, ethoxy, t-butylthio, nitro, bromo, chloro or trifluoromethyl substituent or one or two independently selected fluoro, methyl or methoxy substituents), 2-thienylmethyl, 3-thienylmethyl (which may bear a 2-methyl substituent), 2-pyrrolylmethyl (which may bear a 1-methyl substituent), 5-methylimidazol-4-ylmethyl, 2-pyridylmethyl, aminocarbonylmethyl, phenethyl, acetyl, pivaloyl, 3-methylbutanoyl, 3,3-dimethylbutanoyl, 4-methylpentanoyl, 2-methyl-cyclopropylcarbonyl, trans-2-phenylcyclopropylcarbonyl, 4-t-butylcyclohexylcarbonyl, 2-adamantylcarbonyl, benzoyl (which may bear a fluoro, methyl, 4-t-butyl, methoxy or methylthio substituent), 2- or 3-furancarbonyl (which may bear a t-butyl, chloro or bromo substituent or one or two methyl substituents), 2- or 3-thiophenecarbonyl (which may bear a chloro, bromo, methyl or methylsulfonyl substituent or two chloro substituents or a bromo and a methyl substituent), 1-methylpyrrole-2-carbonyl, 5-methylisoxazol-3-ylcarbonyl, 5-thiazolylcarbonyl, 1-methylpyrazol-4-ylcarbonyl, 2-methyl-2H-pyrazol-3-ylcarbonyl 2,5-dimethyl-2H-pyrazol-3-ylcarbonyl, 2-pyridylcarbonyl, 3-pyridylcarbonyl (which may bear a chloro or methyl substituent at the 2-position), benzo[b]thien-2-ylcarbonyl, 1-methyl-5-oxopyrrolidin-3-ylcarbonyl, 2,2-dimethyl-5-oxotetrahydrofuran-3-ylcarbonyl, 4-morpholinylcarbonyl, 2-(2-fluorophenyl)-2-oxoacetyl, 2-(2-thienyl)-2-oxoacetyl, cyclohexylacetyl, 3-cyclohexyl-1-oxopropyl, 4-cyclohexyl-1-oxobutyl, 2-fluorophenylacetyl, 4-fluorophenylacetyl, 2-thienylacetyl, 3-(2-thienyl)-1-oxopropyl, 4-(2-thienyl)-1-oxobutyl, 3-thienylacetyl, 4-methyl-1,2,5-thiadiazol-3-ylacetyl, 3-(2-pyridyl)propanoyl, 3-carboxypropanoyl, dimethylaminoacetyl, 3-(4-morpholinyl)-1-oxopropyl, (1-tetrazolyl)acetyl, 2-(2-methoxyethoxy)ethoxyacetyl, —CONH—$R^g$ [in which $R^g$ is methyl, ethyl, isopropyl, butyl, cyclohexyl, 2-adamantyl, phenyl, 2-fluorophenyl, 2-chlorophenyl, 4-cyanophenyl, 2-(ethoxycarbonyl)ethyl, 2-(2-thienyl)ethyl, 2-(3-thienyl)ethyl, 3-(dimethylamino)propyl or (S)-1-methoxycarbonyl-2-methylpropyl], 2-fluorophenylaminothiocarbonyl, t-butoxycarbonyl, allyloxycarbonyl, benzyloxycarbonyl, (2-methoxyethoxy)carbonyl, (1R,2S,5R)-2-methyl-5-isopropylcyclohexyloxycarbonyl[(−)-menthyloxycarbonyl], 4-cyanophenylsulfonyl, 2-thienylsulfonyl, 2-methoxycarbonylthien-3-ylsulfonyl, 5-(2-pyridinyl)thien-2-ylsulfonyl, 3,5-dimethylisoxazol-4-ylsulfonyl, 5-chloro-1,3-dimethylpyrazol-4-ylsulfonyl, (2-fluorophenyl)aminosulfonyl; or R is (S)-2,6-bis(BOC-amino)-1-oxohexyl[$N^2,N^6$-di-BOC-L-Lysyl], (S)-1-methylpyrrolidin-2-ylcarbonyl[1-methyl-L-Prolyl], (S)-2-(BOC-amino)-1-oxopropyl[N—BOC-L-Alanyl], (S)-2-(BOC-amino)-3-hydroxy-1-oxopropyl [N—BOC-L-Seryl], (S)-2-(BOC-amino)-4-methylthio-1-oxobutyl[N—BOC-L-Methionyl], (S)-2-(BOC-amino)-4-methylsulfinyl-1-oxobutyl[N—BOC—S-Oxo-L-methionyl], (2S,3R)-2-(BOC-amino)-3-t-butoxy-1-oxobutyl[N—BOC—O-t-Butyl-L-threonyl], (S)-2-(BOC-Amino)-3-(benzyloxycarbonyl)-1-oxopropyl[N—BOC-β-Benzyl-L-α-aspartyl], (2S,3S)-2-(BOC-amino)-3-methyl-1-oxopentyl[N—BOC-L-Isoleucyl], (S)-2-(BOC-amino)-4-methyl-1-oxopentyl[N—BOC-L-Leucyl], (S)-2-(BOC-amino)-3-methyl-1-oxobutyl [N—BOC-L-Valyl], (R)-3-BOC-thiazolidin-4-ylcarbonyl, or (S)-5-oxopyrrolidin-2-ylcarbonyl[L-Pyroglutamyl].

8. The compound as claimed in claim 7 wherein R is hydrogen or a value of —$COR^d$.

9. The compound as claimed in claim 2 wherein Q is a single bond and the sum of i and j is 3, or Q is —$CHR^b$, i is 0, j is 2, and $R^a$ and $R^b$ together are —$(CH_2)_2$—.

10. The compound as claimed in any one of claims 1-9 wherein each of $A^4$ and $A^5$ is CH.

11. The compound as claimed in any one of claims 1-9 wherein $A^4$ is CH and $A^5$ is N.

12. The pharmaceutically acceptable salt of a compound of formula I as claimed in claim 1 which is an acid-addition salt made from a basic compound of formula I and an acid which provides a pharmaceutically acceptable anion or a salt which is made from an acidic compound of formula I and a base which provides a pharmaceutically acceptable cation.

13. A pharmaceutical composition comprising in association with a pharmaceutically acceptable carrier, diluent or excipient, a compound of formula I (or a pharmaceutically acceptable salt thereof) as provided in claim 1.

14. A method of treating a thromboembolic disorder in a mammal in need of treatment comprising administering to the mammal an effective amount of a compound of formula I, or pharmaceutically acceptable salt thereof, as described in claim 1.

\* \* \* \* \*